US009029427B2

(12) United States Patent
Endo et al.

(10) Patent No.: US 9,029,427 B2
(45) Date of Patent: May 12, 2015

(54) CONTROLLED RELEASE SOLID PREPARATION

(75) Inventors: Masaaki Endo, Tokyo (JP); Kazuhiro Obae, Tokyo (JP); Ichirou Ibuki, Tokyo (JP); Yoshihito Yaginuma, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 1444 days.

(21) Appl. No.: 12/084,824

(22) PCT Filed: Nov. 10, 2006

(86) PCT No.: PCT/JP2006/322487
§ 371 (c)(1),
(2), (4) Date: May 9, 2008

(87) PCT Pub. No.: WO2007/055329
PCT Pub. Date: May 18, 2007

(65) Prior Publication Data
US 2009/0269401 A1    Oct. 29, 2009

(30) Foreign Application Priority Data

Nov. 11, 2005    (JP) ................................ 2005-327490

(51) Int. Cl.
| | | |
|---|---|---|
| A61K 47/36 | (2006.01) | |
| A61K 9/20 | (2006.01) | |
| A61K 9/24 | (2006.01) | |
| A01N 25/10 | (2006.01) | |

(52) U.S. Cl.
CPC ............. *A61K 9/2086* (2013.01); *A61K 9/2018* (2013.01); *A61K 9/2031* (2013.01); *A61K 9/2054* (2013.01); *A61K 9/2059* (2013.01); *A61K 9/209* (2013.01)

(58) Field of Classification Search
CPC .......................... A61K 9/1652; A61K 9/2059
See application file for complete search history.

(56) References Cited

U.S. PATENT DOCUMENTS

| | | | |
|---|---|---|---|
| 3,184,386 A * | 5/1965 | Stephenson .................... | 424/471 |
| 5,456,921 A | 10/1995 | Mateescu et al. | |
| 5,549,913 A | 8/1996 | Colombo et al. | |
| 5,667,803 A | 9/1997 | Paronen et al. | |
| 5,688,510 A * | 11/1997 | Nakamichi et al. ........... | 424/736 |
| 5,879,707 A | 3/1999 | Cartilier et al. | |
| 5,885,615 A | 3/1999 | Chouinard et al. | |
| 6,296,873 B1 | 10/2001 | Katzhendler et al. | |
| 6,733,782 B1 | 5/2004 | Huet De Barochez et al. | |
| 2002/0012701 A1 | 1/2002 | Kolter et al. | |
| 2002/0192291 A1 | 12/2002 | Bergsma et al. | |
| 2004/0081693 A1 | 4/2004 | Woo et al. | |
| 2004/0197404 A1 | 10/2004 | Ellstrom et al. | |

FOREIGN PATENT DOCUMENTS

| | | | |
|---|---|---|---|
| EP | 0661045 A1 | 7/1995 | |
| JP | 61-5027 | 1/1986 | |
| JP | 62-149632 | 7/1987 | |
| JP | 63-54319 | 3/1988 | |
| JP | 2-209 | 1/1990 | |
| JP | 4-318001 | 11/1992 | |
| JP | 5-262649 | 10/1993 | |
| JP | 6-172161 | 6/1994 | |
| JP | 6-305982 | 11/1994 | |
| JP | 7-8809 | 2/1995 | |
| JP | 7-51516 | 6/1995 | |
| JP | 8-502036 | 3/1996 | |
| JP | 10-502056 | 2/1998 | |
| JP | 11-5739 | 1/1999 | |
| JP | 2000-507561 | 6/2000 | |
| JP | 2000-517351 | 12/2000 | |
| JP | 2001-10951 | 1/2001 | |
| JP | 2001-502700 | 2/2001 | |
| JP | 2002-20319 | 1/2002 | |
| JP | 2002-525310 | 8/2002 | |
| JP | 2002-363106 | 12/2002 | |
| JP | 2003-510265 | 3/2003 | |
| JP | 2004-107351 | 4/2004 | |
| JP | 2004-143175 | 5/2004 | |
| JP | 2005-504052 | 2/2005 | |
| WO | 87/05212 | 9/1987 | |
| WO | 92/15285 | 9/1992 | |
| WO | WO-9215285 | * 9/1992 | ............... A61K 9/20 |
| WO | 94/02121 | 2/1994 | |
| WO | 99/09066 | 2/1999 | |

(Continued)

OTHER PUBLICATIONS

Sanghivi et al. (Pharmaceutical Research 1993, 10, 1597-1603).*
McKenna (J. Pharm. Pharmacol. 1982, 34 347-351).*
Masahiro Nakano, et al., "Preparation and Evaluation of Sustained Release Tablets Prepared with α-Starch", *Chem. Pharm. Bull.* vol. 35, No. 10, pp. 4346-4350, 1987.
J. Herman, et al., "Modified-starches as hydrophilic matrices for controlled oral delivery. I. Production and characterization of thermally modified starches", *International Journal of Pharmaceuticals*, 56 (1989), pp. 51-63.
J. Herman, et al., "Modified-starches as hydrophilic matrices for controlled oral delivery. II. In vitro drug release evaluation of thermally modified starches", *International Journal of Pharmaceuticals*, 56 (1989), pp. 65-70.

(Continued)

*Primary Examiner* — Abigail Fisher
*Assistant Examiner* — Jessica Kassa
(74) *Attorney, Agent, or Firm* — Staas & Halsey LLP

(57) ABSTRACT

Disclosed is a solid preparation which comprises at least one active ingredient and at least one dissolution-controlling base substance and can be formed by compression molding, wherein the dissolution-controlling base substance contains 5.0 to 99.9% by weight (inclusive) of a modified starch having a moisture retaining capacity of 400% or more and a gel indentation load of 200 g or more, containing a water-soluble ingredient in an amount of 40 to 95% by weight, having particles passing through a 75 μm-mesh sieve in the proportion of 90% by weight or more and particles passing through a 32 μm-mesh sieve in the proportion of 20% by weight or more, and having an average particle diameter of not smaller than 20 μm and smaller than 50 μm.

43 Claims, 14 Drawing Sheets

(56) References Cited

FOREIGN PATENT DOCUMENTS

| WO | 01/22940 A1 | 4/2001 |
|---|---|---|
| WO | 2005/000296 A1 | 1/2005 |
| WO | 2005/005484 A1 | 1/2005 |
| WO | 2005/074976 A1 | 8/2005 |
| WO | 2006-514687 | 5/2006 |

OTHER PUBLICATIONS

P. van Aerde, et al., "In vitro evaluation of modified starches as matrices for sustained release dosage forms", *International Journal of Pharmaceuticals*, 45 (1988), pp. 145-152.

Yoshiaki Kawashima, et al., "Low-Sustained Hydroxypropylcelluclose as a Sustained-Drug Release Matrix Base or Disintegrant Depending On Its Particle Size and Loading in Formulation", *Pharmaceutical Research*, vol. 10, No. 3, 1993, pp. 351-355.

Paul Wan Sia Heng, et al., "Investigation of the influence of mean HPMC particle size and number of polymer particles on the release of aspirin from swellable hydrophilic matric tablets", *Journal of Controlled Release* 76 (2001), pp. 39-49.

* cited by examiner

FIG.7

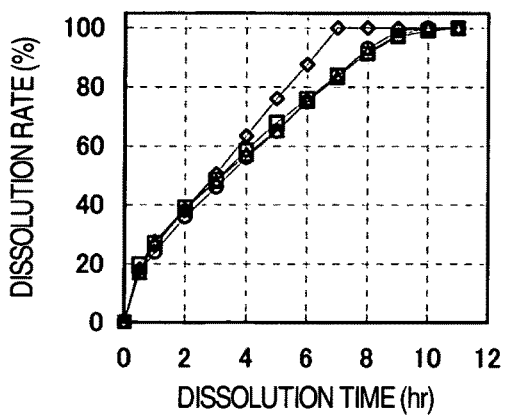

○ TABLET A - 1 (EXAMPLE 1) / SECOND SOLUTION, ROTATING BASKET METHOD [100rpm]
△ TABLET A - 1 (EXAMPLE 1) / McIlvaine SOLUTION, ROTATING BASKET METHOD [100rpm]
□ TABLET A - 2 (EXAMPLE 1) / SECOND SOLUTION, ROTATING BASKET METHOD [100rpm]
◇ TABLET A - 1 (EXAMPLE 1) / SECOND SOLUTION, PADDLE METHOD [200rpm]

FIG.8

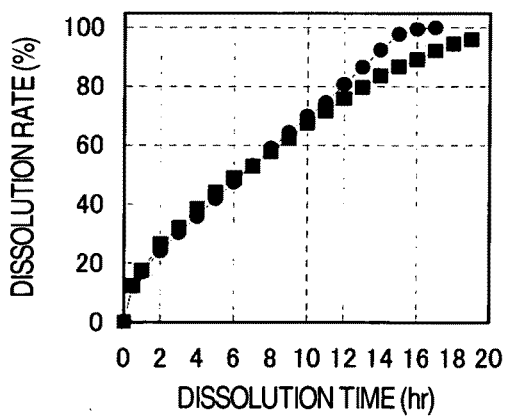

● TABLET A - 3 (EXAMPLE 1) / SECOND SOLUTION, ROTATING BASKET METHOD [100rpm]
■ TABLET M - 3 (COMPARATIVE EXAMPLE 6) / SECOND SOLUTION, ROTATING BASKET METHOD [100rpm]

● TABLET B (EXAMPLE 2) / SECOND SOLUTION, PADDLE METHOD [200rpm]
■ TABLET K (COMPARATIVE EXAMPLE 4) / SECOND SOLUTION, PADDLE METHOD [200rpm]

● TABLET C (EXAMPLE 3) / SECOND SOLUTION, PADDLE METHOD [200rpm]
▲ TABLET D (EXAMPLE 3) / SECOND SOLUTION, PADDLE METHOD [200rpm]
■ TABLET E (EXAMPLE 3) / SECOND SOLUTION, PADDLE METHOD [200rpm]
□ TABLET G (COMPARATIVE EXAMPLE 5) / SECOND SOLUTION, PADDLE METHOD [200rpm]

● TABLET F (EXAMPLE 4) / SECOND SOLUTION, PADDLE METHOD [200rpm]

● TABLET G (EXAMPLE 5) / SECOND SOLUTION, PADDLE METHOD [200rpm]

FIG.13

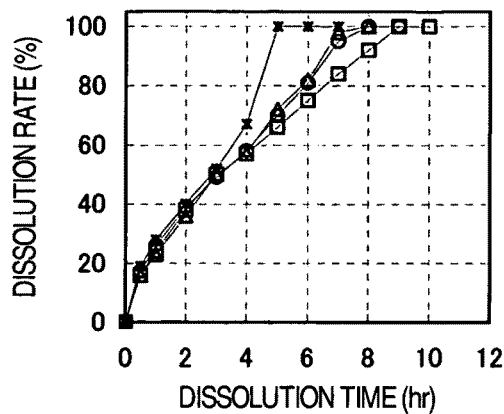

○ TABLET H - 1 (COMPARATIVE EXAMPLE 1) / SECOND SOLUTION, ROTATING BASKET METHOD [100rpm]
△ TABLET H - 1 (COMPARATIVE EXAMPLE 1) / Mcilvaine SOLUTION, ROTATING BASKET METHOD [100rpm]
□ TABLET H - 2 (COMPARATIVE EXAMPLE 1) / SECOND SOLUTION, ROTATING BASKET METHOD [100rpm]
◇ TABLET H - 1 (COMPARATIVE EXAMPLE 1) / SECOND SOLUTION, PADDLE METHOD [200rpm]

FIG.14

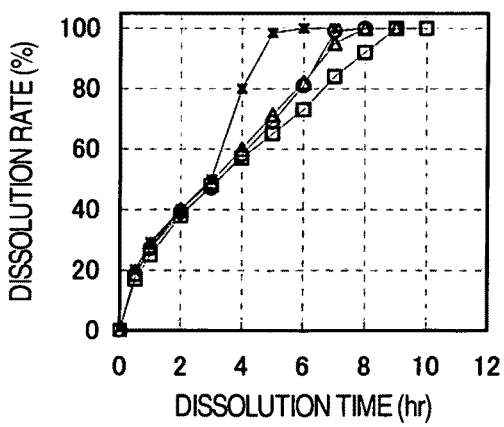

○ TABLET I - 1 (COMPARATIVE EXAMPLE 2) / SECOND SOLUTION, ROTATING BASKET METHOD [100rpm]
△ TABLET I - 1 (COMPARATIVE EXAMPLE 2) / Mcilvaine SOLUTION, ROTATING BASKET METHOD [100rpm]
□ TABLET I - 2 (COMPARATIVE EXAMPLE 2) / SECOND SOLUTION, ROTATING BASKET METHOD [100rpm]
◇ TABLET I - 1 (COMPARATIVE EXAMPLE 2) / SECOND SOLUTION, PADDLE METHOD [200rpm]

FIG. 15

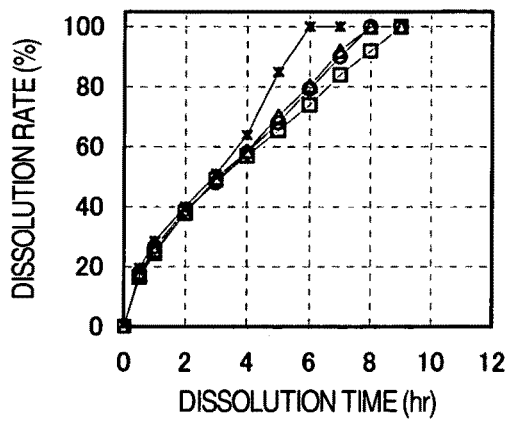

○ TABLET J-1 (COMPARATIVE EXAMPLE 3) / SECOND SOLUTION, ROTATING BASKET METHOD [100rpm]
△ TABLET J-1 (COMPARATIVE EXAMPLE 3) / McIlvaine SOLUTION, ROTATING BASKET METHOD [100rpm]
□ TABLET J-2 (COMPARATIVE EXAMPLE 3) / SECOND SOLUTION, ROTATING BASKET METHOD [100rpm]
◇ TABLET J-1 (COMPARATIVE EXAMPLE 3) / SECOND SOLUTION, PADDLE METHOD [200rpm]

FIG. 16

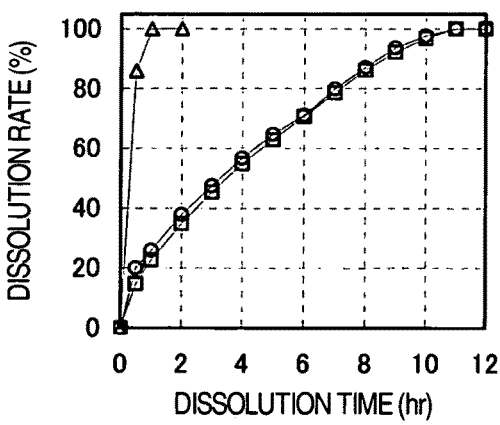

○ TABLET M-1 (COMPARATIVE EXAMPLE 6) / SECOND SOLUTION, ROTATING BASKET METHOD [100rpm]
△ TABLET M-1 (COMPARATIVE EXAMPLE 6) / McIlvaine SOLUTION, ROTATING BASKET METHOD [100rpm]
□ TABLET M-2 (COMPARATIVE EXAMPLE 6) / SECOND SOLUTION, ROTATING BASKET METHOD [100rpm]

FIG. 17

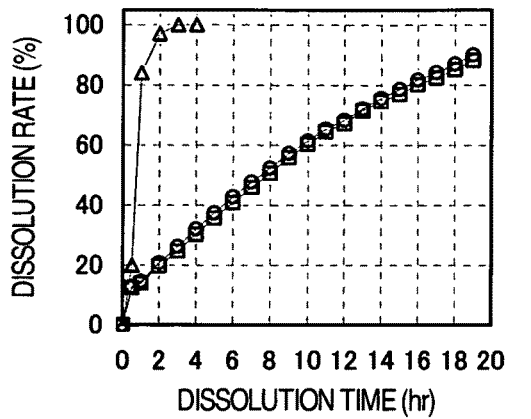

○ TABLET N - 1 (COMPARATIVE EXAMPLE 7) / SECOND SOLUTION, ROTATING BASKET METHOD [100rpm]
△ TABLET N - 1 (COMPARATIVE EXAMPLE 7) / McIlvaine SOLUTION, ROTATING BASKET METHOD [100rpm]
□ TABLET N - 2 (COMPARATIVE EXAMPLE 7) / SECOND SOLUTION, ROTATING BASKET METHOD [100rpm]

FIG. 18

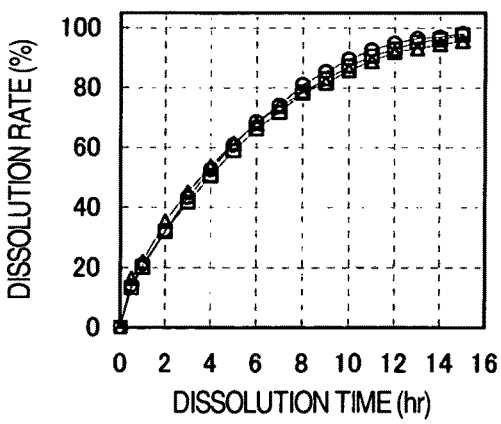

○ TABLET O - 1 (COMPARATIVE EXAMPLE 8) / SECOND SOLUTION, ROTATING BASKET METHOD [100rpm]
△ TABLET O - 1 (COMPARATIVE EXAMPLE 8) / McIlvaine SOLUTION, ROTATING BASKET METHOD [100rpm]
□ TABLET O - 2 (COMPARATIVE EXAMPLE 8) / SECOND SOLUTION, ROTATING BASKET METHOD [100rpm]

FIG.19

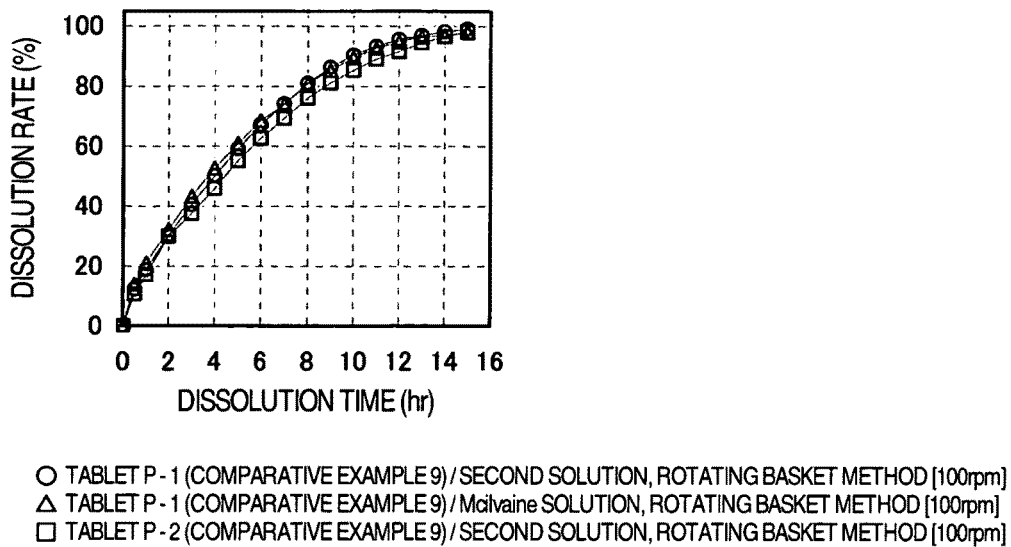

○ TABLET P-1 (COMPARATIVE EXAMPLE 9) / SECOND SOLUTION, ROTATING BASKET METHOD [100rpm]
△ TABLET P-1 (COMPARATIVE EXAMPLE 9) / McIlvaine SOLUTION, ROTATING BASKET METHOD [100rpm]
□ TABLET P-2 (COMPARATIVE EXAMPLE 9) / SECOND SOLUTION, ROTATING BASKET METHOD [100rpm]

FIG.20

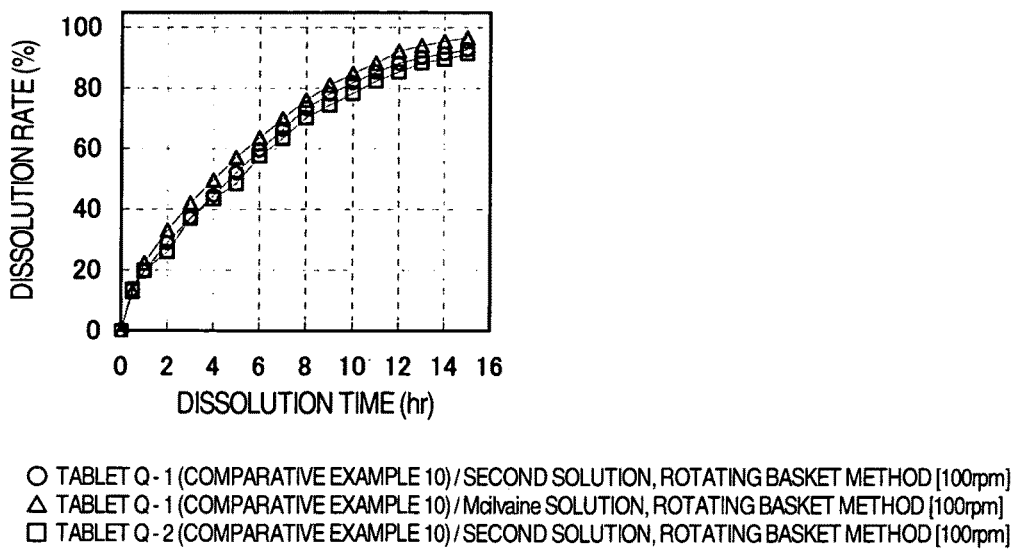

○ TABLET Q-1 (COMPARATIVE EXAMPLE 10) / SECOND SOLUTION, ROTATING BASKET METHOD [100rpm]
△ TABLET Q-1 (COMPARATIVE EXAMPLE 10) / McIlvaine SOLUTION, ROTATING BASKET METHOD [100rpm]
□ TABLET Q-2 (COMPARATIVE EXAMPLE 10) / SECOND SOLUTION, ROTATING BASKET METHOD [100rpm]

FIG.21

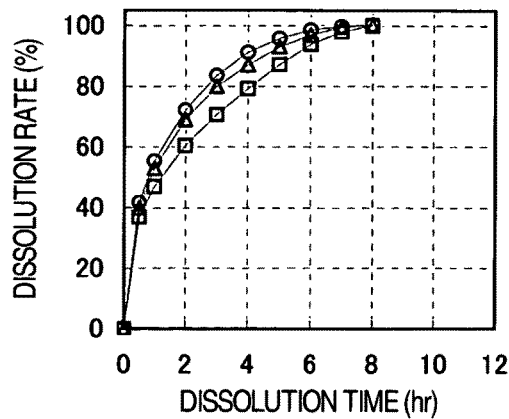

○ TABLET R-1 (COMPARATIVE EXAMPLE 11) / SECOND SOLUTION, ROTATING BASKET METHOD [100rpm]
△ TABLET R-1 (COMPARATIVE EXAMPLE 11) / Mcilvaine SOLUTION, ROTATING BASKET METHOD [100rpm]
□ TABLET R-2 (COMPARATIVE EXAMPLE 11) / SECOND SOLUTION, ROTATING BASKET METHOD [100rpm]

FIG.22

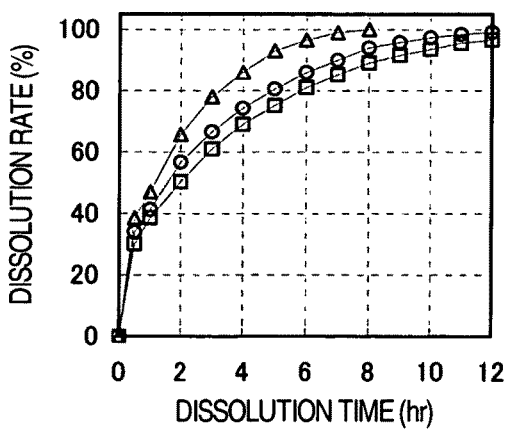

○ TABLET S-1 (COMPARATIVE EXAMPLE 12) / SECOND SOLUTION, ROTATING BASKET METHOD [100rpm]
△ TABLET S-1 (COMPARATIVE EXAMPLE 12) / Mcilvaine SOLUTION, ROTATING BASKET METHOD [100rpm]
□ TABLET S-2 (COMPARATIVE EXAMPLE 12) / SECOND SOLUTION, ROTATING BASKET METHOD [100rpm]

▲ CORE TABLET A (EXAMPLE 6) / SECOND SOLUTION, PADDLE METHOD [200rpm]
● CORE TABLET B (EXAMPLE 6) / SECOND SOLUTION, PADDLE METHOD [200rpm]
■ CORE TABLET C (EXAMPLE 6) / SECOND SOLUTION, PADDLE METHOD [200rpm]

▲ CORE TABLET D (EXAMPLE 7) / SECOND SOLUTION, PADDLE METHOD [200rpm]
● CORE TABLET E (EXAMPLE 7) / SECOND SOLUTION, PADDLE METHOD [200rpm]

▲ CORE TABLET F (EXAMPLE 8) / SECOND SOLUTION, PADDLE METHOD [200rpm]
● CORE TABLET G (EXAMPLE 8) / SECOND SOLUTION, PADDLE METHOD [200rpm]
■ CORE TABLET H (EXAMPLE 8) / SECOND SOLUTION, PADDLE METHOD [200rpm]
◆ CORE TABLET I (EXAMPLE 8) / SECOND SOLUTION, PADDLE METHOD [200rpm]

▲ CORE TABLET J (EXAMPLE 9) / SECOND SOLUTION, PADDLE METHOD [200rpm]

▲ CORE TABLET L (EXAMPLE 11) / SECOND SOLUTION, PADDLE METHOD [200rpm]

CONTROLLED RELEASE SOLID PREPARATION

CROSS REFERENCE TO RELATED APPLICATIONS

This application claims the benefit under 35 U.S.C. §371, of PCT International Application Number PCT/JP2006/322487, filed Nov. 10, 2006, which claimed priority to Japanese Application No. 2005-327490, filed Nov. 11, 2005 in Japan, the contents of which are incorporated herein by reference.

TECHNICAL FIELD

The present invention relates to a solid preparation which controls dissolution of active ingredient in such uses as medicines, agricultural chemicals, fertilizers, feeds, foods, industries, and cosmetics. More particularly, it relates to a controlled release solid preparation which is not affected by environments in living organisms such as ionic strength and pH, compressive force in compression molding, and kind and content of active ingredient, less in change of residence time in gastrointestinal tracts, and can be controlled in release of active ingredient to zero-order, two or more stage or timed-release.

BACKGROUND ART

Controlled release solid preparations are useful in medical use since the number of administration can be reduced and administrative manner can be improved by controlling the concentration of active ingredient in blood; prolonged action of active ingredient short in period of dissipation half decay in living organisms can be improved; and side-effect of active ingredient narrow in width between minimum concentration in blood and side-effect developing concentration in blood can be reduced.

For controlling dissolution of active ingredient to slow release, a method of uniformly dispersing active ingredient together with a dissolution-controlling base substance and compression molding the dispersion is practically used because stable dissolution control can be attained, and structure and production process are simple and rapid development can be made (matrix system). As the dissolution controlling base substances, there are used hydrophilic dissolution-controlling base substances, lipophilic dissolution-controlling base substances, inert dissolution-controlling base substances (belonging to thermoplastic polymers), etc.

As examples of hydrophilic dissolution-controlling base substances, there are known cellulose derivatives such as methyl cellulose (MC), hydroxypropyl cellulose (HPC), hydroxypropylmethyl cellulose (HPMC), etc. as disclosed in Patent Document 1, etc. These base substances have characteristics that they can control the active ingredient to slow release without being affected with pH and are superior in time stability. However, cellulose derivatives are greatly swollen by hydration, and hence the solid preparation is greatly swollen in compression direction in a dissolution solution with progress of gelation. As a result, diffusion distance for dissolution of active ingredient becomes longer in the later period of dissolution, causing decrease of dissolution speed. Therefore, they have a defect that it is difficult to accurately control to zero-order dissolution. Commercially available cellulose derivatives include generally those grades which are different in viscosity, and those of high viscosity are superior in ability to slowly release the active ingredient. However, those of higher viscosity tend to be greater in swelling in compression direction, and can hardly accurately control to zero-order dissolution.

Patent Documents 2, 3, etc. disclose a method of adding water-soluble ingredients as a method for adjusting dissolution properties of cellulose derivatives. Patent Document 2 discloses to use sorbitol and polyethylene glycol as dissolution-adjusting agents for slower or faster release in controlled release solid preparations containing a gel-forming polymer such as HPMC as a dissolution-controlling base substance. However, Patent Document 2 has no examples of using the dissolution-adjusting agents and does not specifically disclose effects obtained by using the dissolution-adjusting agents. Furthermore, as known for one skilled in the art, these dissolution-adjusting agents are expected to exhibit the effect to totally delay or hasten the dissolution speed of active ingredient, but cannot improve the problem of decrease in dissolution speed in the later period of dissolution. Patent Document 3 mentions controlled release solid preparations using a cellulose polymer compound such as HPMC as a dissolution-controlling base substance and containing glucose syrup, and discloses that the active ingredient is linearly dissolved. However, in the results of a dissolution test given in Examples, the dissolution rate decreases in the later period of dissolution, and thus decrease of dissolution speed in the later period cannot be improved sufficiently.

Patent Document 4 discloses a method of using a multilayer tablet comprising a swelling layer containing active ingredient and an erosive and/or soluble layer for the purpose of improving the decrease of dissolution speed in the later period of dissolution caused by swelling of cellulose derivative. According to this method, the erosive and/or soluble layer diminish in the later period of dissolution, to cause increase of the surface area of the swelling layer containing active ingredient and thus to inhibit decrease of dissolution rate in the later period of dissolution. However, in order to improve the problem of decrease in dissolution speed in the later period of dissolution, complicated design for preparation is required.

Moreover, in a solution having great ionic strength value, cellulose derivatives compete for hydration with solute which gives ionic strength. Thus, gelation is insufficient and the form of matrix cannot be maintained and broken. It is known that the ionic strength value in gastrointestinal tracts differs depending on not only the areas, but also on the foods taken, and it changes in the range of about 0.01 to about 0.2. Therefore, cellulose derivatives further have the problem that they are inhibited from hydration at an ionic strength of medium or higher value in an environment of gastrointestinal tracts where ionic strength changes, resulting in breakage of matrix. If so-called dose dumping occurs where abrupt dissolution of the remaining active ingredient occurs due to breakage of matrix, concentration in blood abruptly rises. As a result, death may be caused according to the efficacy of the active ingredient narrow in width between the minimum concentration in blood and the side-effect developing concentration in blood. It is necessary that controlled release solid preparations in the field of medicines perform are accurately controlled in dissolution of active ingredient also in the environment of gastrointestinal tracts where ionic strength changes. Therefore, there are demanded controlled release solid preparations having stable dissolution controllability in a solution where ionic strength changes, particularly, in a solution of high ionic strength.

Patent Documents 5-9 relate to methods for improving the dissolution controllability of HPC and HPMC. These documents disclose methods for finely dividing HPC and HPMC to contain 50% by weight or more of particles passing through a 100 mesh (about 150 µm-mesh) sieve for HPC and 95% by weight or more of particles passing through a 100 mesh (about 150 µm-mesh) sieve for HPMC. According to these methods, hydration rate is accelerated by finely dividing HPC and HPMC, a gel layer can be rapidly formed, and disintegration of tablets which occurs in the initial period of dissolution of active ingredient can be inhibited to prevent excessive dissolution. However, use of the fine particles in Patent Documents 5-9 does not improve swelling of particles. Therefore, it cannot improve the problem of decrease in dissolution speed in the later period of dissolution, and besides cannot solve the problem of disintegration in a solution of high ionic strength.

Among cellulose derivatives, HPMC is one of the dissolution-controlling base substances which have hitherto been used most frequently. However, in addition to the above problems, HPMC has further problems in physical properties of powder that it is inferior in flowability, has somewhat yellowish color and is inferior in whiteness and has irritating odor peculiar to synthetic paste, and these many problems are desired to be solved.

As other hydrophilic dissolution controlling base substances of cellulose derivatives, there are known non-cellulose polysaccharides such as xanthan gum and locust bean gum, and synthetic polymers such as polyethylene oxide and acrylic polymers. These dissolution-controlling base substances have such properties that generally they are greater in swelling than cellulose derivatives and greatly swell not only in the compression direction, but also in the direction perpendicular to the compression direction, and are enlarged with lapse of time. Therefore, they have a defect that dissolution speed decreases in the later period of dissolution. In addition, since there is the possibility of causing change in residence time in gastrointestinal tracts, they are not necessarily satisfactory controlled release solid preparations in the field of medicines in which good reproducibility and accurate dissolution are required.

Patent Documents 10-12 disclose methods of adjusting dissolution by adding water-soluble ingredients to non-cellulose polysaccharides or synthetic polymers. Patent Document 10 discloses controlled release solid preparations which contain a heteropolysaccharide gum or a homopolysaccharide gum crosslinkable with the heteropolysaccharide gum and further contain a monosaccharide, disaccharide or polyhydric alcohol as an inert diluent. However, it makes no mention of influence given by the inert diluent on dissolution of active ingredients.

Patent Document 11 discloses controlled release solid preparations containing a carrier for release control such as sodium alginate or xanthan gum and a gel hydration accelerator. It discloses that a mixture of HPMC and propylene glycol alginate ester is preferred as the gel hydration accelerator. It further discloses that since non-gelling core is not formed due to the rapid gel hydration, the dissolution is not influenced by movement speed of gastrointestinal tracts, and zero-order dissolution may occur. However, the controlled release preparations disclosed in Examples are all those in which dissolution of active ingredient hardly occur for two hours after starting of test, and are special ones differing in dissolution from zero-order dissolution generally required in the use of medicines.

Patent Document 12 discloses controlled release solid preparations containing a polymer which forms hydrogel, such as polyethylene oxide (PEO), and at least one additive which has such a solubility that amount of water necessary for dissolving 1 g of the additive is 5 ml or less and which is for causing penetration of water into the preparations. It discloses that since gelation of solid preparations is accelerated, controlled release of the active ingredient becomes possible continuously even in lower alimentary canals in which less water is present. However, it makes no mention of influence given by the difference in molecular weight on strength or dissolution of controlled release solid preparations after gelation. Furthermore, in the dissolution test results disclosed in Examples, dissolution speed decreases in the later period of dissolution, and the problem of decrease in dissolution speed of polymer forming a hydrogel in the later period of dissolution has not yet been solved.

As lipophilic dissolution-controlling base substances, there have been used glycerides such as hydrogenated castor oil, stearic acid glyceride and palmitic acid gryceride, higher alcohols such as cetyl alcohol, fatty acids such as stearic acid, and fatty acid esters such as propylene glycol monostearate. However, these dissolution-controlling base substances have many problems that they lack storage stability, dissolution of active ingredient greatly changes, and dissolution speed of active ingredient decreases in the later period of dissolution.

As the inert dissolution-controlling base substances, there are known polyvinyl chloride, polyethylene, vinyl acetate/vinyl chloride copolymers, polymethyl methacrylate, polyamides, silicone, ethyl cellulose, polystyrene, etc. However, controlled release solid preparations using inert dissolution-controlling base substances develop controlled release due to diffusion of active ingredient through pores formed by compression molding of water-insoluble particles, and hence there is a problem that dissolution speed of active ingredient also changes when size of the pores changes by compression molding pressure. There is another problem that diffusion distance of active ingredient increases in the latter half period of dissolution to result in decrease of dissolution speed.

Patent Documents 13, 14, etc. disclose methods for adjustment of dissolution by adding a water-soluble ingredient to the inert dissolution controlling base substance. Patent Document 13, etc. disclose controlled release solid preparations containing a methacrylic acid copolymer as a dissolution-controlling base substance and an excipient such as D-sorbitol, powdery reduced maltose syrup or anhydrous calcium phosphate. It discloses that by using the solid preparations, dissolution of active ingredient is proportioned to time and does not depend on compressive force. However, in the dissolution test results disclosed in Examples, dissolution speed decreases in the later period of dissolution, and the problem of decrease in dissolution speed of methacrylic acid copolymer in the later period of dissolution has not been solved. Moreover, change in dissolution speed caused by compression molding pressure is not inhibited. The methacrylic acid copolymer commercially available as medicine additives is apt to generate static electricity and besides has a peculiar strong offensive odor, causing problem in handling.

Patent Document 14 discloses a method for increasing or decreasing the releasing rate by adding water-soluble, water-soluble and highly swelling or lipophilic excipient such as polyethylene glycol for changing release to controlled release solid preparations containing a mixture of polyvinyl acetate and polyvinyl pyrrolidone as a dissolution-controlling base substance. This method totally controls dissolution of active ingredient by controlling water permeability through pores formed by compression molding of polyvinyl chloride. However, the problem of decrease in dissolution speed in the later period of dissolution has not been solved. It further discloses that gel is formed on the surface of tablet to inhibit initial dissolution, and hence the dissolution occurs linearly. However, the problem of decrease in dissolution speed in the later period of dissolution cannot be solved, and does not specifically mention use of polyethylene glycol or linear dissolution in Examples. Furthermore, the mixture of polyvinyl acetate and polyvinyl pyrrolidone commercially available as an additive to medicines has strongly yellowish color and strong offensive odor peculiar to chemical synthetic products.

Patent Document 15 discloses a modified starch of 400% or more in water retaining capacity, 5 hours or more in disintegration time and 200 g or more in gel indentation load, and controlled release solid preparations having the modified starch as a dissolution-controlling base substance. It discloses that the above modified starch has a high resistance to α-amylase which is not seen in conventional natural modified starch, and hence shows sufficient controlled release and is not affected by ionic strength, and, therefore, there is no problem of dose dumping and controlled release of active ingredient can be relatively stably performed. In addition, it is produced only by physical processing of starch material in nature. Therefore, the starch has no problem of remaining chemical substances and can be taken without anxiety, and besides is satisfactory in both the flowability and whiteness. However, the modified starch disclosed is relatively high in swelling of particles, and has defects that strength of gelling solid preparation is low, and dissolution speed of active ingredient changes by the compression molding pressure. Moreover, the dissolution of active ingredient greatly changes with changing of compression molding pressure in production process or changing of formulation and amount. Therefore, the dissolution cannot necessarily be accurately controlled. Moreover, if an active ingredient low in solubility in water is used, cracking or breaking in two occurs in solid preparation during unspecified period in the course of dissolution, particularly, under the condition of small compressive force in compression molding, and as a result, dissolution speed is temporarily increased. Further, in the case of a formulation in which content of active ingredient is high, the content of modified starch is restricted to small level. Therefore, the gel layer formed on the solid preparation is relatively low in strength, and tablets are cracked or broken due to the swelling force of solid preparation per se caused by swelling of the modified starch. As a result, there is the problem that a large amount of active ingredient is abruptly released. Thus, the modified starch disclosed in Patent Document 15 can accurately control the dissolution independently of the environments in living organisms such as ionic strength and pH, while it has the problems that dissolution speed changes depending on compression molding pressure, and a large amount of the active ingredient is abruptly dissolved and released in unspecified period depending on the kind and content of the active ingredient.

Use of starches as dissolution-controlling base substance is disclosed in Patent Documents 16-22, etc. Patent Document 16 discloses a pharmaceutical composition containing pregelatinized starch having low viscosity and a particle size of multimode for the purpose of improving variation of dissolution speed of active ingredient. It is disclosed that this composition can be used in many modes including continuous release. However, Examples disclose only such preparations as high in dissolution speed of 75% or more in 45 minutes, and make no specific disclosures indicating controlled slow release. Furthermore, Patent Document 16 differs from the present invention mentioned hereinafter because it does not mention that starch per se has controlled releasing function.

Patent Document 17 discloses controlled release preparations having previously gelatinized starch as a matrix base substance. However, as a preferable embodiment, it discloses use of previously gelatinized corn starch having 10-20% of soluble fraction, which is different from the modified starch used in the present invention which contains 40-95% of a water-soluble ingredient. The dissolution speed of active ingredient is not specifically disclosed. However, the starch of Patent Document 17 which is less in content of ingredient soluble in cold water is insufficient in controlled releasing function, and particularly can hardly control active ingredient having high solubility in water to be slowly released.

Patent Document 18 discloses a matrix controlled release preparation containing at least one of water-soluble polymers and polymers lower in water solubility. Patent Document 19 discloses a matrix controlled release preparation containing both the water-soluble polymer and polymer lower in water solubility. Patent Documents 18 and 19 disclose starch as a water-soluble polymer, but this is different from the modified starch used in the present invention which contains water-soluble ingredient in the range of 40-95% and dissolves only partially in water.

Patent Document 21 discloses a controlled release preparation using as a matrix base substance a starch obtained by applying shear to a mixture of water and 5-95% of starch at a temperature of 130 to 160° C. Patent Document 22 discloses a controlled release preparation using a starch obtained by removing crystallinity of crystalline starch partially or substantially completely. However, in Patent Documents 21 and 22, dissolution of active ingredient cannot be controlled to zero-order dissolution and the like.

Patent Documents 23-25 disclose controlled release preparations using amylose as a matrix base substance, but which are different from the modified starch used in the present invention in that this contains amylose and amylopectin. Patent Documents 26-28 disclose controlled release solid preparations using crosslinked amylose as a matrix base substance. However, the crosslinked amylose is obtained through troublesome steps, namely, by removing amylopectin from natural starch to obtain an amylose and subjecting the amylose to a chemical treatment in the presence of an alkali. Furthermore, when crosslinked amylose is used, it is necessary to add α-amylase as a dissolution speed adjustor to improve dissolution controllability (Patent Document 27) or to use HPMC for lowering dependence on α-amylase present in intestinal environment (Patent Document 28).

Patent Document 29 discloses controlled release preparations using starch acetate as a matrix base substance, Patent Document 30 discloses controlled release preparations using substituted amylase, which is substituted with epoxy group or halogen compound, as a matrix base substance, and Patent Document 31 discloses controlled release preparations using starch modified with carboxylic acid or sulfate as a matrix base substance. Patent Documents 29-31 require chemical treatment in order to impart controlled release function to starch and are different from the present invention in that the modified starch used in the present invention is obtained only by subjecting natural starch to physical treatment.

As mentioned above, in the conventional technologies, there are no controlled release solid preparations which are not affected by environments in living organisms such as ionic strength and pH, compressive force in compression molding, and kind and content of active ingredient, less in change of residence time in gastrointestinal tracts, and can be controlled in dissolution of active ingredient to zero-order dissolution, two or more stage dissolution or timed-dissolution, and such controlled release solid preparations have been desired.

Patent Document 1: U.S. Pat. No. 6,296,873
Patent Document 2: JP-A-2005-504052 (US2004197404)
Patent Document 3: JP-A-2002-525310 (U.S. Pat. No. 6,733, 782)
Patent Document 4: JP-A-2004-107351 (U.S. Pat. No. 5,549, 913)
Patent Document 5: JP-B-51516
Patent Document 6: JP-B-7-8809
Patent Document 7: JP-A-62-149632
Patent Document 8: JP-A-6-172161
Patent Document 9: JP-A-6-305982 Patent Document 10: JP-A-2003-510265 (EP1135106)
Patent Document 11: JP-A-2004-143175 (US2004081693)
Patent Document 12: JP-A-2001-10951
Patent Document 13: JP-A-11-5739
Patent Document 14: JP-A-2002-20319 (US2002012701)
Patent Document 15: WO2005/005484A
Patent Document 16: JP-A-2006-514687 (EP1536788)
Patent Document 17: JP-A-5-262649
Patent Document 18: JP-A-63-54319
Patent Document 19: JP-A-2-209
Patent Document 20: JP-A-63-503225
Patent Document 21: WO92/15285
Patent Document 22: JP-A-61-5027
Patent Document 23: JP-A-2000-517351 (US2002192291)
Patent Document 24: WO99/009066
Patent Document 25: JP-A-2002-363106
Patent Document 26: U.S. Pat. No. 5,456,921 (U.S. Pat. No. 5,456,921)
Patent Document 27: JP-A-8-502036 (EP0651634)
Patent Document 28: JP-A-2000-507561 (U.S. Pat. No. 5,885,615)
Patent Document 29: JP-A-10-502056 (U.S. Pat. No. 5,667, 803)
Patent Document 30: JP-A-2001-502700 (U.S. Pat. No. 5,879,707)
Patent Document 31: WO2005/74976A
Non-Patent Document: Chem. Pharm. Bull. 35(10), 4346-4350 (1987)

DISCLOSURE OF INVENTION

Problem to be Solved by the Invention

Under the circumstances, the object of the present invention is to provide a controlled release solid preparation which is not affected by environments in living organisms such as ionic strength and pH, compressive force in compression molding, and kind and content of active ingredient, less in change of residence time in gastrointestinal tracts, and can be controlled in dissolution of active ingredient to zero-order dissolution, two or more stage dissolution or timed-dissolution.

Means for Solving the Problem

The inventors have conducted intensive research on gel formation mechanism and active ingredient dissolution mechanism of a controlled release solid preparation containing as a dissolution-controlling base substance a modified starch having a moisture retaining capacity of 400% or more and a gel indentation load of 200 g or more. As a result, preferred characteristics which can solve the above problems can be obtained by crushing starch particles having outer shell structure of the modified starch and adjusting them to have a specific particle size. Thus, the present invention has been accomplished.

That is, the present invention is as shown below.

(1) A solid preparation which comprises at least one active ingredient and at least one dissolution-controlling base substance and is obtained by compression molding, wherein the dissolution-controlling base substance contains 5.0-99.9% by weight of a modified starch having a moisture retaining capacity of 400% or more and a gel indentation load of 200 g or more, containing a water-soluble ingredient in an amount of 40-95% by weight, having particles passing through a 75 μm-mesh sieve in the proportion of 90% by weight or more and particles passing through a 32 μm-mesh sieve in the proportion of 20% by weight or more, and having an average particle diameter of not smaller than 20 μm and smaller than 50 μm.

(2) The solid preparation described in (1), wherein the modified starch has particles passing through a 75 μm-mesh sieve in the proportion of 98% by weight or more and particles passing through a 32 μm-mesh sieve in the proportion of 40% by weight or more.

(3) The solid preparation described in (1) or (2), wherein the modified starch has a swelling degree of 6-10 $cm^3/g$.

(4) The solid preparation described in any one of (1)-(3), wherein the modified starch has an angle of repose of 45° or smaller and a specific volume of 1.4 $cm^3/g$ or more.

(5) The solid preparation described in any one of (1)-(4), wherein the dissolution-controlling base substance further contains a hydrophilic polymer assistant and the weight ratio of the modified starch to the hydrophilic polymer assistant is in the range of 50:50-99.9:0.1.

(6) The solid preparation described in (5), wherein the hydrophilic polymer assistant is a synthetic or natural polymer having a solubility in water of 0.1-5.0 $g/cm^3$ at 20° C., a melting point of 50° C. or higher, and a molecular weight of 5000 or more.

(7) The solid preparation described in (5) or (6), wherein the hydrophilic polymer assistant is polyethylene glycol.

(8) The solid preparation described in any one of (1)-(7) which further contains a hydrophilic assistant having a solubility in water of 0.1-5.0 $g/cm^3$, and a molecular weight of 1000 or less.

(9) The solid preparation described in (8), wherein the hydrophilic assistant is at least one member selected from the group consisting of sugar-alcohols, sugars, surface active agents, salts, organic acids, amino acids, and amino sugars.

(10) The solid preparation described in (8) or (9), wherein the hydrophilic assistant is selected from sorbitol and/or sucrose.

(11) The solid preparation described in any one of (1)-(10), wherein a difference between a dissolution rate obtained from a dissolution test conducted using as a test solution the second solution specified in the Japanese pharmacopeia and a dissolution rate obtained from a dissolution test conducted using as a test solution the Mcilvaine solution is 7% or less, and a difference between a dissolution rate obtained from a dissolution test on a solid preparation molded under a pressure of 120 MPa in compression molding and a dissolution rate obtained from a dissolution test of a solid preparation molded under a pressure of 300 MPa in compression molding is 7% or less.

(12) The solid preparation described in any one of (1)-(11), wherein a swelling degree in compression direction in compression molding is 1.0-2.0 and a ratio of swelling degree obtained by dividing the swelling degree in the compression direction by a swelling degree in a direction perpendicular to the compression direction is 0.5-1.5.

(13) The solid preparation described in any one of (1)-(12), wherein the at least one active ingredient is a pharmaceutical active ingredient.

(14) The solid preparation described in any one of (1)-(13) which is a layered tablet comprising two layers which are at least superposed on each other, wherein (a) a first layer contains the active ingredient, (b) a second layer is disposed in contact with the first layer, and (c) one or both of the first and second layers contain the dissolution-controlling base substance.

(15) The solid preparation described in (14), wherein the second layer further contains the active ingredient.

(16) The solid preparation described in (14) or (15), wherein the first layer has upper surface and bottom surface, and only one of the upper surface and the bottom surface contacts with the second layer.

(17) The solid preparation described in (14) or (15), wherein the first layer and the second layer are disposed concentrically, and the first layer constitutes an inner layer and the second layer constitutes an outer layer.

(18) The solid preparation described in any one of (1)-(17) which further contains coating granules.

(19) The solid preparation described in any one of (1)-(18) which additionally contains a lubricant comprising a combination of at least one member selected from the group consisting of a sucrose fatty acid ester, talc and light silicic acid anhydride with magnesium metasilicate aluminate.

(20) The solid preparation described in any one of (1)-(19) which has a weight of 0.2 g or more.

(21) A solid preparation according to any one of (1)-(20), wherein the modified starch is produced by a method which comprises steps of heating a starchy raw material at 60° C. or higher and lower than 100° C. in the presence of water to swell starch particles of the starchy raw material, drying the swollen starch particles to obtain a powder mixture containing starch particles and amylose and amylopectin present outside the starch particles, and grinding the resulting dry powder to adjust the article size.

(22) A solid preparation according to any one of (1)-(20), wherein the modified starch is produced by a method which comprises steps of heat treating a starchy raw material at 100-130° C. under reduced pressure, and further heating the starchy raw material at 60-150° C. in the presence of water to swell starch particles of the starchy raw material, drying the swollen starch particles to obtain a powder mixture containing starch particles and amylose and amylopectin present outside the starch particles, and grinding the resulting dry powder to adjust the particle size.

(23) The solid preparation according to (21) or (22), wherein the starchy raw material is potato starch.

Advantages of the Invention

According to the present invention, there can be provided a controlled release solid preparation which is not affected by environments in living organisms such as ionic strength and pH, compressive force in compression molding, and kind and content of active ingredient, less in change of residence time in gastrointestinal tracts, and can be controlled in dissolution of active ingredient to zero-order dissolution, two or more stage dissolution or timed-dissolution.

BRIEF DESCRIPTION OF THE DRAWINGS

FIG. 7 Results of dissolution test on tablets A-1, A-2 obtained in Example 1.

FIG. 8 Results of dissolution test on tablet A-3 obtained in Example 1 and tablet M-3 obtained in Comparative Example 6.

FIG. 13 Results of dissolution test on tablets H-1, H-2 obtained in Comparative Example 1.

FIG. 14 Results of dissolution test on tablets I-1, I-2 obtained in Comparative Example 2.

FIG. 15 Results of dissolution test on tablets J-1, J-2 obtained in Comparative Example 3.

FIG. 16 Results of dissolution test on tablets M-1, M-2 obtained in Comparative Example 6.

FIG. 17 Results of dissolution test on tablets N-1, N-2 obtained in Comparative Example 7.

FIG. 18 Results of dissolution test on tablets O-1, O-2 obtained in Comparative Example 8.

FIG. 19 Results of dissolution test on tablets P-1, P-2 obtained in Comparative Example 9.

FIG. 20 Results of dissolution test on tablets Q-1, Q-2 obtained in Comparative Example 10.

FIG. 21 Results of dissolution test on tablets R-1, R-2 obtained in Comparative Example 11.

FIG. 22 Results of dissolution test on tablets S-1, S-2 obtained in Comparative Example 12.

BEST MODE FOR CARRYING OUT THE INVENTION

Figure 1:
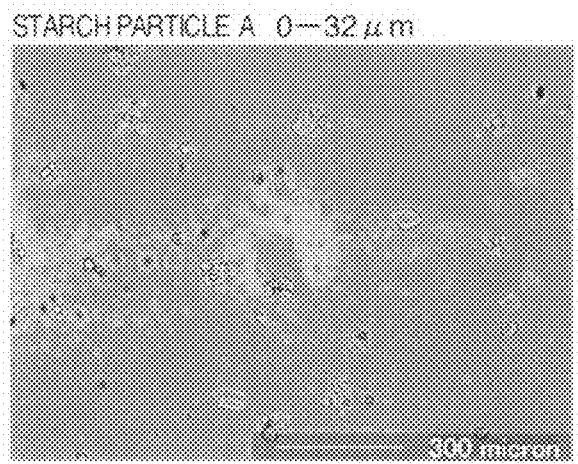
FIG. 1 Optical microscope photograph of particles in 0-32 μm fraction of modified starch A after swollen which was obtained in Example 1.

The present invention will be explained in more detail. It is necessary that the controlled release solid preparation of the present invention contains a modified starch having a moisture retaining capacity of 400% or more and a gel indentation load of 200 g or more, containing a water-soluble ingredient in an amount of 40-95% by weight, having particles passing through a 75 μm-mesh sieve in the proportion of 90% by weight or more and particles passing through a 32 μm-mesh sieve in the proportion of 20% by weight or more, and having an average particle diameter of not smaller than 20 μm and smaller than 50 μm. This specific modified starch functions as a dissolution-controlling base substance to secure the controlled release of active ingredient. The modified starch used in the present invention is a starch obtained by modifying a starchy material only by physical treatment.

First, the specific modified starch having the above characteristics will be explained. It is necessary that the content of the specific modified starch in the solid preparation is 5.0-99.9% by weight. When the content of the modified starch is 5% or more, controlled release of active ingredient can be easily attained. The optimum content of the modified starch can be optionally selected depending the kind and amount of active ingredient, but if the content of the modified starch is more than 99.9% by weight, the content of the active ingredient decreases and sufficient pharmaceutical efficacy can hardly be obtained. Thus, the upper limit is preferably 99.9% by weight. The content is more preferably 10-99.9% by weight, especially preferably 20-99.9% by weight.

It is necessary that the modified starch has a moisture retaining capacity of 400% or more. The moisture retaining capacity is more preferably 500% or more, most preferably 700% or more. The moisture retaining capacity here is defined to be an amount of pure water retained by the starch after 1 g of dry modified starch is dispersed in pure water of 20° C.±5° C. and the dispersion is centrifuged (2000G, 10 minutes). The modified starch is hydrated at a moisture retaining capacity of 400% or more to form gel, and hence the solid preparation is hardly disintegrated, and diffusion rate of active ingredient is kept and sufficient controlled release can be easily developed. The higher moisture retaining capacity gives the higher gel formability, and gel is not broken even under a high ionic strength, but the maximum value depends on the characteristics of starch raw material and is at most 3000%.

It is necessary that the specific modified starch has a gel indentation load of 200 g or more. The gel indentation load is defined to be a maximum load when a columnar molded product having a diameter of 1.13 cm obtained by compressing 0.5 g of modified starch under 50 MPa is immersed in pure water at 20° C.±5° C. for 4 hours to cause gelation of the molded product, and then a columnar adapter having a diameter of 3 mm is indented into the gel at a rate of 0.1 mm/sec. The maximum load here is a load at breaking in case the gel layer is broken, and is a maximum load shown until the adapter penetrates by 5 mm into the gelling columnar molded product in case the gel layer is not broken. When the gel indentation load is 200 g or more, the diffusion of active ingredient in the gel layer formed by the modified starch is not too fast, resulting in development of sufficient controlled release. The higher gel indentation load gives the higher controlled releasing ability and is preferred, but is at most about 3000 g.

Furthermore, it is necessary that the amount of a water-soluble ingredient contained in the specific modified starch is in the range of 40-95% by weight. The amount of water-soluble ingredient is defined to be a value obtained by the following calculation. That is, 99 g of pure water of 20° C.±5° C. is added to 1 g of the modified starch, followed by stirring with a magnetic stirrer for 2 hours to disperse the starch; 40 cm³ of the resulting dispersion is transferred to a centrifugal settling tube of 50 cm³, and centrifuged at 5000G for 15 minutes; 30 cm³ of the supernatant liquid is put in a weighing bottle; the liquid is dried at 110° C. until the weight reaches a given value, and dry weight (g) of the water-soluble ingredient is obtained. Furthermore, 1 g of modified starch is dried at 110° C. until the weight reaches a given value and an absolute dry weight (g) of the modified starch is obtained. Thus, the amount of water-soluble ingredient is defined to be a value obtained by the following formula (1) using the values obtained above.

$$\text{Amount of water-soluble ingredient(\% by weight)} = (\text{dry weight (g)} \times 100 \div 30) \div \text{absolute dry weight (g) of 1 g of starch} \times 100 \quad (1)$$

The amount of the water-soluble ingredient is a value which indicates an amount of a paste component obtained by gelatinization of the modified starch and made water-soluble by a heat treatment. When the water-soluble ingredient is 40% by weight or more, hydration rate is secured and is not too slow, and there hardly occurs such a phenomenon that the controlled release solid preparation releases a large amount of active ingredient immediately after contacting with solvent. When the amount of water-soluble ingredient is 95% by weight or less, strength of the solid preparation is secured and sufficiently controlled release can be easily obtained. Furthermore, the solid preparation can stand against mechanical movement of gastrointestinal tracts and hence is not excessively eroded to secure the dissolution rate in a certain range.

Furthermore, it is necessary that the specific modified starch has particles passing through a 75 μm-mesh sieve in the proportion of 90% by weight or more and particles passing through a 32 μm-mesh sieve in the proportion of 20% by weight or more, and having an average particle diameter of not smaller than 20 μm and smaller than 50 μm. Preferably, the starch has particles passing through a 75 μm-mesh sieve in the proportion of 95% by weight or more and particles passing through a 32 μm-mesh sieve in the proportion of 30% by weight or more, and particularly preferably, the starch has particles passing through a 75 μm-mesh sieve in the proportion of 98% by weight or more and particles passing through a 32 μm-mesh sieve in the proportion of 40% by weight or more. The specific modified starch having smaller particle size is lower in swelling and higher in gel strength. Therefore, when the specific modified starch has particles passing through a 75 μm-mesh sieve in the proportion of 90% by weight or more and particles passing through a 32 μm-mesh sieve in the proportion of 20% by weight or more, and having an average particle diameter of smaller than 50 μm, the swelling of the starch particles and the solid preparation comprising the starch particles remains in relatively small range. Furthermore, dissolution of active ingredient from the solid preparation hardly changes by the compression molding pressure.

Moreover, it is preferred that the specific modified starch has a swelling degree of 6-10 cm³/g. The swelling degree of modified starch is defined to be a value obtained in the following manner. That is, 1.0 g of modified starch is dispersed in pure water of 20° C.±5° C., the dispersion is transferred to a settling tube of 100 cm³, 100 cm³ in total amount of the dispersion is left to stand for 16 hours, and thereafter, volume V (cm³) of the lower layer of the upper and lower separating layers and dry weight (g) of 1.0 g of the modified starch are measured. The value of swelling degree is obtained by the following formula (2).

$$\text{Swelling degree of modified starch (cm}^3\text{/g)} = V \text{ (cm}^3\text{)} / \text{dry weight (g) of modified starch} \quad (2)$$

When the swelling degree of modified starch is 6 cm³/g or more, since the starch is hydrated to form gel, controlled release of active ingredient can be easily attained. On the other hand, if the swelling degree of modified starch exceeds 10 cm³/g, the solid preparation is swollen due to swelling of the modified starch. As a result, dissolution rate of active ingredient decreases or the solid preparation is disintegrated owing to the swelling force, resulting in dose dumping. When the swelling degree of the modified starch is in the range of 6-10 cm³/g, controlled slow release of active ingredient can be stably performed, which is preferred.

The specific modified starch preferably has an angle of repose of 45° or smaller. The more preferred angle of repose is 43° or smaller. Moreover, the specific modified starch preferably has a specific volume of 1.4-3.3 cm³/g. The specific modified starch having an angle of repose of 45° or smaller and a specific volume of 1.4-3.6 cm³/g is superior in mixability and dispersibility with active ingredient, and hence can form a uniform gel matrix to result in stable controlled release, which is preferred.

A method for producing modified starch having a moisture retaining capacity of 400% or more, a gel indentation load of 200 g or more, and containing a water-soluble ingredient in an amount of 40-95% by weight is disclosed in Patent Document 15. The inventors have conducted detailed investigation on the modified starch obtained by the method disclosed in Patent Document 15. As a result, the inventors have found that swellability and gel indentation load differ depending peculiarly on particle size, and a controlled release solid preparation which does not depend on compression molding pressure can be obtained only by controlling the particle size and swellability of the modified starch to proper ranges. The process of the investigation will be explained below.

The inventors firstly produced conventional modified starch C by a method in accordance with the method of Patent Document 15, specifically, in the manner as mentioned in Comparative Example 2 given hereinafter. The resulting modified starches C were fractionated in accordance with particle sizes of 0-32, 32-75, 75-150, and 150-500 μm, and basic physical properties of them were compared. Table 1 shows particle size distribution, swelling degree and gel indentation load under the conditions of storage with heating of the resulting modified starches C, and FIG. 3-FIG. 6 show light microscope photographs of particles after modified starch C was swollen.

Here, the gel indentation load under the conditions of storage with heating shown in Table 1 is a value obtained in the following manner. That is, a columnar molded product having a diameter of 1.13 cm obtained by compressing 0.5 g of modified starch under 50 MPa is immersed in pure water at 37° C.±0.5° C. for 4 hours to cause gelation of the molded product, and then a columnar adapter having a diameter of 3 mm is indented into the gel at a rate of 0.1 mm/sec, and the value at which a peak is firstly given is employed as the desired gel indentation load. The swelling degree of modified starch shown in Table 1 is a value obtained by the same method as aforementioned.

From the data of modified starch C in Table 1 and photographs of swollen particles in FIG. 3-FIG. 6, it can be seen that the modified starch particles of the fraction of 0-32 μm have a swelling degree of about 14 and a size of swollen particles of about 100 μm, and thus they are small in swellability and have a large gel indentation load of about 300 g. On the other hand, it can be seen that the modified starch particles of particle size fractions of 32-75, 75-150 and 150-500 μm have a swelling degree of 20-30 and a size of swollen particles of 200-300 μm, and thus they are large in swellability and have a small gel indentation load of about 200 g. Moreover, the swollen modified starch particles of fractions of 32-75 μm and those of 75-150 and 150-500 μm have the same size, and swellability of the modified starch correlates with the size of particles before swollen. From these facts, it can be seen that the component of the swelling starch particles having outer shell structure included in the modified starch particles in the range of 75-500 μm is the same as of the swelling starch particles having outer shell structure in the fraction of 32-75 μm, and the starch particles are granulated to large modified starch particles of 75-500 μm with water-soluble paste component (not observed by a light microscope because they are swollen and dissolved to lose their contours).

From these facts, it is clear that the modified starch obtained by the method of Patent Document 15 comprises three components of a starch particle group of 0-32 μm fraction which has outer shell structure of starch particles and is small in swelling and large in gel indentation load, a starch particle group of 32-75 μm fraction which has outer shell structure and is large in swelling and small in gel indentation load, and a water-soluble paste component, and these three components are granulated to form modified starch having a particle size distribution in 0- about 500 μm. These facts cannot be recognized only from appearance of the modified starch because the surface of all the particles are covered with water-soluble component.

Further, the modified starches are fractionated into those of 0-32 μm fraction small in swelling and large in gel indentation load and those of 32-500 μm fraction large in swelling and small in gel indentation load, and controlled release solid preparations are produced using the respective fractions. As a result, the solid preparation obtained from the 0-32 μm fraction shows accurate and stable dissolution which does not depend on compressive force. On the other hand, it becomes clear that the solid preparation obtained from the 32-500 μm fraction shows larger swelling in the compression direction with decrease of compressive force, which causes increase in dissolution speed of active ingredient and decrease in strength of gelling solid preparation. That is, it becomes clear that the characteristics of the resulting solid preparations change at a border of the particle diameter of 32 μm. It is confirmed that for obtaining controlled release solid preparation which does not depends on compression molding pressure, it is preferred to use particles small in swelling and high in gel strength such as of 0-32 μm fraction. It is considered that this is because disintegration force inside the solid preparation can be suppressed due to the small swelling of modified starch particles.

In view of the above facts, the inventors have considered that when starch particles having outer shell structure of 32-75 μm present in the particles of 32-500 μm are crushed, the modified starch can be made smaller in swelling, and as a result, controlled release solid preparations which do not depend on compressive force can be obtained. As a result of repeating investigations on various crushing conditions, it has been found that modified starch similarly small in swelling and large in gel indentation load can be obtained by controlling the particle size distribution so that particles passing through a 75 μm-mesh sieve are in the proportion of 90% by weight or more and particles passing through a 32 μm-mesh sieve are in the proportion of 20% by weight or more, and the average particle diameter is not smaller than 20 μm and smaller than 50 μm. In this way, controlled release solid preparations which do not depend on compressive force can be obtained by controlling the particle size distribution of the modified starch.

Figure 2:
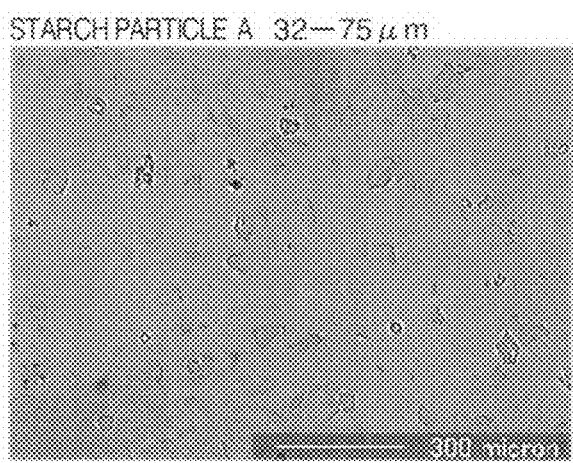
FIG. 2 Optical microscope photograph of particles in 32-75 μm fraction of modified starch A after swollen which was obtained in Example 1.
Figure 3:
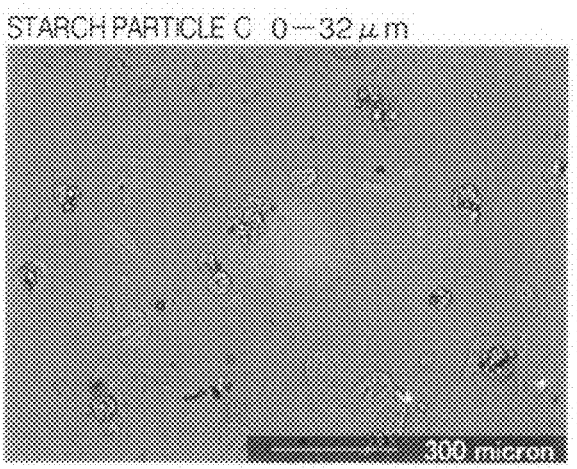
FIG. 3 Optical microscope photograph of particles in 0-32 μm fraction of modified starch C after swollen which was obtained in Comparative Example 2.
Figure 4:
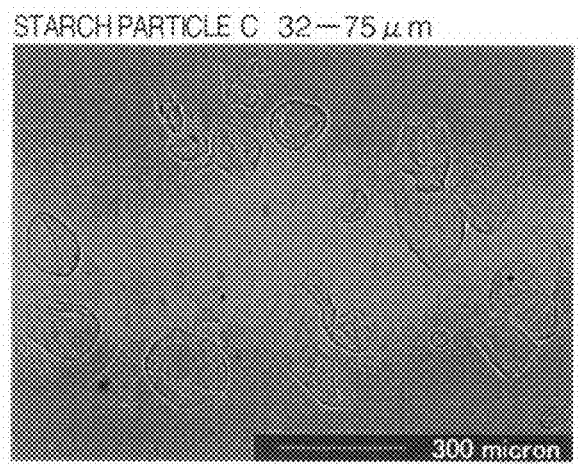
FIG. 4 Optical microscope photograph of particles in 32-75 μm fraction of modified starch C after swollen which was obtained in Comparative Example 2.
Figure 5:
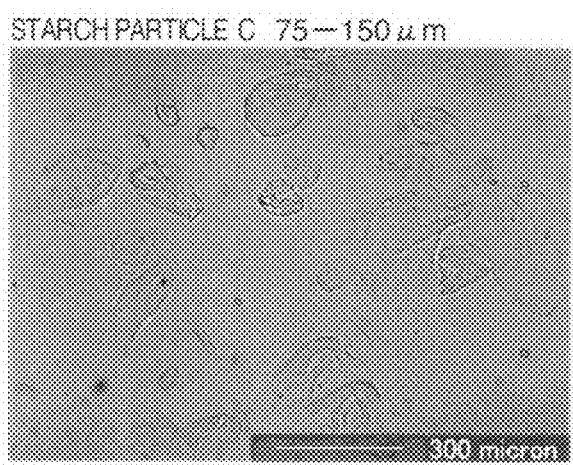
FIG. 5 Optical microscope photograph of particles in 75-150 μm fraction of modified starch C after swollen which was obtained in Comparative Example 2.
Figure 6:
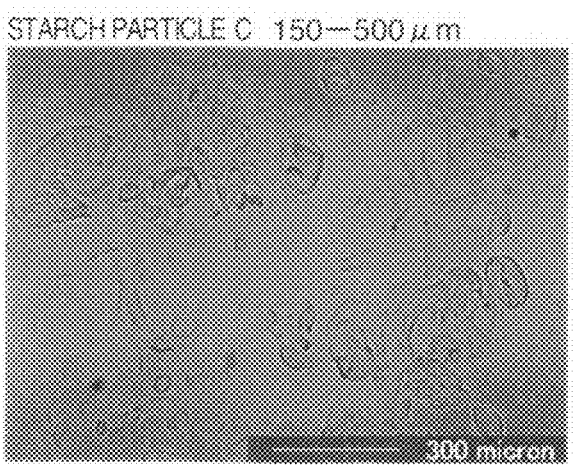
FIG. 6 Optical microscope photograph of particles in 150-500 μm fraction of modified starch C after swollen which was obtained in Comparative Example 2.

Here, modified starch A obtained in Example 1 which has particles passing through a 75 μm-mesh sieve in the proportion of 90% by weight or more and particles passing through a 32 μm-mesh sieve in the proportion of 20% by weight or more, and an average particle diameter is not smaller than 20 μm and smaller than 50 μm is fractionated in particle size of 0-32, 32-75 μm, and basic physical properties of the particles of each fraction are compared. Table 1 shows particle size distribution, swelling degree and gel indentation load under the condition of storage with heating of the whole particles of the modified starch A and the particles of each fraction. Furthermore, FIG. 1 and FIG. 2 show light microscope photographs of swollen particles after the particles of each fraction are swollen. It can be confirmed that primary particles having outer shell structure of the modified starch are broken. It is further confirmed that all of the fractionated particles of 0-32 μm and 32-75 μm are small in swelling and large in gel indentation load.

Next, the method for producing the specific modified starch mentioned above will be explained. The specific modified starch is produced, for example, through a step of heating a starchy raw material at 60° C. or higher and lower than 100° C. in the presence of water to swell starch particles of the starchy raw material; a step of drying the swollen starch particles to obtain powders of a mixture containing starch particles and amylose and amylopectin present on the outside of the starch particles; and grinding the resulting dried powders to adjust the particle size. Alternatively, it is produced through a step of heat treating a starchy raw material at 100-130° C. under reduced pressure and further heating the starchy raw material at 60-150° C. in the presence of water to swell the starch particles of the starchy raw material; a step of drying the swollen starch particles to obtain powders of a mixture containing starch particles and amylose and amylopectin present on the outside of the starch particles; and grinding the resulting dried powders to adjust the particle size. The amylose and amylopectin present outside the starch particles are amylose and amylopectin dissolved out of the starch particles and originating from starch whose outer shell structure is broken by swelling with heat treatment. The term "in the presence of water" for the starchy raw material means a state of the starchy raw material and water being present, with the amount of water being 40% by weight or more.

Starchy raw materials usable in the production include natural starches such as of rice, glutinous rice, maize, waxy maize, amylocorn, sorghum, wheat, barley, taro, green gram, potato, lily, dogtooth violet, tulip, canna, pea, snow pea, Japanese chestnut, arrowroot, yam, sweet potato, broad bean, kidney bean, sago, tapioca (cassava), bracken, lotus, and water caltrop, retrograded starches, crosslinked starches, etc. There is no particular limitation so long as they contain starchy material, and potato is preferred from the viewpoints of high swelling of particles and easy control to high moisture retaining capacity. The starchy raw materials may be used each alone or in admixture of two or more. The starchy raw materials large in size are preferred from the point of easiness in swelling.

The starchy raw materials subjected to a wet heat treatment such as heat treatment at 100-130° C. under reduced pressure as disclosed in JP-A-4-130102 and JP-A-7-25902 are more preferred because gelatinization starting temperature rises and swelling of particles increases.

For example, JP-A-4-130102 discloses (1) a method of wet heat treatment which comprises putting starch in a closable vessel which is pressure-resistant against both internal pressure and external pressure provided with both a pressure reducing line and a pressurized steam line, reducing the pressure, and then carrying out pressurizing with heating by introduction of steam or repeating this procedure to heat starch for a given time, and then cooling the starch; (2) a method of wet heat treatment to produce starch which shows swelling of starch particles, but substantially no viscosity when a water suspension is heated and which is very high in α-amylase adsorbability by setting the vessel temperature at 120° C. or higher in addition to the method (1); (3) a method of wet heat treatment which carries out cooling under reduced pressure after heating in addition to the method (1) or (2). Any of these methods of wet heat treatment may be employed.

JP-A-7-25902 discloses (4) a method for producing wet heat treated starchy grains by subjecting starchy grains to wet heat treatment which comprises repeating at least one time a first step of subjecting starchy grains filled in a pressure resistant vessel to reduction of pressure and a second step of introducing steam after reduction of pressure to heat and pressurize the starchy grains; (5) a method of production where the heating in the second step of the method (4) is carried out at 80° C. or higher for 5 minutes to 5 hours. Any of these methods may be employed.

The starch obtained by subjecting starchy raw material to wet heat treatment under reduced pressure by these methods is in the form of hollow particles having outer shell part increased in crystallinity due to heating at high temperatures. Such starch has the features that the cross polarization pattern seen in polarization image of light microscope is weaker than that of green starch and non-birefringent particles diminish. Furthermore, it is considered that the hollow portion has such a structure as crystal state of amylose or amylopectin being loosened, and the starch has the feature that the digestibility of the starch with α-amylase increases than that of green starch. Thus, it is suitable to be used as the specific modified starch.

Moreover, it is preferred that in the course of heating the starch emulsion to 50-95° C. in wet heat treatment of starchy raw material, viscosity of the starch emulsion is 400 Brabender unit (BU) or less when the emulsion is adjusted to a concentration of 5%, and the maximum viscosity when held at 95° C. for 30 minutes is 1000 BU or less. This is because the degree of swelling the starch particles by heat treatment can be easily adjusted.

The method of heating the starchy raw material is not particularly limited as far as it is a known method. For example, mention may be made of a method of heating the starchy raw material in the presence of water by putting it in a reactor with jacket and introducing steam into the jacket; a method of mixing the starchy raw material in the presence of water with steam; a method of heating with a liquid reservoir of a drum dryer; and a method of simultaneously carrying out gelatinization and spraying while supplying steam to starch slurry during spray drying. From the viewpoint of heating time of starch particles, the method of mixing the starchy raw material in the presence of water with steam is preferred. The heating temperature may be such that the liquid temperature after gelatinization of starch by the above various methods is 90-150° C., preferably 90-130° C., more preferably 95-130° C.

The drying method is not particularly limited, and mention may be made of, for example, freeze drying, spray drying, drum drying, tray drying, airborne drying, vacuum drying and drying by solvent replacement. Industrially, spray drying and drum drying are preferred. The solid content in liquid at drying is preferably about 0.5-60% by weight. When it is 0.5% by weight or more, productivity becomes higher, and when it is 60% by weight or less, the viscosity does not increase excessively and yield is secured, which is preferred. It is more preferably 1-30% by weight, especially preferably 1-20% by weight.

The grinding method is not particularly limited, and there may be employed, for example, cone crusher, double-roll crusher, hammer mill, ball mill, rod mill, pin-type mill, and jet-type mill. For avoiding insufficient grinding or excess grinding, it is preferred to employ closed circuit grinding system provided with the above grinding machine and classifying machine.

The modified starch which has a moisture retaining capacity of 400% or more and a gel indentation load of 200 g or more, and contains a water-soluble ingredient in an amount of 40-95% by weight and which is adjusted in particle size in such a manner that particles passing through a 75 μm-mesh sieve is in the proportion of 90% by weight or more and particles passing through a 32 μm-mesh sieve is in the proportion of 20% by weight or more, and the particles have an average particle diameter of not smaller than 20 μm and smaller than 50 μm has features that it is smaller in swelling degree and higher in gel indentation load than modified starch which is not adjusted in particle size. Moreover, the modified starch preferably has a specific volume in the range of 1.4-3.6 $cm^3/g$, and the specific volume is affected by concentration of liquid in drying step and further by the number of rotation of atomizer in spray drying step. Therefore, the specific volume can be in the above preferred range by suitably adjusting the above values.

The dissolution-controlling base substance used for the solid preparation of the present invention may be used, if necessary, in combination with other dissolution-controlling base substances so long as the effect of the specific modified starch is not damaged. Examples of the other dissolution-controlling base substances are hydrophilic dissolution-controlling base substances (e.g., cellulose derivatives such as methyl cellulose, hydroxypropyl cellulose, hydroxypropylmethyl cellulose and carboxymethyl cellulose, non-cellulose polysaccharides such as xanthan gum and locust bean gum, synthetic polymers such as polyethylene oxide and acrylic acid polymer); lipophilic dissolution-controlling base substances (e.g., hydrogenated castor oil, glycerides such as stearin and palmitin, higher alcohols such as cetyl alcohol, fatty acids such as stearic acid, and fatty acid esters such as propylene glycol monostearate); inert dissolution-controlling base substances (e.g., polyvinyl chloride, polyethylene, vinyl acetate/vinyl chloride copolymer, polymethyl methacrylate, polyamide, silicone, ethyl cellulose, and polystyrene), etc.

Solid preparations in which the above specific modified starches are used as a dissolution-controlling base substance are hardly affected by ionic strength in the body and compression molding pressure, and the swelling of the solid preparations can be suppressed within a low range. Therefore, when such modified starches are used, it is easy to accurately control the active ingredient to be slowly released, which is preferred. Specifically, depending on design of preparations, the solid preparations can be precisely controlled to a pattern of zero-order dissolution of active ingredient or to a pattern of 2 or more stage dissolution or timed-dissolution.

Here, control to the zero-order dissolution means the characteristics that the active ingredient is slowly released from the solid preparation at a certain dissolution rate regardless of time, and the time required for dissolution of 90% or more of the active ingredient is at least 3 hours. The time required for dissolution of 90% or more of the active ingredient can be optionally selected, for example, 8 hours, 12 hours, 24 hours from administration, depending on the kind and purpose of the active ingredient, but the upper limit is 72 hours since there is a limit in residence time of solid preparation in gastrointestinal tracts. For example, when 90% or more of the active ingredient is released in 8 hours, it is preferred to control in such a manner that dissolution rates of the active ingredient after 1 hour, 4 hours and 6 hours measured in accordance with the first method (rotating basket method) of dissolution test methods mentioned in the 14th edition of Japanese pharmacopeia are 10-30%, 40-60% and 70% or more, respectively. Furthermore, for example, when 90% or more of the active ingredient is released in 24 hours, it is preferred to control in such a manner that dissolution rates after 1 hour, 10 hours and 18 hours are 10-30%, 40-60% and 70% or more, respectively. It is possible to control with properly changing the interval of time depending on the time in which the active ingredient is released.

The preferred dissolution pattern in which the dissolution of active ingredient is controlled to zero-order dissolution has a feature that the ratio of an initial dissolution speed to a later dissolution speed is 0.5-1.2 when the dissolution of the active ingredient is evaluated by the ratio of an initial dissolution rate to a later dissolution rate ($M_{70-90\%}/M_{20-40\%}$), namely, the ratio of a dissolution rate (the initial dissolution rate: $M_{20-40\%}$) per unit time in the time zone in which the dissolution rate of the active ingredient is 20-40% to a dissolution rate (the later dissolution rate: $M_{70-90\%}$) per unit time in the time zone in which the dissolution rate of the active ingredient is 70-90%.

The initial dissolution speed and the later dissolution speed are defined to be the values obtained in the following manner. A dissolution test is conducted by the method in accordance with the first method (rotating basket method) of the dissolution test methods mentioned in the 14th edition of Japanese pharmacopeia using a solid preparation having a weight of 0.18 g and a diameter of 0.8 cm and molded using a static pressure press under the compression molding pressure of 120 MPa and 300 MPa. A dissolution test is conducted using either of the second solution mentioned in the 14th edition of Japanese pharmacopeia (pH: 6.8, ionic strength: 0.14, hereinafter sometimes referred to as "the second solution") to which α-amylase is added at a concentration of 5 μg/$cm^3$, and the Mcilvaine solution (pH: 7.2, ionic strength: 0.40, composition: disodium hydrogenphosphate 173.9 mM and citric acid 13.1 mM, hereinafter sometimes referred to as "Mc solution") to which α-amylase is added at a concentration of 5 μg/$cm^3$, under the conditions of using 900 $cm^3$ of either of the solutions, a basket rotation number of 100 rpm and a temperature of the test solution of 37±0.5° C.

At the point of time of 30 minutes elapsing after starting of the test and at every 1 hour elapsing until 90% or more of the active ingredient has been released, the test solution is sampled and dissolution rate of the active ingredient is obtained. From the data obtained, times required for 20, 40, 70 and 90% of the active ingredient to be released are calculated. The time required for releasing 20% of the active ingredient is obtained by the method in which the sampling time before and after the dissolution rate of the active ingredient reaches 20% and the dissolution rate at that time are plotted on a graph and the points are connected with a straight line, and dissolution time corresponding to a dissolution rate of 20% is read as the point on the straight line. Similarly, times required for 40, 70 and 90% of the active ingredient to be released are obtained by the method in which the sampling times before and after the dissolution rate of the active ingredient reaches 40%, 70% and 90% and the dissolution rates at that time are plotted on a graph and the points are connected with a straight line, and the dissolution times corresponding to dissolution rates of 40%, 70% and 90% are read as the points on the straight line. Based on the data obtained as above, the initial dissolution speed: $M_{20-40\%}$ and the later dissolution speed: $M_{70-90\%}$ can be obtained.

To control the release of active ingredient to the release at 2 or more stages means to control the dissolution speed of active ingredient to different 2 or more stages. The dissolution time and dissolution rate at each stage can be suitably adjusted according to the kind of active ingredient and the amount of dissolution-controlling base substance. For example, when the time required for releasing 90% or more of the active ingredient is 8 hours, it is possible to control the active ingredient to be released in a large amount after 5 hours by adjusting the dissolution rate after 5 hours to 40% and the dissolution rate after 8 hours to 90% or more.

To control the release of active ingredient to timed-release means that a given lag time is present between administration and starting of dissolution of active ingredient. The length of the lag time can be controlled by the components of core layer and the content of modified starch in the outer layer, and it is preferred to control the lag time to a range of from 15 minutes to 16 hours depending on the active ingredient. It is preferred that substantially no active ingredient is released during the lag time. The dissolution of active ingredient after elapse of the lag time can be controlled to both the rapid release and the slow release according to the characteristics of active ingredient. By containing modified starch as dissolution-controlling base substance in the core layer, the dissolution of active ingredient after elapse of the lag time can also be made slower.

The solid preparation of the present invention may further contain a hydrophilic polymer assistant in addition to the specific modified starch, and in this case, the weight ratio of the modified starch to the hydrophilic polymer assistant is preferably in the range of 50:50-99.9:0.1. Moreover, the hydrophilic polymer assistant is preferably a synthetic or natural polymer having a solubility in water of 0.1-5.0 g/cm$^3$ at 20° C., a melting point of 50° C. or higher, and a molecular weight of 5000 or more. When the hydrophilic polymer assistant is contained, gelation of the dissolution-controlling base substance dispersed in the surface of the solid preparation is accelerated. Therefore, a gel layer is formed on the surface of the solid preparation more rapidly than the dissolution of the active ingredient dispersed in the surface of the solid preparation to inhibit the active ingredient from being released in a large amount in the initial period of dissolution, and thus control to zero-order dissolution can be made easily, which is preferred. Furthermore, since erosion of the solid preparation increases in the later period of dissolution, control to zero-order dissolution can be made easily without decrease of dissolution speed in the later period of dissolution, which is preferred. The lower limit of solubility of the hydrophilic polymer assistant in water is preferably 0.2 g/cm$^3$, more preferably 0.4 g/cm$^3$. The upper limit of solubility in water is preferably 4.5 g/cm$^3$, more preferably 4.0 g/cm$^3$. When the solubility in water is 0.1 g/cm$^3$ or more, hydration with the dissolution-controlling base substance on the surface of the solid preparation is accelerated to promote gelation. Thus, control of dissolution of active ingredient to zero-order dissolution becomes easier. When the solubility in water is 5.0 g/cm$^3$ or less, increase of penetration of water in the dissolution-controlling base substance is not too large, and gelation occurs in such a range as the gel density being not rough. Therefore, the strength of gel layer hardly becomes too weak, increase of dissolution speed due to excess progress of erosion does not occur in the later period of dissolution, and control of dissolution of active ingredient to zero-order dissolution becomes easier.

The hydrophilic polymer having a solubility in water of 0.1-5.0 g/cm$^3$ is preferably a hydrophilic and relatively high-molecular weight synthetic or natural polymer. Specific examples are polyethylene glycol, polyvinyl pyrrolidone, polyvinyl alcohol, pullulan, etc. Polyethylene glycol is especially preferred.

The solid preparation of the present invention preferably further contains a hydrophilic assistant having a solubility in water of 0.1-5.0 g/cm$^3$ at 20±5° C. and a molecular weight of 1000 or less. By containing the hydrophilic assistant in the dissolution-controlling base substance, water is penetrated into the solid preparation, hydration of the specific modified starch is accelerated, and a dense gel layer can be formed. Therefore, stable release can be attained without being affected by mechanical movement of gastrointestinal tracts, which is preferred. The solubility of the hydrophilic assistant in water is preferably 0.2-5.0 g/cm$^3$, more preferably 0.4-5.0 g/cm$^3$. When the solubility of the hydrophilic assistant in water is 0.1 g/cm$^3$ or more, penetration of water into the solid preparation becomes possible regardless of action of ingredients low in solubility in water which are dispersed in the matrix. As a result, a dense gel layer is formed, and cracking or breaking due to swelling force of the solid preparation per se hardly occurs, which is preferred. Furthermore, when the solubility of the hydrophilic assistant in water is 5.0 g/cm$^3$ or less, water absorption of solid preparation is in a proper range and causes no excess water absorption, and thus strength of the solid penetration is secured, and the solid preparation can stand the load given by mechanical movement of gastrointestinal tracts. Therefore, the dissolution speed can be stably maintained.

The addition of the water-soluble assistant to the solid preparation of the present invention is preferred especially when the solubility of active ingredient in water is in the range of 0.0001-100 mg/cm$^3$. When the solubility of active ingredient in water is in the above range, penetration of water into the solid preparation tends to be slow. In such a case, penetration of water is accelerated and a dense gel layer is formed by adding the hydrophilic assistant. As the active ingredients having a solubility in water of 0.0001-100 mg/cm$^3$, mention may be made of, for example, medicines somewhat easily soluble in water (amount of solvent necessary for dissolving 1 g of solute is 10-30 cm$^3$); medicines somewhat insoluble in water (amount of solvent necessary for dissolving 1 g of solute is 30-100 cm$^3$); medicines difficultly soluble in water (amount of solvent necessary for dissolving 1 g of solute is 100-1000 cm$^3$); medicines very slightly soluble in water (amount of solvent necessary for dissolving 1 g of solute is 1000-10000 cm$^3$); and medicines hardly soluble in water (amount of solvent necessary for dissolving 1 g of solute is 10000 cm$^3$ or more) which are mentioned in the 14th edition of Japanese pharmacopeia in the field of medicines.

The hydrophilic assistants having a solubility in water of 0.1-5.0 g/cm$^3$ and a molecular weight of 1000 or less include, for example, organic materials or inorganic salts which are hydrophilic and relatively low in molecular weight. Specific examples are at least one selected from sugar alcohols such as sorbitol and mannitol; sugars such as white sugar, anhydrous maltose, sucrose, fructose, dextran and glucose; surface active agents such as polyoxyethylene hardened castor oil, polyoxyethylene polyoxypropylene glycol, and polyoxyethylene sorbitan higher fatty acid esters; salts such as sodium chloride and magnesium chloride; organic acids such as citric acid and tartaric acid; amino acids such as glycine and alanine; and amino sugars such as meglumine. Sorbitol, sucrose, etc. are particularly preferred as the hydrophilic assistants.

Furthermore, the solid preparation of the present invention preferably further contains a hydrophobic assistant which has a disintegration time of 8 hours or more, an indentation strength of 2 kg or more and a sedimentation volume of 3 ml or less when dispersed in water. When the hydrophobic assistant is contained in the dissolution-controlling base substance, the specific modified starch and the hydrophobic assistant together form a matrix to give strength to the solid preparation. Thus, stable control of dissolution is possible without depending on the content of active ingredient or compression molding pressure. Use of the hydrophobic assistant in the solid preparation of the present invention is preferred especially when the content of the active ingredient in the solid preparation is high and that of the dissolution-controlling base substance is low. When the content of active ingredient is high and that of dissolution-controlling base substance is low, the gel layer formed on the surface of the solid preparation tends to become weak. In such a case, when the hydrophobic assistant is added, strength of the solid preparation increases, and dissolution speed of active ingredient is stabilized independently of the content of active ingredient and compression molding pressure.

Here, the disintegration time is defined to be a disintegration time in a test solution of a columnar molded product having a diameter of 1.13 mm obtained by molding 0.5 g of a hydrophobic assistant powder under a compression pressure of 50 MPa using a static pressure press (MODEL-1321DW CREEP manufactured by Aiko Engineering Co., Ltd.). The test solution is the second solution mentioned in the 14th edition of Japanese pharmacopeia, and the disintegration test is conducted in accordance with the disintegration test method of the 14th edition of Japanese pharmacopeia using an auxiliary plate. When the disintegration time is 8 hours or more, desirable strength is given to the solid preparation.

The indentation strength is defined as follows. A columnar molded product having a diameter of 1.13 mm obtained by molding 0.5 g of a hydrophobic assistant powder under a compressive force of 50 MPa using a static pressure press (MODEL-1321DW CREEP manufactured by Aiko Engineering Co., Ltd.) is immersed in pure water at 20° C.±0.5° C. for 4 hours. Then, a columnar adapter having a diameter of 3 mm is indented into the molded product at a rate of 0.1 mm/sec using a rheometer (RHEONER RE-33005 manufactured by YMMADEN Co.). The maximum load at indentation is defined to be the indentation strength. The maximum load is a load at breaking of the molded product in case the molded product is broken, and is a maximum load shown until the adapter is penetrated by 5 mm into the columnar molded product in case the molded product is not broken. This is calculated as an average value of five values obtained. When this indentation strength is 2 kg or more, a desired strength is given to the solid preparation.

The sedimentation volume when the solid preparation is dispersed in water is measured by dispersing 1.0 g of a dried hydrophobic assistant powder in pure water at 20° C.±0.5° C., transferring the dispersion to a sedimentation tube of 100 ml, making the amount of the dispersion to 100 cm³ in total, leaving the dispersion to stand for 16 hours, and thereafter measuring the volume of the sedimented component. In the case of the volume being 3 ml or less, a desired strength is imparted to the solid preparation.

Examples of the hydrophobic assistant are alkyl celluloses such as ethyl cellulose and cellulose acetate; copolymers of acrylate or methacrylate esters; waxes such as carnauba wax, beeswax and Japan wax; hydrogenated vegetable oils such as shellac, zein, solid paraffin and hardened castor oil; monoglycerides such as glyceryl palmitostearate and glyceryl monooleate; diglycerides; triglycerides; higher fatty acid alcohols such as cetyl alcohol, stearyl alcohol and cetostearyl alcohol.

That the controlled release is hardly affected by ionic strength in the present invention means that dissolution does not change in the range of ionic strength changing in living organisms. It is preferred that the difference in dissolution rate is 7% or less in the range of 0.14-0.4 of ionic strength. In this range, so-called dose dumping becomes difficult to occur, and the range is preferably 5% or less, more preferably 4% or less.

Difference in dissolution rate caused by ionic strength is obtained in the following manner as a difference between the test solutions differing in ionic strength. A dissolution test is conducted by a method in accordance with the first method (rotating basket method) of dissolution test method described in the 14th edition of Japanese pharmacopeia using a solid preparation which contains acetoaminophenone as an active ingredient, has a weight of 0.18 g and a diameter of 0.8 cm and is molded under a compression molding pressure of 120 MPa by a static pressure press. First, a dissolution test is conducted using a solution prepared by adding α-amylase at a concentration of 5 μg/cm³ to the second solution mentioned in the Japanese pharmacopeia (pH: 6.8, ionic strength: 0.14) as a test solution under the conditions of an amount the test solution of 900 cm³, a basket rotation number of 100 rpm and a temperature of the test solution of 37±0.5° C. At a point of time before starting of test, at a point of elapsing of 30 minutes after starting of test, and at a point of elapsing of every 1 hour until 90% or more of the active ingredient is released, dissolution rate: $M_{second\ solution\ i}$ (i=0, 0.5, 1.0, 2.0, ... time before 90% or more of the active ingredient is released) of acetoaminophenone in each test solution is obtained. This is referred to as "dissolution rate 1". Using as a test solution a solvent prepared by adding α-amylase to Mcilvaine solution (pH: 7.2, ionic strength: 0.40) at a concentration of 5 μg/cm³ in the same manner as above, dissolution rate: $M_{mc\ solution\ i}$ (meaning of i is the same as above) at each point of time is obtained in the same manner as above. This is referred to as "dissolution rate 2".

The difference between dissolution rate 1 and dissolution rate 2 at each point of time is obtained as an absolute value of the value obtained by subtracting $M_{mc\ solution\ i}$ from $M_{second\ solution\ i}$, and the maximum value $\{|M_{second\ solution\ i} - M_{mc\ solution\ i}|Max\}$ is defined to be a difference in dissolution rate between test solutions different in ionic strength. The acetoaminophene is used as the active ingredient because if water solubility of active ingredient is high, the dissolution speed is too fast, resulting in overestimation of the difference in dissolution rate according to the kind or amount of the dissolution-controlling base substance, and on the other hand, if the water solubility is low, the dissolution speed is too slow, resulting in underestimation of the difference in dissolution rate.

When the difference in dissolution rate between the test solutions differing in ionic strength is 7% or less, change of dissolution speed of active ingredient caused by difference in ionic strength which changes by the influence of the region of gastrointestinal tracts or foods taken remains in a range where the change in dissolution rate of active ingredient is small. As a result, it becomes possible to perform accurate control of dissolution of active ingredient.

That the controlled release is hardly affected by compression molding pressure means that the dissolution does not change even when the pressure in compression molding changes in a specific range. It is preferred that the difference in dissolution rate is 7% or less in the range of 120-300 MPa in compression molding pressure. The difference in dissolution rate caused by the compression molding pressure is obtained from the difference between the dissolution rate obtained in dissolution test on a solid preparation molded under a compression molding pressure of 120 MPa and the dissolution rate obtained in dissolution test on a solid preparation molded under a compression molding pressure of 300 MPa. If the difference in dissolution rate caused by the compression molding pressure is 7% or less, change of dissolution characteristics caused by change or variation of conditions in production of solid preparation is within the acceptable range. The difference is preferably 5% or less and more preferably 4% or less. The difference in dissolution rate caused by the compression molding pressure is obtained specifically in the following manner as a difference in dissolution rate between solid preparations obtained under different compression molding pressures.

Using a solid preparation having a weight of 0.18 g and a diameter of 0.8 cm and molded under a compression molding pressure of 120 MPa by a static pressure press and a solid preparation molded under the same conditions as above, except for changing the compression molding pressure from 120 MPa to 300 MPa, a dissolution test is conducted in accordance with the first method (rotating basket method) of the dissolution test method mentioned in the 14th edition of Japanese pharmacopeia. The dissolution test is conducted using as a test solution the second solution mentioned in the Japanese pharmacopeia to which α-amylase is added at a concentration of 5 µg/cm$^3$ under the conditions of an amount of the test solution of 900 cm$^3$, a basket rotation number of 100 rpm and a temperature of the test solution of 37±0.5° C. At a point of time before starting of test, at a point of elapsing of 30 minutes after starting of test, and at a point of elapsing of every 1 hour until 90% or more of the active ingredient is released, dissolution rates at the respective compression molding pressures: $M_{120MPa\ i}$, $M_{300MPa\ i}$ (i=0, 0.5, 1.0, 2.0, . . . time until 90% or more of the active ingredient is released) of the active ingredient are obtained. The difference in dissolution rates at the points of time is obtained as an absolute value of the value obtained by subtracting $M_{300MPa\ i}$ from $M_{120MPa\ i}$, and the maximum value $\{|[M_{120MPa\ i}-M_{300MPa\ i}]|Max\}$ is defined to be a difference in dissolution rate between solid preparations obtained under different compression molding pressures.

If the difference in dissolution rate between solid preparations obtained under different compression molding pressures is in the range of 7% or less, the change of dissolution rate of active ingredient is in an acceptable range even when change of compression molding pressure or change of composition or amount occurs during production of solid preparation or scaling up. Furthermore, change of dissolution of active ingredient remains in an acceptable range even when change of solid preparation occurs with lapse of time. Thus, the active ingredient can be accurately controlled in dissolution.

That swelling of solid preparation is suppressed in a specific small range means that swelling of solid preparation in the test is small. The swelling degree in compression direction is preferably 1.0 or more and 2.0 or less, and the ratio between swelling degrees in the compression direction and in the direction perpendicular to the compression direction is preferably 0.5-1.5.

By adjusting the swelling degree of solid preparation in compression direction in the small range of 1.0 or more and 2.0 or less, diffusion distance of active ingredient remains in a short range. Moreover, reduction of strength of solid preparation remains in a specific range. The swelling degree is more preferably 1.0 or more and 1.8 or less, especially preferably 1.0 or more and 1.7 or less. By adjusting the ratio between swelling degrees of solid preparation in the compression direction and the direction perpendicular to the compression direction to the range of 0.5-1.5, the solid preparation swells nearly isotropically and uniformly. In this case, diffusion distance of active ingredient in the solid preparation is not too long, and reduction of strength of the swollen solid preparation remains in a specific range. The ratio between swelling degrees is more preferably 0.5-1.4. When the swelling of solid preparation is in the above range, the residence time in gastrointestinal tracts hardly changes, and besides the diffusion distance of the active ingredient remains in the range of relatively short distance. Therefore, the dissolution speed is readily maintained even in the later period of dissolution, and besides, reduction in strength of the gelling solid preparation remains in the range of small reduction. As a result, the solid preparation stands against the load caused by mechanical movement of gastrointestinal tracts, and dissolution speed can be readily kept constant. Thus, dissolution of active ingredient can be accurately controlled. When the solid preparation is in the form of multilayer tablet, separation between layers hardly occurs, and dissolution of active ingredient can be accurately controlled.

Here, the swelling degree in compression direction is defined to be proportion of swelling in compression direction of solid preparation in a test solvent which is obtained in the following manner. Using a solid preparation having a weight of 0.18 g and a diameter of 0.8 cm and molded under a compression molding pressure of 120 MPa by a static pressure press, a dissolution test is conducted in accordance with the first method (rotating basket method) of dissolution test method mentioned in the 14th edition of Japanese pharmacopeia. The dissolution test is conducted using as a test solution the second solution mentioned in the Japanese pharmacopeia to which α-amylase is added at a concentration of 5 µg/cm$^3$ under the conditions of an amount of the test solution of 900 cm$^3$, a basket rotation number of 100 rpm and a temperature of the test solution of 37±0.5° C. Sampling of the solid preparation is carried out before starting of the test and at the points of time of 0.5, 1.0, 3.0 and 6.0 hours after starting of the test, and the size in the compression direction is measured and is referred to as $M_{ai}$ (i=0, 0.5, 1.0, 3.0 and 6.0). The swelling degree in compression direction at each point of time is obtained by dividing $M_{ai}$ by $M_{a0}$, and the maximum value $\{(M_{ai}/M_{a0})max\}$ is defied to be a swelling degree in compression direction.

Furthermore, the ratio between swelling degrees in the compression direction and in the direction perpendicular to the compression direction is defied to be a ratio between swelling degrees in different directions in a test solvent which is obtained in the following manner. Using a solid preparation having a weight of 0.18 g and a diameter of 0.8 cm and molded under a compression molding pressure of 120 MPa by a static pressure press, a dissolution test is conducted in accordance with the first method (rotating basket method) of dissolution test method mentioned in the 14th edition of Japanese pharmacopeia. The dissolution test is conducted using as a test solution the second solution mentioned in the Japanese pharmacopeia to which α-amylase is added at a concentration of 5 µg/cm$^3$ under the conditions of an amount of the test solution of 900 cm$^3$, a basket rotation number of 100 rpm and a temperature of the test solution of 37±0.5° C. Sampling of the solid preparation is carried out before starting of the test and at the points of elapsing of 0.5, 1.0, 3.0 and 6.0 hours after starting of the test, and the size in the compression direction and the size in the direction perpendicular to the compression direction are measured and are referred to as $M_{ai}$, $M_{bi}$ (i=0, 0.5, 1.0, 3.0 and 6.0). Swelling degree $M_{bi}/M_{b0}$ in the compression direction and in the direction perpendicular to the compression direction is obtained by dividing $M_{ai}$ by $M_{a0}$ and $M_{bi}$ by $M_{b0}$, respectively. The ratio between swelling degrees at each point of time is obtained by dividing the swelling degree ($M_{ai}/M_{a0}$) in compression direction by the swelling degree ($M_{bi}/M_{b0}$) in the direction perpendicular to compression direction, and the maximum value $\{((M_{ai}/M_{a0})/(M_{bi}/M_{b0}))_{MAX}\}$ is defined to be the desired ratio of swelling degree.

The solid preparation in the present invention can be a layered tablet comprising at least 2 layers superposed on each other. In this case, it is preferred that the first layer contains an active ingredient and the second layer is disposed in contact with the first layer, and one or both of the first and second layers contain the dissolution-controlling base substance, because the active ingredient can be controlled to various dissolution patterns such as zero-order dissolution, multistage dissolution and timed-dissolution. The second layer may further contain the active ingredient.

The second layer disposed in contact with the first layer can cover the first layer only partially or can wrap the first layer completely. In the former case, the tablet may be multilayer tablet in which the first layer has upper surface and bottom surface, and only one of the upper surface and the bottom surface contacts with the second layer. There is no limitation in the number of the layers constituting the multilayer tablet, and the tablet may be a two-layer tablet, a three-layer tablet or a tablet comprising more layers superposed on each other. Considering dissolution pattern of active ingredient attained by the multilayer tablet and troublesomeness required for production, two-layer table or three-layer tablet is preferred.

It is desired to use the dissolution-controlling base substance containing the specific modified starch in each layer of the multilayer tablet. Some layers may not contain the dissolution-controlling base substance containing the specific modified starch. However, in order to obtain a desirable controlled release pattern, it is preferred to contain the dissolution-controlling base substance containing the specific modified starch in the layers of as many as possible. For controlling the dissolution of active ingredient from the layer containing the active ingredient to slow release by the dissolution-controlling base substance containing the specific modified starch, the content of the specific modified starch in the layer is preferably 5% by weight or more and 99.9% by weight or less, more preferably 10-99.9% by weight, particularly preferably 20-99.9% by weight. In the layer containing no active ingredient, content of the specific modified starch may be 100%.

In the case of the second layer completely wrapping the first layer, the tablet may be a core tablet in which the first layer and the second layer are concentrically disposed, and the first layer is an inner core layer and the second layer is an outer layer. In order to control the dissolution to zero-order release using the core tablet, the dissolution can be controlled to zero-order dissolution pattern by containing the active ingredient and the dissolution-controlling base substance containing the specific modified starch in both the core layer and the outer layer in designing of preparation, and suitably adjusting the contents thereof to control the dissolution speed in the core layer and the outer layer. Furthermore, for controlling the dissolution to multistage dissolution pattern, active ingredient is contained in both the core layer and the outer layer and further the dissolution-controlling base substance containing the specific modified starch is contained in the core layer or the outer layer, or both the core layer and the outer layer, and the ratio of contents is suitably adjusted, whereby the control can be attained. For controlling the dissolution to timed-dissolution, at least the dissolution-controlling base substance containing the specific modified starch is contained in the outer layer while the outer layer does not substantially contain the same active ingredient as contained in the core layer. Here, "does not substantially contain" means that the content of the same active ingredient in the outer layer is 0 in principle, but the same active ingredient as in the core layer may be contained in the outer layer in the range of a small amount which does not damage the effect to control to timed-dissolution type.

In any case, the kind of dissolution control to be given is determined based on design of preparation of core tablet, and in order to more accurately realize this desired dissolution, the dissolution-controlling base substance containing the specific modified starch can be used. The content of the dissolution-controlling base substance containing the specific modified starch in the core layer may be optionally selected in the range of 0-5% for rapid dissolution and 5-99.9% for moderate dissolution depending on the desired dissolution pattern of active ingredient contained in the core layer. In the outer layer containing active ingredient, the content of the dissolution-controlling base substance containing the specific modified starch may be optionally selected in the range of preferably 0-5% for rapid dissolution of the active ingredient and 5-99.9% for moderate dissolution. When the outer layer does not contain the same active ingredient as contained in the core layer and the active ingredient contained in the core layer is to be released in the pattern of timed-dissolution, the content is preferably 5% by weight or more, and may be 100% depending on the design of preparation. More preferred is 10-100% by weight, and further preferred is 20-100% by weight.

The solid preparation of the present invention preferably further contains a coating granule. The coating granule here means a granule which contains one or more active ingredients and is coated with a film. By containing the coating granule, there can be obtained more complex and accurate release patterns of active ingredient as required.

The coating agents for coating granule include slow release coating agents, enteric coating agents, etc. Specifically, there may be used one or more agents selected from cellulose coating agents (e.g., ethyl cellulose, hydroxypropylmethyl cellulose phthalate, carboxymethylethyl cellulose, hydroxypropylmethylcellulose acetate succinate, cellulose acetate succinate, cellulose acetate phthalate, cellulose acetate, etc.); acrylic polymer coating agents (e.g., Eudragit RS, Eudragit L, Eudragit NE, etc.); and shellac, silicon resins, and the like.

If necessary, water-soluble materials, plasticizers etc. may be added to the coating agents for adjustment of dissolution speed. As the water-soluble materials, there may be used at least one member selected from water-soluble polymers such as hydroxypropylmethyl cellulose and sugar alcohols such as mannitol; sugars such as white sugar and anhydrous maltose; surface active agents such as sucrose fatty acid esters, polyoxyethylene polyoxypropylene glycol, polysorbate and sodium laurylsulfate, etc. As the plasticizers, there may be used at least one member selected from at least one selected from acetylated monoglyceride, triethyl citrate, triacetin, dibutyl sebacate, dimethyl sebacate, middle chain fatty acid triglyceride, acetyltriethyl citrate, tributyl citrate, acetyltributyl citrate, dibutyl adipate, oleic acid, oleinol, etc.

These coating agents may be dissolved in an organic solvent and then coated on the granule or may be suspended in water and then coated on the granule. As the organic solvent, there may be used at least one selected from methanol, ethanol, propanol, isopropanol, butanol, 2-butanol, diethyl ether, ethyl acetate, n-butyl acetate, acetone, dioxane, toluene, cyclohexanone, cyclohexane, benzene, etc. Water may further be contained therein.

The granules containing active ingredient may be powders of active ingredient, granules obtained by adding binder to active ingredient or granules obtained by laminating a pharmaceutically active ingredient on green granules. As the binder, there may be used at least one selected from hydroxypropyl cellulose, hydroxypropylmethyl cellulose, polyvinyl alcohol, polyvinyl pyrrolidone, etc. The granules containing active ingredient are preferably those which are obtained by laminating a pharmaceutically active ingredient on green granules high in mechanical strength because the strength of the coating granules is increased and the coating film can be inhibited from being damaged by compression molding. Commercially available green granules high in mechanical strength are core particles "Celphere (trademark)" SCP-100, CP-203, CP-305, CP-507 (manufactured by Asahi Chemicals Co., Ltd.) comprising crystalline cellulose as a constituent, and the like.

The solid preparation of the present invention preferably has a weight of 0.20 g or more per one preparation. Thus, the dissolution time can be simply prolonged without decrease in dissolution speed in the later period of dissolution. This is because when the swelling degree in compression direction of solid preparation and the ratio between swelling degrees are in specific ranges, the dissolution of active ingredient is not affected even if the size of the solid preparation is large. In this connection, in an example where the swelling degree in compression direction and the ratio between swelling degrees are not in the above preferred ranges with using a dissolution-controlling base substance such as hydroxypropylmethyl cellulose, the dissolution speed in the later period of dissolution decreases with increase of weight of solid preparation, which is not preferred. When the swelling degree in compression direction of solid preparation and the ratio between swelling degrees are in specific ranges, the dissolution time of active ingredient can be prolonged by simply increasing the weight of solid preparation with maintaining the dissolution of active ingredient.

Next, the active ingredient is an ingredient giving chemically and biologically desired influence on peripheral environments such as living organism to which the solid preparation is administered. Examples of the active ingredient are pharmaceutical ingredient, agricultural chemical ingredient, fertilizer ingredient, food ingredient, cosmetics ingredient, dyestuff, perfume, metal, ceramics, catalyst, surface active agent, etc. The active ingredient may be in any shapes of particle, crystal, oil, liquid, semisolid, and the like, and in any forms of powder, fine particles, granule, etc. The active ingredient may be used each alone or in combination of two or more. As the active ingredient, most preferred is a pharmaceutical ingredient which requires severe performance for controlled release.

As the pharmaceutical ingredients, there are antipyretic, analgesic and antiphlogistic agents, hypnotic and sedative agents, anti-drowse agents, anti-dizzy agents, analgesic agents for children, peptic agents, antacid agents, digestive agents, cardiotonic agents, anti-arrhythmia agents, hypotensive agents, vasodilators, diuretic agents, anti-ulcer agents, medicines for intestinal disorder, medicines for osteoporosis, anti-cough and expectorants, anti-asthma agents, anti-fungus agents, pollakiuria curing agents, tonic medicines, vitamin preparations, etc. which are orally administered. The pharmaceutical ingredients may be used each alone or in combination of two or more.

The solid preparations of the present invention are particularly useful for producing preparations from one or more pharmaceutical active ingredients which have one or more features of (a) they have a short half-life in the order of 4-8 hours and must be divided and taken several times a day when administered in usual preparations, (b) they have a narrow curative index, (c) they must be sufficiently absorbed in the whole gastrointestinal tracts, or (d) they are relatively small in the dose effective for treatment. The pharmaceutical ingredients usable in the solid preparations are exemplified below, which do not limit the invention.

Analgesic and antiphlogistic agents (COX-2 inhibitors such as NSAID, fentanyl, indomethacin, ibuprofen, ketoprofen, nabumetone, paracetamol, piroxycam, tramadol, celecoxib and rofecoxib);

Anti-arrhythmia agents (procainamide, quinidine, verapamil);

Anti-fungus and anti-protist agents (amoxicilline, ampicillin, benathin penicillin, benzylpenicillin, cephachlor, cefadroxil, cefprozil, cefuroxime axetil, cephalexin, chloramphenicol, chlorochin, ciprofloxacin, clarithromycin, clavulanic acid, clindamycin, doxyxyclin, erythromycin, flucloxacillin sodium, halofantrine, isoniazid, kanamycin sulfate, lincomycin, mefloquine, minocycline, nafcilin sodium, nalidixic acid, neomycin, norfloxacin, ofloxacin, oxacillin, phenoxymethyl-penicillin pottasium, pyrimethamine-sulfadoxime, streptomycin);

Anticoagulants (warfarin);

Antidepressant agents (amitriptyline, amoxapin, butriptyline, clompramine, desipramine, dothiepin, doxepin, fluoxetine, reboxetine, aminoptine, seleridine, gepirone, imipramine, lithium carbonate, mianserine, milnacipran, nortriptyline, paroxetine, sertraline; 3-[2-[3,4-dihydrobenzofuran[3,2-c]pyridine-2(1H)-yl]ethyl]-2-methyl-4H-pyrido[1,2-a]pyrimidine-4-one);

Anti-diabetes agents (glibenclamide, metformin);

Antiepileptic agents (carbamazepin, clonazepam, ethosuximide, gabapentin, lamotrigine, lavetiracetam, phenobarbitone, fenitoin, primidone, thiagabine, topiramate, valpromide, vigabatrin);

Anti-fungus agents (amphotericin, kurotoremazole, econazole, fluconazole, flucytosine, griseofulvin, itraconazole, ketoconazole, myconazole nitrate, nystatin, terbinafine, voriconazole);

Anti-histamine agents (astemizole, cinnarizine, cyproheptazine, decarboethoxyloratadine, fexofenadine, flunarizine, levocabastine, loratadine, norastemizole, loratadine, norastemizole, oxatomide, promethazine, terphenadine);

Anti-hypertension agents (captoprilenarapril, kentaseline, riginopril, minoxidil, prazosin, ramipril, reserpine, terazocin);

Anti-muscarine action agents (atropine sulfate, hyoscine);

Anti-ulcer agents and metabolic antagonists (platinum compounds such as cisplatin and carboplatin; taxane such as paclitaxel and docetaxel; tecan such as camptothecin, irinotecan and topotecan); vinca alkaloids such as vinblastine, vindesine, vincristine and vinorelbine; nucleoside derivatives and folic acid antagonists such as 5-fluorouracil, capecitabine, gemcitabine, mercaptoprine, thioguanine, cladribine and methotrexate; alkylating agents, e.g., nitrogen mustards such as cyclophosphamide, chlorambucil, chlormethine, iphosphamide and melphalan, or nitrosoureas, e.g., carmustine and lomustine, or other alkylating agents, e.g., busulfan, dalcarbazine, procarbazine and thiotepa; antibiotics such as daunomycin, doxorubicin, idarubicin, epirubicin, bleomycin, dactinomycin and mytomycin; HER 2 antibodies such as trastuzumab; podophyllotoxin derivatives such as etoposide and teniposide; farnesyltransferase inhibitors; anthraquinone derivatives such as mitozantron);

Anti-migraine agents (alniditan, naratriptan, sumatriptan);

Anti-Parkinson's disease agents (bromocryptine mesylate levodova, seledirine);

Anti-psychotic, hypnotic and sedatives agents (alprazolam, buspirone, chlordiazepoxide, chlorpromazine chlozapine, diazepam, flupetixol, fluphenazine, flurazepam, 9-hydroxyrisperidone, lorazepam, mazapertine, olanzapine, oxazepam, pimozide, pipamperone, piracetam, promazine, risperidone, selfotel, seroquel, sertindole, sulpiride, temazepam, tiotixene, triazolam, trifluperidol, ziprasidone, zorpidem);

Anti-spasm agents (lubeluzole, lubeluzole oxide, riluzole, aptiganel, remacemide);

Cough remedies (dextromethorphan, laevodropropizine);

Antivirus agents (acilovir, ganciclovin, loviride, tivirapin, zidovudine, lamivudine, zidovudine+lamivudine, didanosine, zalcitabine, stavudine, abacavir, lopinavir, amprenavir, nevirapine, efavirenz, delavirdine, indinavir, nelfinavir, ritonavir, saquinavir, adefovir, hydroxyurea);

Beta-adrenergic-receptors (atenol, carvedilol, metoprolol, nebivolol, propanolol);

Heart inotropic agents (amrinone, digitoxin, dogoxin, milrinone);

Corticosteroids (becromethasone dipropionate, betamesone, budesonide, dexamethasone, hydrocortisone, methylprednisolone, prednisolone, prednisone, triamcinolone);

Fungicides (chlorhexidine); Diuretic agents (acetazolamide, frusemide, hydrochlorothiazide, isosorbide);

Enzymes;

Essential oils (anethol, anisum, caraway, cardamom, *cassia* oil, cineol, cinnamon oil, clove oil, *coriandrum* oil, dementholized mint oil, dill oil, *eucalyptus* oil, eugenol, ginger, lemon oil, mustard oil, neroli oil, nutmeg oil, orange oil, peppermint, sage, spearmint, terpineol, thyme);

Medicines for stomach and bowels (simetijin, cisapride, clebopride, diphenoxylate, domperidone, famotidine, lansoprazole, loperamide, loperamide oxide, mesalazine, metoclopramide, mosapride, nizatidine, norcisapride, olsalazine, omeprazole, pantoprazole, perprazole, prucalopride, rabeprazole, ranitidine, ridogrel, suphasalazine);

Hemostatic agents (aminocaproic acid);

Lipid controlling agents (atorvastine, sebastatin, pravastatin, probucol, simvastatin);

Local anesthetizing agents (benzocaine, lignocaine);

Opioid analgesic agents (buprenorphine, codein, dextromoramide, dihdrocodein, hidrocodone, oxycodone, morphine);

Parasympathetic nerve agonist and anti-dementia agents (AIT-082, eptastigime, galantamine, metrifonate, milameline, neostigmine, physostigmine, tacline, donepezil, rivastigmine, sabcomeline, talsaclidine, xanomeline, memantine, lazabemide);

Peptide and protein (antibodies, becaplermine, cyclosporine, erythropoietin, immunoglobulin, insulin);

Sex hormones (estrogens: conjugated estrogen, ethynylestradiol, mestranol, estradiol, estriol, estrone; progesterone; cromazine acetate, cyprotene, 17-deacetyl norgestimate, desogestrel, dienogest, dydrogesterone, ethynodiol diacetate, gestodene, 3-keto desogestrel, levonorgestrel, lynestrenol, methoxyprogesterone acetate, megesterol, norethindrone, norethindrone acetate, norethisterone, norethisterone acetate, norethynodrel, norgestimate, norgestrel, norgestrienone, progesterone, kingestanol);

Stimulants (sildenafil);

Vasodilators (amlodipine, buflomedil, amyl nitrite, diltiazem, dipyridamol, glyceryl trinitrate, isosorbide dinitrate, lidoflazine, molsidomine, nisaldipine, nifedipine, oxpentifylline, pentaerythritol trinitrate).

N-oxides of the above materials, pharmaceutically acceptable acid- or base-addition salts of the above materials, and stereoisomers of the above materials.

If necessary, the solid preparations of the present invention may further contain other ingredients such as binders, disintegrators, fluidizing agents, lubricants, flavors, perfumes, colorants, sweetening agents, and the like in addition to the active ingredients. These other ingredients may also be used as diluents.

As the binders, mention may be made of saccharides such as white sugar, glucose, lactose, fructose and trehalose; sugar alcohols such as mannitol, xylitol, maltitol, erythritol and sorbitol; water-soluble polysaccharides such as gelatin, pullulan, carrageenan, locust bean gum, agar, gluconannan, xanthan gum, tamarind gum, pectin, sodium alginate and gum arabic; celluloses such as crystalline cellulose (e.g., Ceolus (trademark) PH-101, PH-101D, PH-101L, PH-102, PH-301, PH-301Z, PH-302, PH-F20, PH-M06, M15, M25, KG-801, KG-802, etc. manufactured by Asahi Chemicals Co., Ltd.), powder cellulose, hydroxypropyl cellulose and methyl cellulose; starches such as alpharized starch and starch paste; synthetic polymers such as polyvinyl pyrrolidone, carboxyvinyl polymer and polyvinyl alcohol; inorganic compounds such as calcium hydrogenphosphate, calcium carbonate, synthetic hydrotalcite and magnesium silicate aluminate; etc. The binders selected from the above may be used each alone or in combination of two or more.

The crystalline celluloses usable as binders are preferably those which are excellent in compression moldability. By using the crystalline celluloses excellent in compression moldability, since tabletting can be performed under low tabletting pressure, activity of the active ingredient deactivated by tabletting pressure can be maintained, tablets containing granules can be prepared, and hardness can be given with addition of the celluloses in a small amount. Therefore, bulky active ingredients can be formed into tablets or pharmaceutical preparations containing various kinds of active ingredient can be formed into tablets. Therefore, in some cases, preparations can be formed into small tablets, liquid ingredient can be satisfactorily contained and failure in tabletting can be inhibited. As commercially available crystalline celluloses excellent in compression moldability, "Ceolus" KG-801, KG-802 (manufactured by Asahi Chemicals Co., Ltd.), and the like can be utilized.

The disintegrators include celluloses such as cross carmelose sodium, carmelose, carmelose calcium, carmelose sodium and hydroxypropyl cellulose of low-substitution degree; starches such as carboxymethyl starch sodium, hydroxypropyl starch, rice starch, wheat starch, corn starch, potato starch and partially alpharized starch; celluloses such as crystalline cellulose and powder cellulose; synthetic polymers such as cross-povidone and cross-povidone copolymer; etc. These may be used each alone or in combination of two or more.

The fluidizing agents include silicon compounds such as hydrous silicon dioxide and light anhydrous silicic acid. These may be used each alone or in combination of two or more.

As the lubricants, mention may be made of magnesium stearate, calcium stearare, stearic acid, sucrose fatty acid esters, talc, magnesium metasilicate aluminate, hydrous silicon dioxide, light anhydrous slicic acid, etc. They may be used each alone or in combination of two or more.

Here, it is preferred to use at least one lubricant selected from sucrose fatty acid esters, talc and light anhydrous slicic acid for the active ingredient having a solubility in water in the range of 0.0001-100 mg/cm$^3$ because they hardly affect the dissolution, and adhesion of tabletted powders to mortar and pestle can be inhibited. Furthermore, it is preferred to use at least one lubricant selected from magnesium metasilicate aluminate, hydrous silicon dioxide and light anhydrous silicic acid because they hardly affect the dissolution, fluidity of tabletted powders can be secured and breaking load of compression molded products can be increased. Particularly, it is preferred to use at least one lubricant selected from sucrose fatty acid esters, talc and light anhydrous slicic acid in combination with magnesium metasilicate aluminate because all of the inhibition of adhesion of tabletted powders to mortar and pestle, the securing of fluidity of tabletted powders and the increase of breaking load of compression molded products can be attained simultaneously. Moreover, it is preferred to use at least one lubricant selected from magnesium stearate, calcium stearate, stearic acid, sucrose fatty acid esters, talc and light anhydrous slicic acid for the active ingredient having a solubility in water in the range of 100-100000 mg/cm$^3$ because dissolution is hardly affected and adhesion of tabletted powders to mortar and pestle can be inhibited. Further, it is preferred to use at least one lubricant selected from magnesium metasilicate aluminate, hydrous silicon dioxide and light anhydrous silicic acid because dissolution is hardly affected, fluidity of tabletted powders can be secured, and breaking load of compression molded products can be increased. Particularly, it is preferred to use at least one lubricant selected from magnesium stearate, calcium stearate, stearic acid, sucrose fatty acid esters, talc and light anhydrous slicic acid in combination with magnesium metasilicate aluminate because all of the inhibition of adhesion of tabletted powders to mortar and pestle, the securing of fluidity of tabletted powders and the increase of breaking load of compression molded products can be attained simultaneously.

The flavors include glutamic acid, fumaric acid, succinic acid, citric acid, sodium citrate, tartaric acid, malic acid, ascorbic acid, sodium chloride, 1-menthol, etc. They may be used each alone or in combination of two or more.

The perfumes include oils such as orange, vanilla, strawberry, yogurt, menthol, fennel oil, cinnamon oil, orange-peel oil and peppermint oil, green tea, etc. These may be used each alone or in combination of two or more.

The colorants include food colorants such as Food Colorant Red No. 3, Food Colorant Yellow No. 5 and Food Colorant Blue No. 1, sodium copper chlorophyll, titanium oxide, rivoflavin, etc. These may be used each alone or in combination of two or more.

The sweetening agents include aspartame, saccharin, dipotassium glycyrrhizate, *stevia*, maltose, maltitol, thick malt syrup, *hydrangea* leaves, etc. These may be used each alone or in combination of two or more.

The solid preparation of the present invention can be produced by any methods of compression molding of solid preparations usually employed in the field of medicines. For example, there may be employed a direct powder compression method which comprises uniformly mixing an active ingredient, a dissolution-controlling base substance, and, if necessary, ingredients such as binder, disintegrator, fluidizing agent, flavor, perfume, colorant and sweetening agent, and then tabletting the mixture. There may also be employed a wet granulation tabletting method or dry granulation tabletting method which comprises wet granulating or dry granulating an active ingredient and, if necessary, a dissolution-controlling base substance, and ingredients such as binder, disintegrator, fluidizing agent, flavor, perfume, colorant and sweetening agent, and, if necessary, adding to the resulting granules a dissolution-controlling base substance, and ingredients such as binder, disintegrator, fluidizing agent, flavor, perfume, colorant and sweetening agent, and then tabletting the granules.

For making multilayer tablets, it is also possible to compression mold simultaneously the formulated powders for the two or more layers. Alternatively, there may be also employed a method of superposing two or more layers previously compression molded and again compression molding them. For making core tablets, there may be employed a compression molding method called press-coating method or dry-coating method. There may also employed a method of compression coating an outer layer on a previously compression molded core layer.

As other examples of method for producing the solid preparations, there may also be employed a method according to which an active ingredient and a fat-soluble material such as carnauba wax, hardened castor oil or polyglycerin or a hydrophilic polymer such as polyethylene glycol 6000 which is solid at room temperature, but is liquid at 40° C. or higher are uniformly mixed at a temperature condition of 40° C. or higher, then the mixture is cooled to obtain a solid, and, if necessary, the mixture is ground and adjusted in particle size, followed by compression molding. Furthermore, there may be employed a method which comprises preparing a solution of an active ingredient and a dissolution-controlling base substance using a solvent which dissolves both of them or a uniform dispersion using a suitable solvent, drying the solution or dispersion by usual method, and compression molding the resulting uniform dispersion of the active ingredient and the dissolution-controlling base substance. As the solvent, there may be used at least one solvent selected from water and organic solvents such as methanol, ethanol, propanol, isopropanol, butanol, 2-butanol, diethyl ether, ethyl acetate, n-butyl acetate, acetone, dioxane, toluene, cyclohexanone, cyclohexane, and benzene.

As the compression molding machine used for making solid preparation, there may be used compressing machines such as static pressure pressing machine, single punch tabletting machine, rotary tabletting machine, multilayer tablet molding machine, and core tablet making machine, and there is no particular limitation.

So long as the effect of the present invention is not damaged, the solid preparation per se may be coated for the purpose of control of dissolution of active ingredient, masking of taste or moisture-proofing. As the coating agent, there may be used at least one coating agent selected from, for example, cellulose coating agents (ethyl cellulose, hydroxypropylmethylcellulose phthalate, carboxymethylethyl cellulose, hydroxypropylmethylcellulose acetate succinate, cellulose acetate succinate, cellulose acetate phthalate, cellulose acetate, etc.); acrylic polymer coating agents (Eudragit RS, Eudragit L, Eudragit NE, etc.); shellac, silicone resins, etc. These coating agents can be used by known methods. The coating agent may be used as a solution in an organic solvent or suspension in water.

The present invention will be explained in detail by the following examples, which should not be construed as limiting the invention. The test methods and measuring methods for physical properties are as mentioned below.

(1) Dissolution Test: Rotating Basket Method

The dissolution test (rotating basket method) is conducted by the method in accordance with the first method (rotating basket method) of the dissolution test mentioned in the 14th edition of Japanese pharmacopeia using, as a test solution, the second solution mentioned in the Japanese pharmacopeia (pH: 6.8, ionic strength: 0.14, hereinafter sometimes referred to as "the second solution") or Mcilvaine solution (pH: 7.2, ionic strength: 0.40, composition: disodium hydrogenphosphate 173.9 mM and citric acid 13.0 mM, hereinafter sometimes referred to as "Mc solution") under the conditions of using the test solution in an amount of 900 cm$^3$, a busket rotation number of 100 rpm and a temperature of the test solution of 37±0.5° C. To each test solution is added 90 mg of an α-amylase preparation (composition: α-amylase/calcium carbonate/corn starch=5/5/90, AD "AMANO" 1, manufactured by Amano Enzyme Co., Ltd.) to give a content of α-amylase of 5 μg/cm$^3$.

(2) Dissolution Test: Paddle Method

The dissolution test (paddle method) is conducted by the method in accordance with the second method (paddle method) of the dissolution test method mentioned in the 14th edition of Japanese pharmacopeia using, as a test solution, the second solution mentioned in the Japanese pharmacopeia (pH: 6.8, ionic strength: 0.14, hereinafter sometimes referred to as "the second solution") under the conditions of using the test solution in an amount of 900 cm$^3$, a paddle rotation number of 200 rpm and a temperature of the test solution of 37±0.5° C. To the test solution is added 90 mg of an α-amylase preparation (composition: α-amylase/calcium carbonate/corn starch=5/5/90, AD "AMANO" 1, manufactured by Amano Enzyme Co., Ltd.) to give a content of α-amylase of 5 μg/cm$^3$.

(3) Particle Size Distribution: The Number of Particles Smaller than 32 μm.

This is obtained from weight percent of measurement sample which passes through a JIS sieve of 32 μm-mesh when 5 g of the sample is sieved for 5 minutes by air jet sieving.

(4) Particle Size Distribution: The Number of Particles Smaller than 75 μm.

This is obtained from weight percent of measurement sample which passes through a JIS sieve of 75 μm-mesh when 10 g of the sample is sieved for 5 minutes by air jet sieving.

(5) Particle Size Distribution: Average Particle Size (μm).

20 g of measurement sample is sieved using JIS sieves of 500 μm, 300 μm, 250 μm, 212 μm and 150 μm-mesh for 15 minutes by a Ro-Tap type sieve shaker (sieve shaker Model A manufactured by Taira Kosakusho Co., Ltd.). Then, 5 g of the measurement sample which passes through the 150 μm-mesh sieve is sieved for 5 minutes using a JIS sieve of 75 μm-mesh by air jet sieving. Furthermore, 5 g of the measurement sample which passes through the 150 μm sieve is sieved for 5 minutes using a JIS sieve of 32 μm-mesh by air jet sieving. Weight percent [%] of plus sieve of each sieve is obtained, and particle diameter when cumulative weight percent is 50% is obtained.

(6) Amount of Water-Soluble Ingredient 99 g of pure water at 20° C.±5° C. is added to 1 g of modified starch, followed by stirring with a magnetic stirrer for 2 hours to disperse the starch, and 40 cm$^3$ of the resulting dispersion is transferred to a centrifugal settling tube of 50 cm$^3$, and centrifuged at 5000G for 15 minutes. 30 cm$^3$ of the supernatant liquid is put in a weighing bottle, dried at 110° C. until the weight reaches a given value, and a dry weight (g) is measured. Furthermore, 1 g of starch is dried at 110° C. until the weight reaches a given value, and an absolute dry weight (g) is measured. The amount of water-soluble ingredient is defined to be a value obtained by the following formula (3) using the measured values obtained above.

$$\text{Amount of water-soluble ingredient}(\%) = (\text{dry weight} \times 100 \div 30) \div \text{absolute dry weight} \times 100 \quad (3)$$

(7) Moisture Retaining Capacity

W0 (g)(about 1 g) of dried modified starch is gradually put in a centrifugal settling tube of 50 cm$^3$ containing about 15 cm$^3$ of pure water of 20° C.±5° C. and dispersed in the pure water with stirring until the water becomes transparent-translucent. Pure water of 20° C.±5° C. is further added so that it occupies about 70% of the centrifugal settling tube of 50 cm$^3$, followed by centrifuging (2000G, 10 minutes). The separated upper layer is removed immediately after the completion of the centrifugation, and the moisture retaining capacity is obtained by the following formula (2) from the weight W (g) of the remaining lower layer (starch+amount of pure water retained in the starch).

$$\text{Moisture retaining capacity} = 100 \times (W - W0)/W0 \quad (2)$$

(8) Disintegration Time (Hr)

The disintegration time is defined to be a disintegration time, in a test solution, of a columnar molded product having a diameter of 1.13 cm obtained by molding 0.5 g of a formulated powder under a compressive force of 50 MPa using a static pressure press (MODEL-1321DW CREEP manufactured by Aiko Engineering Co., Ltd.). The test solution is the second solution (pH 6.8) mentioned in the 14th edition of Japanese pharmacopeia, and the disintegration test is conducted in accordance with the disintegration test method of the 14th edition of Japanese pharmacopeia using an auxiliary plate.

(9) Gel Indentation Load Value (g)

A columnar molded product having a diameter of 1.13 cm obtained by molding 0.5 g of a formulated powder under a compressive force of 50 MPa using a static pressure press (MODEL-1321DW CREEP manufactured by Aiko Engineering Co., Ltd.) is immersed in pure water at 20° C.±5° C. for 4 hours to form gel. Then, a columnar adapter having a diameter of 3 mm is indented into the gel at a rate of 0.1 mm/sec using a rheometer (RHEONER RE-33005 manufactured by YMMADEN Co., Ltd.), and the maximum load at indentation is defined to be gel indentation load value. The maximum load is a load at breakage in case the gel layer is broken, or is a maximum load shown until the adapter is penetrated by 5 mm into the columnar molded product in case the breakage does not occur. This is an average value of five tests.

(10) Gel Indentation Load Value (g) Under the Condition of Storage with Heating

A columnar molded product having a diameter of 1.13 cm obtained by molding 0.5 g of a modified starch under a compressive force of 50 MPa using a static pressure press (MODEL-1321DW CREEP manufactured by Aiko Engineering Co., Ltd.) is immersed in pure water at 37° C.±0.5° C. for 4 hours to form gel. Then, a columnar adapter having a diameter of 3 mm is indented into the gel at a rate of 0.1 mm/sec using a rheometer (RHEONER RE-33005 manufactured by YMMADEN Co., Ltd.), and the indentation load value is defined to be a value giving firstly a peak when the adapter is indented. This is an average value of five tests.

(11) Swelling Degree of Modified Starch (cm$^3$/g)

1.0 g of modified starch is dispersed in pure water of 20° C.±5° C., the dispersion is transferred to a settling tube of 100 cm$^3$, 100 cm$^3$ in total amount of the dispersion is left to stand for 16 hours, and thereafter, volume V (cm$^3$) of the lower layer of the upper and lower separating layers, and dry weight (g) of 1.0 g of the modified starch are measured. The value of swelling degree is calculated by the following formula (4).

Swelling degree of modified starch $(cm^3/g) = V/$dry weight of modified starch    (4)

(12) Angle of Repose (°)

The angle of repose is measured using Sugihara's measuring device for angle of repose ("Pharmacology", 27, p. 260, 1965).

(13) Specific Volume ($cm^3/g$)

This is measured using Scott volume meter (manufactured by Tsutsui Rikagakukiki Co., Ltd.). A powder sample is allowed to flow down into a measuring vessel over 2-3 minutes using a metering feeder until the powder overflows the vessel. Then, excess powder accumulated above the vessel is scraped off and the powder attaching to the side surface of the vessel is removed. Then, the weight of powder roughly filled in the vessel is measured. The value obtained by dividing the volume of the measuring vessel by the weight of powder roughly filled in the vessel is taken as specific volume.

(14) Swelling Degree of Solid Preparation in Compression Direction 0.18 g of formulated powder is molded under a compressive force of 120 MPa by a static pressure press (MODEL-1321DW CREEP manufactured by Aiko Engineering Co., Ltd.) to prepare tablets in the form of R having a diameter of 8 mmφ.

A dissolution test is conducted in accordance with the first method (rotating basket method) of dissolution test method mentioned in the 14th edition of Japanese pharmacopeia using as a test solution the second solution mentioned in the Japanese pharmacopeia to which α-amylase is added at a concentration of 5 μg/$cm^3$ under the conditions of an amount of the test solution of 900 $cm^3$, a basket rotation number of 100 rpm and a temperature of the test solution of 37±0.5° C. Sampling of the solid preparation is carried out before starting of the test and at the points of time of 0.5, 1.0, 3.0 and 6.0 hours elapsing after starting of the test, and the size in the compression direction is measured and is referred to as $M_{ai}$ (i=0, 0.5, 1.0, 3.0 and 6.0). The swelling degree $M_{ai}/M_{a0}$ in compression direction at each point of time is obtained by dividing $M_{ai}$ by $M_{a0}$, and the maximum value $(M_{ai}/M_{a0})$max is defied to be a swelling degree in compression direction of the solid preparation.

(15) Ratio of Swelling Degree 0.18 g of formulated powder is molded at a compressive force of 120 MPa by a static pressure press (MODEL-1321DW CREEP manufactured by Aiko Engineering Co., Ltd.) to prepare tablets in the form of R having a diameter of 8 mmφ.

A dissolution test is conducted in accordance with the first method (rotating basket method) of dissolution test method mentioned in the 14th edition of Japanese pharmacopeia using as a test solution the second solution mentioned in the Japanese pharmacopeia to which α-amylase is added at a concentration of 5 μg/$cm^3$ under the conditions of an amount of the test solution of 900 $cm^3$, a basket rotation number of 100 rpm and a temperature of the test solution of 37±0.5° C. Sampling of the solid preparation is carried out before starting of the test and at the points of time of 0.5, 1.0, 3.0 and 6.0 hours after starting of the test, and the size in the compression direction and the size in the direction perpendicular to the compression direction are measured and are referred to as $M_{ai}$, $M_{a0}$ (i=0, 0.5, 1.0, 3.0 and 6.0), respectively. Swelling degree $(M_{ai}/M_{a0})$ in the compression direction at each point of time is obtained by dividing $M_{ai}$ by $M_{a0}$ and swelling degree $M_{bi}/M_{b0}$ in the direction perpendicular to the compression direction at each point of time is obtained by dividing $M_{bi}$ by $M_{b0}$. The swelling degree in compression direction is divided by the swelling degree in the direction perpendicular to compression direction to obtain the ratio of swelling degrees at each point of time $(M_{ai}/M_{a0})$ $(M_{bi}/M_{b0})$ and the maximum value $((M_{ai}/M_{a0})/(M_{bi}/M_{b0}))$MAX is obtained as the ratio of swelling degree.

(16) Difference in Dissolution Rate Between Test Solutions Different in Ionic Strength 0.18 g of formulated powder is molded at a compressive force of 120 MPa by a static pressure press (MODEL-1321DW CREEP manufactured by Aiko Engineering Co., Ltd.) to prepare tablets in the form of R having a diameter of 8 mmφ.

A dissolution test is conducted by the method in accordance with the first method (rotating basket method) of the dissolution test method mentioned in the 14th edition of Japanese pharmacopeia using acetoaminophene as an active ingredient and using as the test solution the second solution mentioned in the Japanese pharmacopeia and Mcilvaine solution (pH: 7.2, ionic strength: 0.40, composition: disodium hydrogenphosphate 173.9 mM and citric acid 13.1 mM) to which α-amylase is added at a concentration of 5 μg/$cm^3$, respectively, and under the conditions of using 900 $cm^3$ of either of the solutions, a basket rotation number of 100 rpm and a temperature of the test solution of 37±0.5° C. At a point of time before starting of test, at a point of elapsing of 30 minutes after starting of test, and at a point of elapsing of every 1 hour until 90% or more of the active ingredient is released, dissolution rates: $M_{second\ solution\ i}$ and $M_{mc\ solution\ i}$ (i=0, 0.5, 1.0, 2.0, . . . time until 90% or more of the active ingredient is released) of acetoaminophenone in each test solution are obtained. The difference in dissolution rates at each point of time is obtained as an absolute value of the value obtained by subtracting $M_{mc\ solution\ i}$ from $M_{second\ solution\ i}$, and the maximum value $|M_{second\ solution\ i} - M_{mc\ solution\ i}|$Max is obtained as a difference in dissolution rate in test solutions different in ionic strength.

(17) Difference in Dissolution Rate Between Solid Preparations Different in Compression Molding Pressure 0.18 g of formulated powder is molded at a compressive forces of 120 MPa and 300 MPa by a static pressure press (MODEL-1321DW CREEP manufactured by Aiko Engineering Co., Ltd.) to prepare tablets in the form of R having a diameter of 8 mmφ.

A dissolution test is conducted by the method in accordance with the first method (rotating basket method) of the dissolution test method mentioned in the 14th edition of Japanese pharmacopeia using as the test solution the second solution mentioned in the Japanese pharmacopeia to which α-amylase is added at a concentration of 5 μg/$cm^3$ under the conditions of using the test solution in an amount of 900 $cm^3$, a basket rotation number of 100 rpm and a temperature of the test solution of 37±0.5° C. At a point of time before starting of test, at a point of elapsing of 30 minutes after starting of test, and at a point of elapsing of every 1 hour until 90% or more of the active ingredient is released, dissolution rates of active ingredient: $M_{120MPai}$ and $M_{300MPai}$ (i=0, 0.5, 1.0, 2.0, . . . time until 90% or more of the active ingredient is released) on respective tablets differing in compression molding pressure. The difference in dissolution rates at each point of time is obtained as an absolute value of the value obtained by subtracting $M_{300MPai}$ from $M_{120MPai}$, and the maximum value $|M_{120MPai} - M_{300MPai}|$ Max is obtained as a difference in dissolution rate between solid preparations differing in compression molding pressure.

(18) Ratio of Dissolution Speed in Initial Period and Dissolution Speed in Later Period 0.18 g of formulated powder is molded at a compressive forces of 120 MPa and 300 MPa by a static pressure press (MODEL-1321DW CREEP manufactured by Aiko Engineering Co., Ltd.) to prepare tablets in the form of R having a diameter of 8 mmφ, and a dissolution test is conducted by the method in accordance with the first method (rotating basket method) of dissolution test method mentioned in the 14th edition of Japanese pharmacopeia. The dissolution test is conducted using as the test solution either of the second solution mentioned in the 14th edition of Japanese pharmacopeia and Mcilvaine solution (pH: 7.2, ionic strength: 0.40, composition: disodium hydrogenphosphate 173.9 mM and citric acid 13.1 mM) to which α-amylase is added at a concentration of 5 μg/cm$^3$, respectively, and under the conditions of the amount of test solution being 900 cm$^3$, a basket rotation number of 100 rpm and a temperature of the test solution of 37±0.5° C. At the point of time of 30 minutes elapsing after starting of the test and at every 1 hour elapsing until 90% or more of the active ingredient is released, the test solution is sampled and dissolution rate of the active ingredient is obtained. From the data obtained, times required for 20, 40, 70 and 90% of the active ingredient to release are calculated. The time required for release of 20% of the active ingredient is obtained by the method in which sampling times before or after the dissolution rate of the active ingredient reaching 20% and dissolution rates at that time are plotted on a graph and the points are connected with a straight line, and dissolution time corresponding to a dissolution rate of 20% is read as the point on the straight line. Similarly, times required for 40, 70 and 90% of the active ingredient to release are obtained by the method in which sampling times before or after the dissolution rate of the active ingredient reaching 40%, 70% and 90% and dissolution rates at that time are plotted on a graph and the points are connected with a straight line, and the dissolution times corresponding to dissolution rates of 40%, 70% and 90% are read as the points on the straight line. Based on the data obtained as above, the initial dissolution speed: $M_{20-40}$% and the later dissolution speed: $M_{70-90\%}$ are obtained, and the ratio of dissolution speed in initial period and dissolution speed in later period ($M_{20-40\%}/M_{70-90\%}$) is obtained.

Example 1

Potato starch was filled in a stainless steel vat (50 cm×25 cm) in a layer thickness of 5 cm and subjected to reduction in pressure (600 mmHg) for 5 minutes in a pressure vessel. Then, the starch was subjected to wet heat treatment with pressurized steam (120° C.) for 20 minutes, and a starch emulsion having a solid concentration of 7.5% was prepared using the above treated starch as a raw material. This starch emulsion was heated and gelatinized by a jet cooker at 20 L/hr (outlet temperature 100° C.), followed by spray drying. Then, the starch was ground and classified using a pin type mill having therein a classifying device to obtain a modified starch A. Basic physical properties of the modified starch A are shown in Table 2. Furthermore, the modified starch A was fractionated to particle size of 150-500 μm, 75-150 μm, 32-75 μm, and 0-32 μm, and swelling degree and gel indentation load under the condition of storage with heating of each modified starch were measured and the results are shown in Table 1. Furthermore, swelling state of the modified starch after being left to stand for 16 hours was observed by a light microscope after uniformly re-dispersing the upper and lower separating layers, and shown in FIG. 1-FIG. 2.

The resulting modified starch A, crystalline cellulose ("Ceolus" KG-802 manufactured by Asahi Chemical Co., Ltd.), polyethylene glycol (Macrogol 6000 (trade name) manufactured by Sanyo Kasei Kogyo Co., Ltd.) and acetoaminophene (manufactured by API Corporation) were uniformly mixed at a weight ratio of 60/20/10/10. The mixture was compressed under a pressure of 120 MPa using a static pressure press (MODEL-1321DW CREEP manufactured by Aiko Engineering Co., Ltd.) to obtain tablet A-1 having a diameter of 0.8 cm and a weight of 0.18 g and tablet A-3 having a diameter of 1.13 cm and a weight of 0.5 g. In the same manner, the above mixture was compressed under a pressure of 300 MPa to obtain similar tablet A-2 having a diameter of 0.8 cm and a weight of 0.18 g.

Dissolution test of tablet A-1 was conducted using as a test solution the second solution mentioned in the Japanese pharmacopeia (pH: 6.8, ionic strength: 0.14) to which α-amylase was added at a concentration of 5 μm/cm$^3$ by rotating basket method (100 rpm) and paddle method (200 rpm). In this test, swelling degree of the tablet and dissolution pattern of acetoaminophene were measured. Moreover, dissolution test was conducted by rotating basket method (100 rpm) in the same manner as above, except that the test solution was changed from the second solution mentioned in the Japanese pharmacopeia to Mcilvaine solution (pH: 7.2, ionic strength: 0.40), and various physical properties were measured. Furthermore, dissolution test on tablets A-2, A-3 was conducted by rotating basket method (100 rpm) using as a test solution the second solution mentioned in the Japanese pharmacopeia to which α-amylase was added at a concentration of 5 μg/cm$^3$, and similarly the physical properties were measured.

The results of dissolution test of tablets A-1, A-2 are shown in FIG. 7, and the results of dissolution test of tablets A-3 are shown in FIG. 8. The results of measurement of swelling degree of tablet A-1 are shown in Table 3, and the difference in dissolution rates between those obtained using different test solutions, the difference in dissolution rates between tablets obtained under different compression molding pressures, and the ratio of the dissolution speed in initial period and the dissolution speed in later period are shown in Table 4.

The controlled release tablets of acetoaminophene produced using modified starch A as the dissolution-controlling base substance and polyethylene glycol as the water-soluble polymer assistant were low in swelling (in proper range) and showed zero-order dissolution which did not depend on liquid property or pH of the test solution. When the tablets were increased in weight from 0.18 g to 0.5 g, the zero-order dissolution was maintained although the dissolution time was prolonged. When the load of dissolution test was increased, the dissolution speed on the whole somewhat increased, but dose dumping did not occur and stable dissolution was shown.

Example 2

The modified starch A obtained in Example 1, crystalline cellulose ("Ceolus" KG-802 manufactured by Asahi Chemical Co., Ltd.), polyethylene glycol (Macrogol 6000 (trade name) manufactured by Sanyo Kasei Kogyo Co., Ltd.), sorbitol (manufactured by Nikken Kagaku Co., Ltd.) and acetoaminophene (manufactured by API Corporation) were uniformly mixed at a weight ratio of 55/5/10/10/20. The mixture was compressed under a pressure of 120 MPa using a static pressure press (MODEL-1321DW CREEP manufactured by Aiko Engineering Co., Ltd.) to obtain tablet B having a diameter of 1.13 cm and a weight of 0.5 g.

Figure 9:
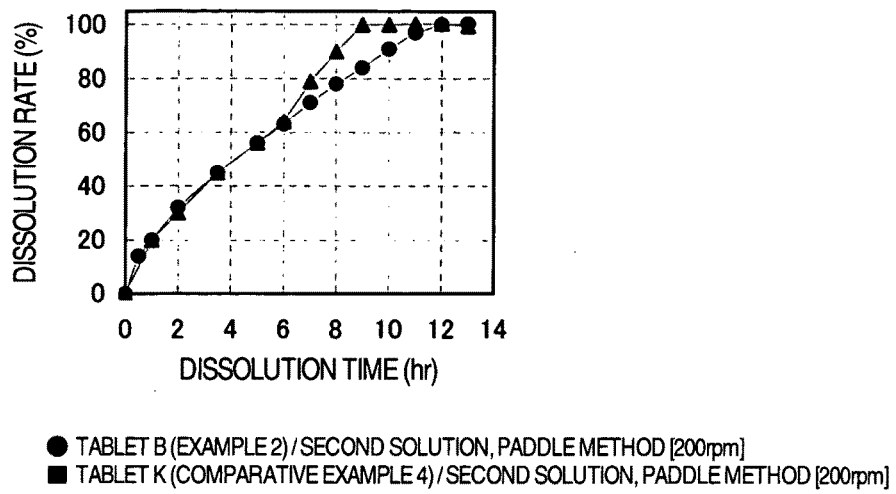
FIG. 9 Results of dissolution test on tablet B obtained in Example 2 and tablet K obtained in Comparative Example 4.

Dissolution test was conducted by paddle method (200 rpm) using the tablet B and, as a test solution, the second solution mentioned in the Japanese pharmacopeia (pH: 6.8, ionic strength: 0.14) to which α-amylase was added at a concentration of 5 μm/cm$^3$ to measure the dissolution pattern of acetoaminophene. The results of the dissolution test are shown in FIG. 9.

The controlled release tablet of acetoaminophene produced using modified starch A as the dissolution-controlling base substance, polyethylene glycol as the water-soluble polymer assistant and sorbitol as the water-soluble assistant showed stable zero-order dissolution. In Comparative Example 4 where the water-soluble assistant was not added, the dissolution speed of the active ingredient increased in the later period of dissolution as compared with the formulation used in this example. In the case of the formulation in this example, high strength of the gelling tablet was maintained with addition of sorbitol, and stable dissolution was attained.

Example 3

The modified starch A obtained in Example 1, crystalline cellulose ("Ceolus" KG-802 manufactured by Asahi Chemical Co., Ltd.), polyethylene glycol (Macrogol 6000 (trade name) manufactured by Sanyo Kasei Kogyo Co., Ltd.), sorbitol (Sorbitol SP manufactured by Nikken Kagaku Co., Ltd.), acetoaminophene (manufactured by API Corporation), talc (Talcan Hayashi manufactured by Hayashi Kasei Co., Ltd.) and Neusilin (manufactured by Fuji Kagaku Kogyo Co., Ltd.) were uniformly mixed at a weight ratio of 45/11/7/10/20/5/2. The mixture was compressed under a pressure of 150 MPa using a rotary tabletting machine (Clean Press Collect 12HUK manufactured by Kikusui Seisakusho Co., Ltd.) to obtain tablet C having a diameter of 1.2 cm and a weight of 0.5 g. Similarly, the modified starch A, the crystalline cellulose, the polyethylene glycol, the sorbitol, the acetoaminophene, talc and the Neusilin were uniformly mixed at a weight ratio of 50/6/7/10/20/5/2 and a weight ratio of 55/1/7/10/20/5/2, and from the mixtures were obtained tablets D and E having a diameter of 1.2 cm and a weight of 0.5 g.

Figure 10:
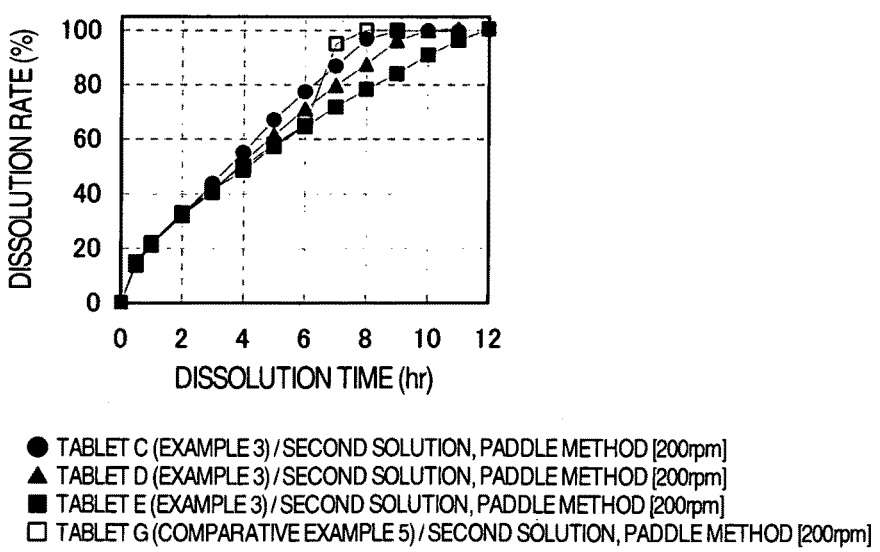
FIG. 10 Results of dissolution test on tablets C, D, E obtained in Example 3 and tablet G obtained in Comparative Example 5.

Dissolution test was conducted by paddle method (200 rpm) using the tablets C-E and, as a test solution, the second solution mentioned in the Japanese pharmacopeia (pH: 6.8, ionic strength: 0.14) to which α-amylase was added at a concentration of 5 μm/cm$^3$ to measure the dissolution pattern of acetoaminophene. The results of the dissolution test are shown in FIG. 10.

The controlled release tablet of acetoaminophene produced using modified starch A as the dissolution-controlling base substance, polyethylene glycol as the water-soluble polymer assistant, sorbitol as the water-soluble assistant and talc and Neusilin as lubricants could be obtained by rotary tabletting machine without causing failure in tabletting. Furthermore, the resulting tablets showed stable zero-order dissolution, and were prolonged in dissolution time with increase of the amount of the modified starch.

Example 4

Controlled release tablet F containing, as an active ingredient, Ethenzamide which is hardly soluble in water (amount of solvent required for dissolving 1 g of solute being 10000 cm$^3$ or more) mentioned in the Japanese pharmacopeia was produced by the following method. The modified starch A obtained in Example 1, crystalline cellulose ("Ceolus" KG-802 manufactured by Asahi Chemical Co., Ltd.), sorbitol (Sorbitol SP manufactured by Nikken Kagaku Co., Ltd.), polyethylene glycol (Macrogol 6000 (trade name) manufactured by Sanyo Kasei Kogyo Co., Ltd.), ethenzamide (manufactured by API Corporation), talc (Talcan Hayashi manufactured by Hayashi Kasei Co., Ltd.) and Neusilin (manufactured by Fuji Kagaku Kogyo Co., Ltd.) were uniformly mixed at a weight ratio of 46.5/9.5/9.5/0.5/30/3/1. The mixture was compressed under a pressure of 150 MPa using a rotary tabletting machine (Clean Press Collect 12HUK manufactured by Kikusui Seisakusho Co., Ltd.) to obtain controlled release tablet F having a diameter of 8.0 mm and a weight of 0.2 g.

Figure 11:
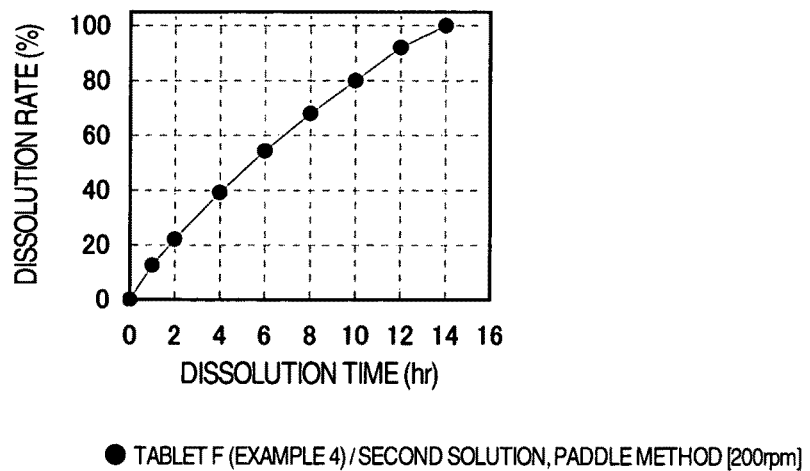
FIG. 11 Results of dissolution test on tablet F obtained in Example 4.

Dissolution test was conducted by paddle method (200 rpm) using the controlled release tablet F and, as a test solution, the second solution mentioned in the Japanese pharmacopeia (pH: 6.8, ionic strength: 0.14) to which α-amylase was added at a concentration of 5 μm/cm$^3$ to measure the dissolution pattern of ethenzamide. The results of the dissolution test are shown in FIG. 11.

The controlled release tablet of ethenzamie produced using modified starch A as the dissolution-controlling base substance, polyethylene glycol as the water-soluble polymer assistant, sorbitol as the water-soluble assistant and talc and Neusilin as lubricants showed stable zero-order dissolution.

Example 5

Controlled release tablet G containing, as an active ingredient, sodium salicylate which is a medicine highly soluble in water (amount of solvent required for dissolving 1 g of solute being less than 1 cm$^3$) and is mentioned in the Japanese pharmacopeia was produced by the following method. The modified starch A obtained in Example 1, crystalline cellulose ("Ceolus" KG-802 manufactured by Asahi Chemical Co., Ltd.), polyethylene glycol (Macrogol 6000 (trade name) manufactured by Sanyo Kasei Kogyo Co., Ltd.), sodium salicylate (manufactured by API Corporation), magnesium stearate (manufactured by Taihei Kagaku Sangyo Co., Ltd.) and Neusilin (manufactured by Fuji Kagaku Kogyo Co., Ltd.) were uniformly mixed at a weight ratio of 55/13/10/20/0.5/2. The mixture was compressed under a pressure of 150 MPa using a rotary tabletting machine (Clean Press Collect 12HUK manufactured by Kikusui Seisakusho Co., Ltd.) to obtain controlled release tablet G having a diameter of 12.0 mm and a weight of 0.5 g.

Figure 12:
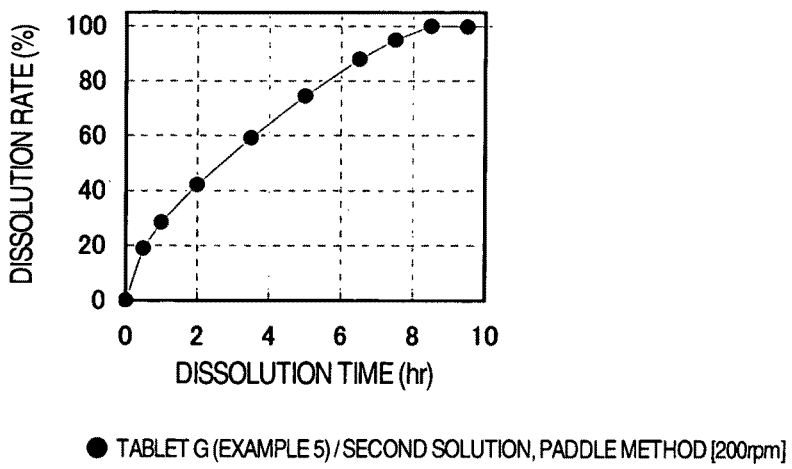
FIG. 12 Results of dissolution test on tablet G obtained in Example 5.

Dissolution test was conducted by paddle method (200 rpm) using the resulting tablet and, as a test solution, the second solution mentioned in the Japanese pharmacopeia (pH: 6.8, ionic strength: 0.14) to which α-amylase was added at a concentration of 5 μm/cm$^3$ to measure the dissolution pattern of sodium salicylate. The results of the dissolution test are shown in FIG. 12.

The controlled release tablet of sodium salicylate produced using modified starch A as the dissolution-controlling base substance, polyethylene glycol as the water-soluble polymer assistant, magnesium stearate and Neusilin as lubricants could be obtained by a rotary tabletting machine without problems such as failure in tabletting, and showed stable zero-order dissolution.

Comparative Example 1

Potato starch was filled in a stainless steel vat (50 cm×25 cm) in a layer thickness of 5 cm and subjected to reduction in pressure (600 mmHg) for 5 minutes in a pressure vessel. Then, the starch was treated with pressurized steam (120° C.) for 20 minutes, and a starch emulsion having a solid concentration of 7.5% was prepared using the treated starch as a raw material. This starch emulsion was heated and gelatinized by a jet cooker at 20 L/hr (outlet temperature 115° C.) and spray dried to obtain modified starch B (corresponding to Example 5 of Patent Document 10). The basic physical properties of the modified starch B are shown in Table 2. The modified starch B was larger in particle size than modified starch A.

Tablet H-1 obtained by compressing under a pressure of 120 MPa and tablet H-2 obtained by compressing under a pressure of 300 MPa were produced in the same manner as in Example 1, except that the above resulting modified starch B, crystalline cellulose ("Ceolus" KG-802 manufactured by Asahi Chemical Co., Ltd.), polyethylene glycol (Macrogol 6000 (trade name) manufactured by Sanyo Kasei Kogyo Co., Ltd.) and acetoaminophene (manufactured by API Corporation) were uniformly mixed at a weight ratio of 60/20/10/10, and dissolution test was conducted as in Example 1.

The results of dissolution test are shown in FIG. 13. The results of measurement of swelling degree of tablet H-1 (tablet obtained under compression molding pressure of 120 MPa) are shown in Table 3, and the difference in dissolution rates using different test solutions, the difference in dissolution rates between tablets obtained under different compression molding pressures, and the ratio of the dissolution speed in initial period and the dissolution speed in later period are shown in Table 4.

The controlled release tablet of acetoaminophene produced using modified starch B as the dissolution-controlling base substance was high in swelling, and dissolution of acetoaminophene greatly changed between tablets produced under different compression molding pressure. Furthermore, when load in dissolution test was increased, dose dumping occurred. In the case of the tablet using modified starch B as the dissolution-controlling base substance, strength of the gelling tablet decreased, and hence the dissolution depended on the compression molding pressure, and dose dumping occurred with increase in load.

Comparative Example 2

Potato starch was filled in a stainless steel vat (50 cm×25 cm) in a layer thickness of 5 cm and subjected to reduction in pressure (600 mmHg) for 5 minutes in a pressure vessel. Then, the starch was treated with pressurized steam (120° C.) for 20 minutes, and a starch emulsion having a solid concentration of 7.5% was prepared using the treated starch as a raw material. This starch emulsion was heated and gelatinized by a jet cooker at 20 L/hr (outlet temperature 100° C.) and continuously passed through a retention tube (100° C.) of 3 L container, followed by spray drying to obtain modified starch C. The basic physical properties of the modified starch C are shown in Table 2 (corresponding to Example 6 of Patent Document 10). The modified starch C was larger in particle size than the modified starch A.

The resulting modified starch C was fractionated into particle size of 150-500 μm, 75-150 μm, 32-75 μm, and 0-32 μm, and swelling degree and gel indentation load under condition of storage with heating of the modified starches were measured and the results are shown in Table 1. Furthermore, swelling state of the modified starches after being left to stand for 16 hours was observed by a light microscope after uniformly re-dispersing the upper and lower separating layers, and is shown in FIG. 3-FIG. 6.

Tablet I-1 obtained by compressing under a pressure of 120 MPa and tablet I-2 obtained by compressing under a pressure of 300 MPa were produced in the same manner as in Example 1, except that the modified starch C, crystalline cellulose ("Ceolus" KG-802 manufactured by Asahi Chemical Co., Ltd.), polyethylene glycol (Macrogol 6000 (trade name) manufactured by Sanyo Kasei Kogyo Co., Ltd.) and acetoaminophene (manufactured by API Corporation) were uniformly mixed at a weight ratio of 60/20/10/10, and dissolution test was conducted as in Example 1.

The results of dissolution test are shown in FIG. 14. The results of measurement of swelling degree of tablet I-1 (tablet obtained under compression molding pressure of 120 MPa) are shown in Table 3, and the difference in dissolution rates using different test solutions, the difference in dissolution rates between tablets obtained under different compression molding pressures, and the ratio of the dissolution speed in initial period and the dissolution speed in later period are shown in Table 4.

The controlled release tablet of acetoaminophene produced using modified starch C as the dissolution-controlling base substance was high in swelling, and dissolution of acetoaminophene greatly changed between tablets produced under different compression molding pressures. Furthermore, when load in dissolution test was increased, dose dumping occurred. In the case of the tablet using modified starch C as the dissolution-controlling base substance, strength of the gelling tablet decreased, and hence the dissolution depended on the compression molding pressure, and dose dumping occurred with increase in load.

Comparative Example 3

Potato starch was filled in a stainless steel vat (50 cm×25 cm) in a layer thickness of 5 cm and subjected to reduction in pressure (600 mmHg) for 5 minutes in a pressure vessel. Then, the starch was subjected to wet heat treatment with pressurized steam (120° C.) for 20 minutes, and a starch emulsion having a solid concentration of 7.5% was prepared using the treated starch as a raw material. This starch emulsion was heated and gelatinized by a jet cooker at 20 L/hr (outlet temperature 100° C.) and spray dried. Then, the starch was ground and classified using a pin type mill having therein a classifying device to obtain modified starch D. Basic physical properties of the modified starch D are shown in Table 2. The modified starch D was larger in particle size than modified starch A and contained 86.6% by weight of particles which passed through a 75 μm-mesh sieve.

Tablet J-1 compressed under a pressure of 120 MPa and tablet J-2 compressed under a pressure of 300 MPa were produced in the same manner as in Example 1, except that the modified starch D, crystalline cellulose ("Ceolus" KG-802 manufactured by Asahi Chemical Co., Ltd.), polyethylene glycol (Macrogol 6000 (trade name) manufactured by Sanyo Kasei Kogyo Co., Ltd.) and acetoaminophene (manufactured by API Corporation) were uniformly mixed at a weight ratio of 60/20/10/10, and dissolution test was conducted as in Example 1.

The results of dissolution test are shown in FIG. 15. The results of measurement of swelling degree of tablet J-1 (tablet obtained under compression molding pressure of 120 MPa) are shown in Table 3, and the difference in dissolution rates using different test solutions, the difference in dissolution rates between tablets obtained under different compression molding pressures, and the ratio of the dissolution speed in initial period and the dissolution speed in later period are shown in Table 4.

The controlled release tablet of acetoaminophene produced using modified starch D as the dissolution-controlling base substance was high in swelling, and dissolution of acetoaminophene greatly changed between tablets produced under different compression molding pressures. Furthermore, when load in dissolution test was increased, dose dumping occurred. In the case of the tablet using modified starch D as the dissolution-controlling base substance, strength of the gelling tablet decreased as in Comparative Example 1, and hence the dissolution depended on the compression molding pressure, and dose dumping occurred with increase in load.

Comparative Example 4

Tablet K was produced in the same manner as in Example 2, except that the modified starch A obtained in Example 1, crystalline cellulose ("Ceolus" KG-802 manufactured by Asahi Chemical Co., Ltd.), polyethylene glycol (Macrogol 6000 (trade name) manufactured by Sanyo Kasei Kogyo Co., Ltd.) and acetoaminophene (manufactured by API Corporation) were uniformly mixed at a weight ratio of 55/20/5/20, and dissolution test was conducted as in Example 2. The results of the dissolution test are shown in FIG. 9.

The controlled release tablet of acetoaminophene produced using modified starch A as the dissolution-controlling base substance and polyethylene glycol as the water-soluble polymer assistant showed relatively stable dissolution, but temporarily increased in dissolution speed in the course of dissolution. Since the gelling tablet was low in strength, erosion of the tablet increased and the dissolution speed increased in the course of dissolution.

Comparative Example 5

Tablet L was produced in the same manner as in Example 3, except that the modified starch A obtained in Example 1, crystalline cellulose ("Ceolus" KG-802 manufactured by Asahi Chemical Co., Ltd.), polyethylene glycol (Macrogol 6000 (trade name) manufactured by Sanyo Kasei Kogyo Co., Ltd.), sorbitol (manufactured by Nikken Kagaku Co., Ltd.), acetoaminophene (manufactured by API Corporation) and magnesium stearate (manufactured by Taihei Kagaku Sangyo Co., Ltd.) were uniformly mixed at a weight ratio of 55/7.7/7/10/20/0.5, and dissolution test was conducted as in Example 3. The results of the dissolution test are shown in FIG. 10.

The controlled release tablet of acetoaminophene produced using modified starch A as the dissolution-controlling base substance and magnesium stearate as the lubricant could be obtained by rotary tabletting without problems such as failure in tabletting, but dose dumping occurred during dissolution. The magnesium stearate used as the lubricant hindered hydration and gelation of the modified starch, and strength of gelling tablet decreased to cause dose dumping.

Comparative Example 6

Tablet M-1 having a diameter of 0.8 cm and a weight of 0.18 g obtained under a compression pressure of 120 MPa, tablet M-2 having a diameter of 0.8 cm and a weight of 0.18 g obtained under a compression pressure of 300 MPa, and tablet M-3 having a diameter of 1.13 cm and a weight of 0.5 g obtained under a compression pressure of 120 MPa were produced in the same manner as in Example 1, except that low-viscosity hydroxypropylmethyl cellulose (Metolose 90SH-100SR (trade name) manufactured by Shin-Etsu Chemical Co., Ltd.), crystalline cellulose ("Ceolus" KG-802 manufactured by Asahi Chemical Co., Ltd.), polyethylene glycol (Macrogol 6000 manufactured by Sanyo Kasei Kogyo Co., Ltd.) and acetoaminophene (manufactured by API Corporation) were uniformly mixed at a weight ratio of 60/20/10/10, and dissolution test was conducted as in Example 1.

The basic physical properties of the low-viscosity hydroxypropylmethyl cellulose are shown in Table 2, the results of dissolution test on tablets M-1 and M-2 are shown in FIG. 16, and the results of dissolution test on tablet M-3 (tablet weight 0.5 g) are shown in FIG. 8. The results of measurement of swelling degree of the tablets obtained under compression molding pressure of 120 MPa are shown in Table 3, and the difference in dissolution rates using different test solutions, the difference in dissolution rates between tablets obtained under different compression molding pressures, and the ratio of the dissolution speed in initial period and the dissolution speed in later period are shown in Table 4.

The controlled release tablet of acetoaminophene produced using the low-viscosity hydroxypropylmethyl cellulose as a dissolution-controlling base substance was disintegrated in 2 hours in Mcilvain solution having an ionic strength of 0.4 and dose dumping occurred. The small tablet of 0.18 g showed zero-order dissolution, but when the weight of the tablet was increased to 0.5 g, the dissolution speed decreased in the later period of dissolution, and zero-order dissolution was not attained.

Comparative Example 7

Tablet N-1 having a diameter of 0.8 cm and a weight of 0.18 g obtained under a compression pressure of 120 MPa and tablet N-2 having a diameter of 0.8 cm and a weight of 0.18 g obtained under a compression pressure of 300 MPa were produced in the same manner as in Example 1, except that high-viscosity hydroxypropylmethyl cellulose (Metolose 90SH-4000SR manufactured by Shin-Etsu Chemical Co., Ltd.), crystalline cellulose ("Ceolus" KG-802 manufactured by Asahi Chemical Co., Ltd.), polyethylene glycol (Macrogol 6000 manufactured by Sanyo Kasei Kogyo Co., Ltd.) and acetoaminophene (manufactured by API Corporation) were uniformly mixed at a weight ratio of 50/30/10/10, and dissolution test was conducted as in Example 1.

The basic physical properties of the high-viscosity hydroxypropylmethyl cellulose are shown in Table 2, and the results of dissolution test are shown in FIG. 17. The results of measurement of swelling degree of the tablet N-1 (tablet obtained under compression molding pressure of 120 MPa) are shown in Table 3, and the difference in dissolution rates using different test solutions, the difference in dissolution rates between tablets obtained under different compression molding pressures, and the ratio of the dissolution speed in initial period and the dissolution speed in later period are shown in Table 4.

The controlled release tablet of acetoaminophene produced using the high-viscosity hydroxypropylmethyl cellulose as a dissolution-controlling base substance was disintegrated in 2 hours in Mcilvain solution having an ionic strength of 0.4, and dose dumping occurred. In this comparative example using high-viscosity HPMC as compared with HPMC used in Comparative Example 6, the dissolution speed decreased in the later period of dissolution, and zero-order dissolution was hardly attained.

Comparative Example 8

Tablet O-1 having a diameter of 0.8 cm and a weight of 0.18 g obtained under a compression pressure of 120 MPa and tablet O-2 having a diameter of 0.8 cm and a weight of 0.18 g obtained under a compression pressure of 300 MPa were produced in the same manner as in Example 1, except that polyethylene oxide (POLYOX WSR303 (trade name) manufactured by Dow Chemical Corp.), crystalline cellulose ("Ceolus" KG-802 manufactured by Asahi Chemical Co., Ltd.), polyethylene glycol (Macrogol 6000 manufactured by Sanyo Kasei Kogyo Co., Ltd.) and acetoaminophene (manufactured by API Corporation) were uniformly mixed at a weight ratio of 60/20/10/10, and dissolution test was conducted as in Example 1.

The basic physical properties of the polyethylene oxide are shown in Table 2, and the results of dissolution test are shown in FIG. 18. The results of measurement of swelling degree of the tablet O-1 (tablet obtained under compression molding pressure of 120 MPa) are shown in Table 3, and the difference in dissolution rates using different test solutions, the difference in dissolution rates between tablets obtained under different compression molding pressures, and the ratio of the dissolution speed in initial period and the dissolution speed in later period are shown in Table 4.

The controlled release tablet of acetoaminophene produced using the polyethylene oxide as a dissolution-controlling base substance was highly swollen on the whole, the dissolution speed decreased in the later period of dissolution, and zero-order dissolution was hardly attained.

Comparative Example 9

Tablet P-1 having a diameter of 0.8 cm and a weight of 0.18 g obtained under a compression pressure of 120 MPa and tablet P-2 having a diameter of 0.8 cm and a weight of 0.18 g obtained under a compression pressure of 300 MPa were produced in the same manner as in Example 1, except that polyethylene oxide (POLYOX WSR303 manufactured by Dow Chemical Corp.), polyethylene glycol (Macrogol 6000 manufactured by Sanyo Kasei Kogyo Co., Ltd.) and acetoaminophene (manufactured by API Corporation) were uniformly mixed at a weight ratio of 37.5/50/12.5, and dissolution test was conducted as in Example 1.

The results of dissolution test are shown in FIG. 19, the results of measurement of swelling degree of tablet P-1 (tablet obtained under compression molding pressure of 120 MPa) are shown in Table 3, and the difference in dissolution rates using different test solutions, the difference in dissolution rates between tablets obtained under different compression molding pressures, and the ratio of the dissolution speed in initial period and the dissolution speed in later period are shown in Table 4.

The controlled release tablet of acetoaminophene produced using the polyethylene oxide as a dissolution-controlling base substance was highly swollen on the whole, the dissolution speed decreased in the later period of dissolution, and zero-order dissolution was not attained.

Comparative Example 10

Tablet Q-1 having a diameter of 0.8 cm and a weight of 0.18 g obtained under a compression pressure of 120 MPa and tablet Q-2 having a diameter of 0.8 cm and a weight of 0.18 g obtained under a compression pressure of 300 MPa were produced in the same manner as in Example 1, except that xanthan gum (manufactured by Saneigen F.F.I. Co., Ltd.), crystalline cellulose ("Ceolus" KG-802 manufactured by Asahi Chemical Co., Ltd.), calcium sulfate (manufactured by Wako Pure Chemical Industries, Ltd.), polyethylene glycol (Macrogol 6000 manufactured by Sanyo Kasei Kogyo Co., Ltd.) and acetoaminophene (manufactured by API Corporation) were uniformly mixed at a weight ratio of 60/10/10/10/10, and dissolution test was conducted as in Example 1.

Particle size distribution of the xanthan gum is shown in Table 2, the results of dissolution test are shown in FIG. 20, the results of measurement of swelling degree of tablet Q-1 (tablet obtained under compression molding pressure of 120 MPa) are shown in Table 3, and the difference in dissolution rates using different test solutions, the difference in dissolution rates between tablets obtained under different compression molding pressures, and the ratio of the dissolution speed in initial period and the dissolution speed in later period are shown in Table 4.

The controlled release tablet of acetoaminophene produced using the xanthan gum as a dissolution-controlling base substance was highly swollen on the whole, the dissolution speed decreased in the later period of dissolution and zero-order dissolution was not attained.

Comparative Example 11

Tablet R-1 having a diameter of 0.8 cm and a weight of 0.18 g obtained under a compression pressure of 120 MPa and tablet R-2 having a diameter of 0.8 cm and a weight of 0.18 g obtained under a compression pressure of 300 MPa were produced in the same manner as in Example 1, except that Eudragit RSPO (trade name, manufactured by Degussa AG) which was a kind of dissolution-controlling base substance, crystalline cellulose ("Ceolus" KG-802 manufactured by Asahi Chemical Co., Ltd.), polyethylene glycol (Macrogol 6000 manufactured by Sanyo Kasei Kogyo Co., Ltd.) and acetoaminophene (manufactured by API Corporation) were uniformly mixed at a weight ratio of 60/20/10/10, and dissolution test was conducted as in Example 1.

Basic physical properties of Eudragit RSPO are shown in Table 2, the results of dissolution test are shown in FIG. 21, the results of measurement of swelling degree of tablet R-1 (tablet obtained under compression molding pressure of 120 MPa) are shown in Table 3, and the difference in dissolution rates using different test solutions, the difference in dissolution rates between tablets obtained under different compression molding pressures, and the ratio of the dissolution speed in initial period and the dissolution speed in later period are shown in Table 4.

Dissolution of acetoaminophene from the controlled release tablet produced using the xanthan gum as a dissolution-controlling base substance decreased in the later period of dissolution and zero-order dissolution was not attained. Furthermore, the dissolution greatly changed between the tablets obtained under different compression molding pressures.

Comparative Example 12

Tablet S-1 having a diameter of 0.8 cm and a weight of 0.18 g obtained under a compression pressure of 120 MPa and tablet S-2 having a diameter of 0.8 cm and a weight of 0.18 g obtained under a compression pressure of 300 MPa were produced in the same manner as in Example 1, except that a mixture of polyvinyl acetate and polyvinyl pyrrolidone (Coridon SR (trade name) manufactured by BASF Corp.), crystalline cellulose ("Ceolus" KG-802 manufactured by Asahi Chemical Co., Ltd.), polyethylene glycol (Macrogol 6000 manufactured by Sanyo Kasei Kogyo Co., Ltd.) and acetoaminophene (manufactured by API Corporation) were uniformly mixed at a weight ratio of 60/20/10/10, and dissolution test was conducted as in Example 1.

Basic physical properties of the mixture of polyvinyl acetate and polyvinyl pyrrolidone are shown in Table 2, the results of dissolution test are shown in FIG. 22, the results of measurement of swelling degree of tablet S-1 (tablet obtained under compression molding pressure of 120 MPa) are shown in Table 3, and the difference in dissolution rates using different test solutions, the difference in dissolution rates between tablets obtained under different compression molding pressures, and the ratio of the dissolution speed in initial period and the dissolution speed in later period are shown in Table 4.

Dissolution speed of acetoaminophene from the controlled release tablet produced using the mixture of polyvinyl acetate and polyvinyl pyrrolidone as a dissolution-controlling base substance decreased in the later period of dissolution, and zero-order dissolution was not attained. Furthermore, the dissolution greatly changed in test solutions different in ionic strength.

Example 6

Crystalline cellulose ("Ceolus" KG-802 manufactured by Asahi Chemical Co., Ltd.), lactose for direct compression tabletting (Supertab manufactured by Asahi Chemical Co., Ltd.), cross carmelose sodium ("Kiccolate" ND-2HS), and acetoaminophene (manufactured by API Corporation) were uniformly mixed at a weight ratio of 20/69/1/10. The mixture was compressed under a pressure of 20 MPa using a static pressure press (MODEL-1321DW CREEP manufactured by Aiko Engineering Co., Ltd.) to obtain a core layer having a diameter of 0.8 cm and a weight of 0.18 g.

A formulated powder for outer layer obtained by uniformly mixing modified starch A obtained in Example 1, crystalline cellulose and cross carmelose sodium at a weight ratio of 80/20/20 was compression coated on the above core layer by the above static pressure press under a pressure of 240 MPa to obtain a core tablet A having a diameter of 11.3 mm and a weight of 0.60 g.

Similarly, core tablet B and core tablet C differing in the amount of cross carmelose were obtained using as a formulated powder for outer layer a powder obtained by uniformly mixing modified starch A, crystalline cellulose and cross carmelose sodium at a weight ratio of 80/20/10 and 80/20/5.

Figure 23:
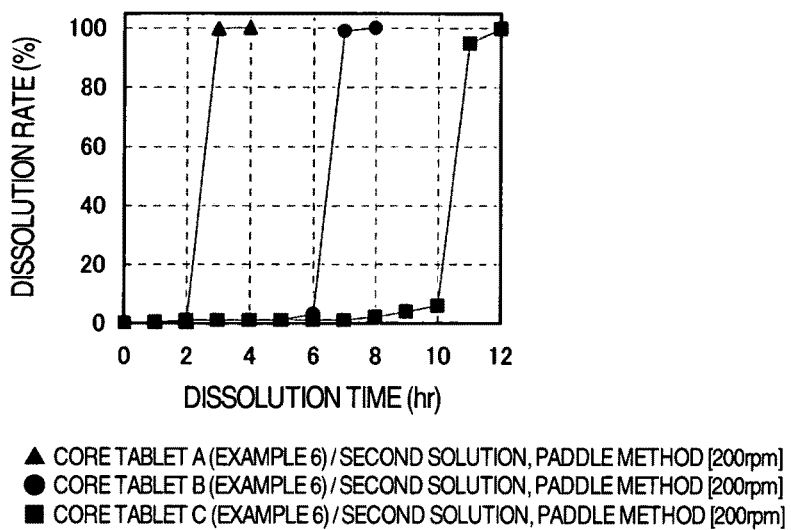
FIG. 23 Results of dissolution test on core tablets A, B, C obtained in Example 6.

Dissolution test was conducted using the resulting core tablets A-C and, as a test solution, the second solution mentioned in the Japanese pharmacopeia to which α-amylase was added at a concentration of 5 μm/cm$^3$ by paddle method (200 rpm) to measure dissolution pattern of acetoaminophene. The results of measurement are shown in FIG. 23.

When modified starch A was used as the dissolution-controlling substance, and the core layer was of rapid release and the outer layer was a barrier layer containing no active ingredient, the tablets showed timed-release according to which the active ingredient was rapidly released after lag time. Furthermore, when the mixing ratio of modified starch A and carmelose sodium in the formulation of the outer layer was changed, the tablets showed timed-release with lag times of 2, 6 and 10 hours.

Example 7

On a core layer obtained in the same manner as in Example 6 was compression coated a formulated powder for outer layer obtained by uniformly mixing modified starch A obtained in Example 1, crystalline cellulose ("Ceolus" KG-802 manufactured by Asahi Chemical Co., Ltd.), and polyethylene glycol (Macrogol 6000 (trade name) manufactured by Sanyo Kasei Kogyo Co., Ltd.) at a weight ratio of 80/20/7 by the above static pressure press under a pressure of 240 MPa to obtain a core tablet D having a diameter of 11.3 mm and a weight of 0.60 g.

Similarly, core tablet E differing in the amount of polyethylene glycol was obtained using as a formulated powder for outer layer a powder obtained by uniformly mixing modified starch A, crystalline cellulose and polyethylene glycol at a weight ratio of 80/20/0.5.

Figure 24:
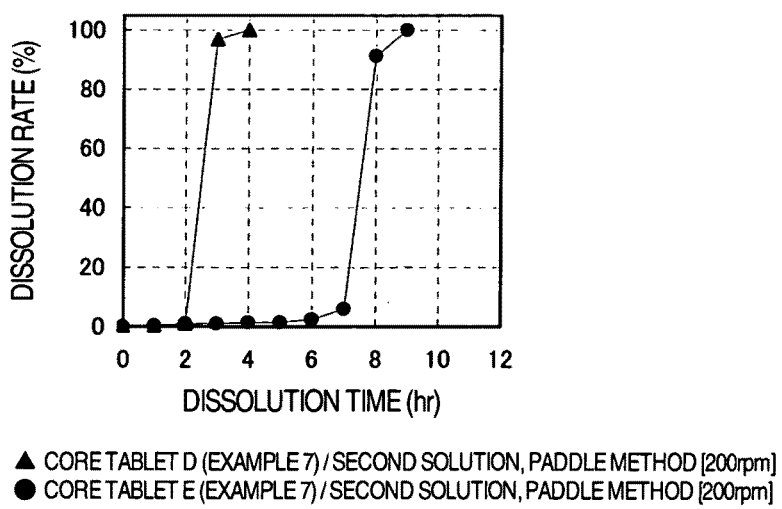
FIG. 24 Results of dissolution test on core tablets D, E obtained in Example 7.

Dissolution test was conducted using the resulting core tablets D and E and, as a test solution, the second solution mentioned in the Japanese pharmacopeia to which α-amylase was added at a concentration of 5 μm/cm$^3$ by paddle method (200 rpm) to measure dissolution pattern of acetoaminophene. The results of measurement are shown in FIG. 24.

When modified starch A was used as the dissolution-controlling substance, and the core layer was of rapid release and the outer layer was a barrier layer containing no active ingredient, the tablets showed timed-release according to which the active ingredient was rapidly released after lag time. Furthermore, when the mixing ratio of modified starch A and polyethylene glycol in the formulation of the outer layer was changed, the tablets showed timed-release with lag times of 2 and 7 hours.

Example 8

On a core layer obtained in the same manner as in Example 6 was compression coated a formulated powder for outer layer obtained by uniformly mixing modified starch A obtained in Example 1 and crystalline cellulose ("Ceolus" KG-802 manufactured by Asahi Chemical Co., Ltd.) at a weight ratio of 75/25 by the above static pressure press under a pressure of 240 MPa to obtain a core tablet F having a diameter of 11.3 mm and a weight of 0.60 g.

Similarly, core tablets G-I differing in the amount of modified starch A were obtained using as a formulated powder for outer layer a powder obtained by uniformly mixing modified starch A and crystalline cellulose at weight ratios of 70/30, 60/40 and 50/50.

Figure 25:
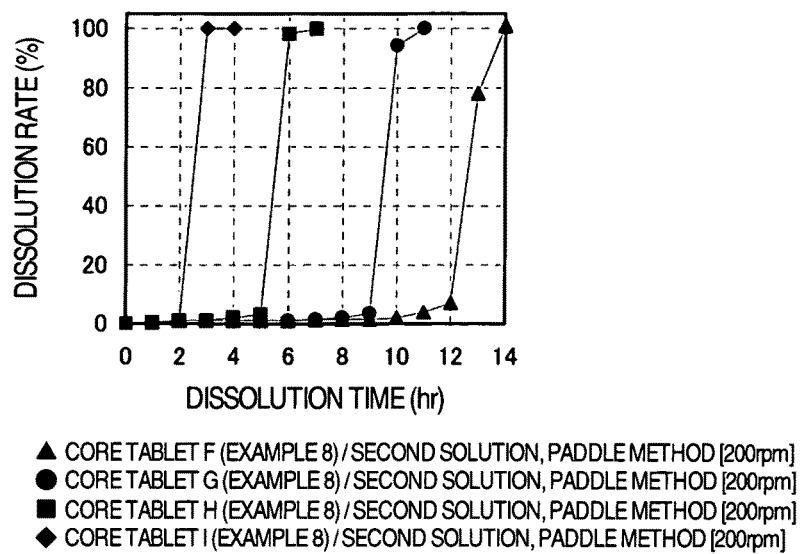
FIG. 25 Results of dissolution test on core tablets F, G, H, I obtained in Example 8.

Dissolution test was conducted using the resulting core tablets F-I and, as a test solution, the second solution mentioned in the Japanese pharmacopeia to which α-amylase was added at a concentration of 5 μm/cm$^3$ by paddle method (200 rpm) to measure dissolution pattern of acetoaminophene. The results of measurement are shown in FIG. 25.

When modified starch A was used as the dissolution-controlling substance, and the core layer was of rapid release and the outer layer was a barrier layer containing no active ingredient, the tablets showed timed-release according to which the active ingredient was rapidly released after lag time. Furthermore, when the amount of modified starch A in the formulation of the outer layer was changed, the tablets showed timed-release with lag times of 2, 4, 9, 12 hours.

Example 9

Modified starch A obtained in Example 1, crystalline cellulose ("Ceolus" KG-802 manufactured by Asahi Chemical Co., Ltd.), lactose for direct compression tabletting (Supertab manufactured by Asahi Chemical Co., Ltd.), polyethylene glycol (Macrogol 6000 (trade name) manufactured by Sanyo Kasei Kogyo Co., Ltd.) and acetoaminophene (manufactured by API Corporation) were uniformly mixed at a weight ratio of 45/10/15/10/20. The mixture was compressed under a pressure of 20 MPa using a static pressure press (MODEL- 1321DW CREEP manufactured by Aiko Engineering Co., Ltd.) to obtain a core layer having a diameter of 0.6 cm and a weight of 0.08 g.

A formulated powder for outer layer obtained by uniformly mixing modified starch A obtained in Example 1, crystalline cellulose, sorbitol (Sorbitol SP manufactured by Nikken Kagaku Co., Ltd.), cross carmelose sodium and acetoaminophene at a weight ratio of 55/24/10/6/5 was compression coated on the above core layer by the above static pressure press under a pressure of 240 MPa to obtain a core tablet J having a diameter of 9.0 mm and a weight of 0.32 g.

Figure 26:
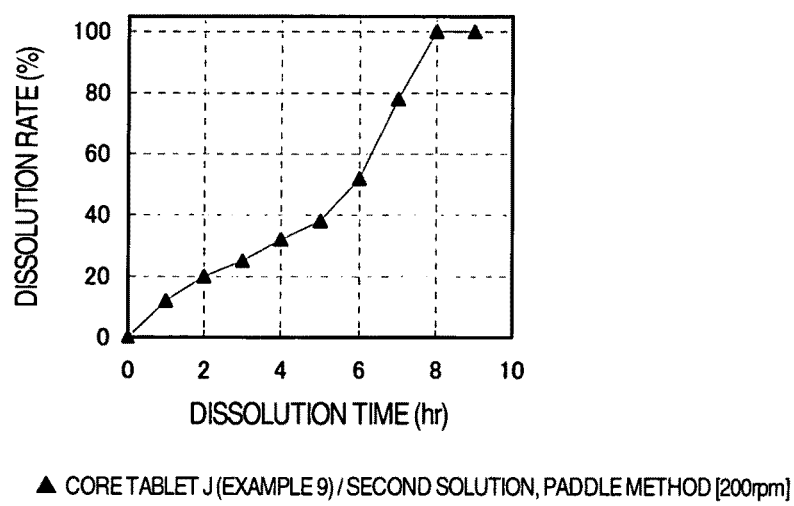
FIG. 26 Results of dissolution test on core tablet J obtained in Example 9.

Dissolution test was conducted using the resulting core tablet J and, as a test solution, the second solution mentioned in the Japanese pharmacopeia to which α-amylase was added at a concentration of 5 μm/cm$^3$ by paddle method (200 rpm) to measure dissolution pattern of acetoaminophene. The results of measurement are shown in FIG. 26.

When modified starch A was used as the dissolution-controlling substance, both the core layer and the outer layer contained modified starch A and active ingredient, and the amounts of modified starch A and active ingredient were adjusted, the tablet showed two-stage release in which the dissolution rate increased in the later period of dissolution.

Example 10

Modified starch A obtained in Example 1, crystalline cellulose ("Ceolus" KG-802 manufactured by Asahi Chemical Co., Ltd.), lactose for direct compression tabletting (Supertab manufactured by Asahi Chemical Co., Ltd.), polyethylene glycol (Macrogol 6000 (trade name) manufactured by Sanyo Kasei Kogyo Co., Ltd.) and acetoaminophene (manufactured by API Corporation) were uniformly mixed at a weight ratio of 55/10/20/10/10. The mixture was compressed under a pressure of 20 MPa using a static pressure press (MODEL-1321DW CREEP manufactured by Aiko Engineering Co., Ltd.) to obtain a core layer having a diameter of 0.8 cm and a weight of 0.18 g.

A formulated powder for outer layer obtained by uniformly mixing modified starch A, crystalline cellulose and cross carmelose sodium at a weight ratio of 80/20/10 was compression coated on the above core layer by the above static pressure press under a pressure of 240 MPa to obtain a core tablet K having a diameter of 11.3 mm and a weight of 0.60 g.

Figure 27:
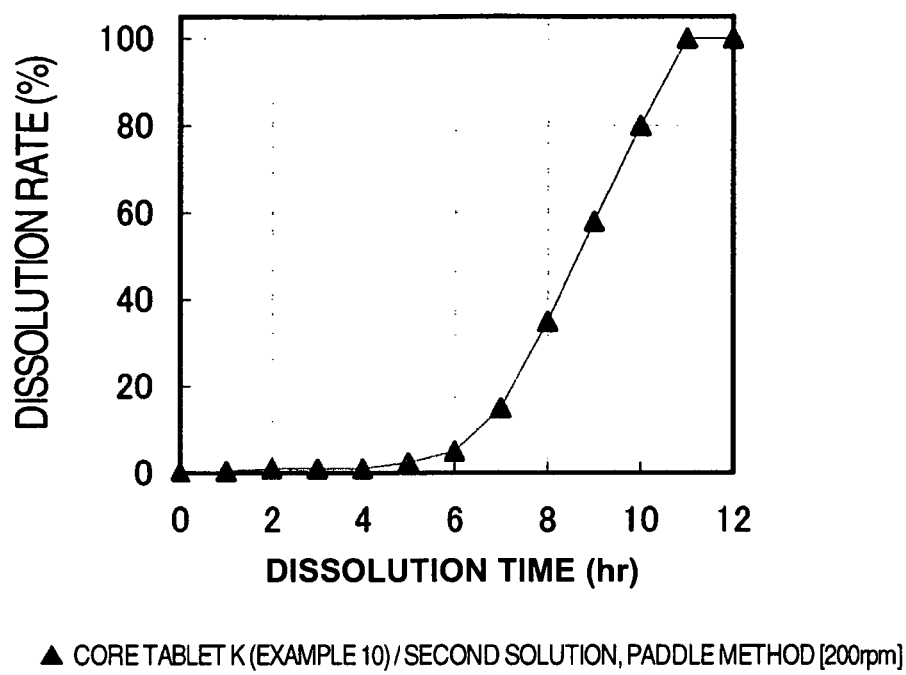
FIG. 27 Results of dissolution test on core tablet K obtained in Example 10.

Dissolution test was conducted using the resulting core tablet K and, as a test solution, the second solution mentioned in the Japanese pharmacopeia to which α-amylase was added at a concentration of 5 μm/cm$^3$ by paddle method (200 rpm) to measure dissolution pattern of acetoaminophene. The results of measurement are shown in FIG. 27.

When modified starch A was used as the dissolution-controlling substance, the core layer was of controlled release, and the outer layer was a barrier layer containing no active ingredient, the tablet showed timed-release in which the active ingredient was released after a lag time.

Example 11

On a core layer obtained in the same manner as in Example 1 was compression coated a formulated powder for outer layer obtained by uniformly mixing modified starch A obtained in Example 1, crystalline cellulose ("Ceolus" KG-802 manufactured by Asahi Chemical Co., Ltd.), and sorbitol (Sorbitol SP manufactured by Nikken Kagaku Co., Ltd.) at a weight ratio of 80/20/10 by the above static pressure press under a pressure of 240 MPa to obtain a core tablet L having a diameter of 11.3 mm and a weight of 0.60 g.

Figure 28:
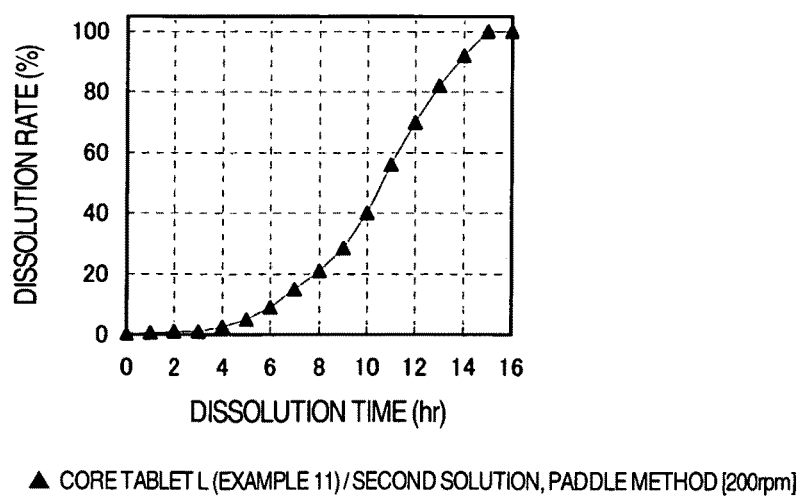
FIG. 28 Results of dissolution test on core tablet L obtained in Example 11.

Dissolution test was conducted using the resulting core tablet L and, as a test solution, the second solution mentioned in the Japanese pharmacopeia to which α-amylase was added at a concentration of 5 μm/cm$^3$ by paddle method (200 rpm) to measure dissolution pattern of acetoaminophene. The results of measurement are shown in FIG. 28.

When modified starch A was used as the dissolution-controlling substance, and the core layer was of controlled release and the outer layer was a barrier layer having permeability to the active ingredient, the tablet showed timed-release according to which the active ingredient was slowly released after a lag time.

TABLE 1

|  |  | Example 1 | | | Comparative Example 2 | | | | |
| --- | --- | --- | --- | --- | --- | --- | --- | --- | --- |
|  |  | Modified starch A Fractionation in particle size | | | Modified starch C Fractionation in particle size | | | | |
|  |  | Total | 0-32 μm | 32-75 μm | Total | 0-32 μm | 32-75 μm | 75-150 μm | 150-500 μm |
| Particle size | 0-32 μm | 44.4 | 100 |  | 1.5 | 100 |  |  |  |
| distribution | 32-75 μm | 55.2 |  | 100 | 20.1 |  | 100 |  |  |
| (wt %) | 75-150 μm | 0.4 |  |  | 37.4 |  |  | 100 |  |
|  | 150-500 μm | 0 |  |  | 41.0 |  |  |  | 100 |
| Swelling degree (cm$^3$/g) |  | 10 | 8.5 | 7 | 19 | 14.4 | 27 | 26.5 | 22 |
| Gel indentation load (g) |  | 291 | 282 | 284 | 202 | 286 | 219 | 207 | 190 |

TABLE 2

|  |  | Particle size distribution (wt %) | | | |
| --- | --- | --- | --- | --- | --- |
|  |  | 0-32 μm | 32-75 μm | >75 μm | Average particle diameter (μm) |
| Example 1 | Modified starch A | 44.4 | 55.2 | 0.4 | 32 |
| Comparative Example 1 | Modified starch B | 3.5 | 22.2 | 74.3 | 132 |
| Comparative Example 2 | Modified starch C | 1.5 | 20.1 | 78.4 | 151 |
| Comparative Example 3 | Modified starch D | 33.2 | 53.4 | 13.4 | 45 |

TABLE 2-continued

| | | | | |
|---|---|---|---|---|
| Comparative Example 6 | Metolose 90SH100SR | 32 | 50.1 | 17.9 |
| Comparative Example 7 | Metolose 90SH4000SR | 19 | 59.6 | 21.4 |
| Comparative Example 8 | POLYOX WSR303 | 26.6 | 31.7 | 41.7 |
| Comparative Example 10 | Xanthan gum | 13.6 | 45.2 | 41.2 |
| Comparative Example 11 | Eudragit RSPO | 10 | 28.4 | 61.6 |
| Comparative Example 12 | Coridon SR | 10.9 | 35.5 | 53.6 |

| Amount of water-soluble ingredient (%) | Moisture retaining capacity (%) | Disintegration time (hr) | Gel indentation load (g) | Swelling degree ($cm^3/g$) | Angle of repose (°) | Apparent specific gravity ($g/cm^3$) |
|---|---|---|---|---|---|---|
| 69.8 | 876 | >8 | 443 | 10 | 42 | 0.34 |
| 84.5 | 1474 | >8 | 229 | 1 | 44 | 0.25 |
| 70.0 | 1036 | >8 | 233 | 30 | 45 | 0.27 |
| 68.9 | 918 | >8 | 251 | 17 | 43 | 0.3 |
| | | | | | 48 | 0.29 |
| | | | | | 52 | 0.27 |
| | | | | | 42.5 | 0.47 |
| | | | | | — | — |
| | | | | | 38.5 | 0.52 |
| | | | | | 37 | 0.4 |

TABLE 3

| | Swelling degree in compression direction | Ratio of swelling degree in total |
|---|---|---|
| Example 1 | 1.95 | 1.47 |
| Comparative Example 1 | 1.70 | 1.52 |
| Comparative Example 2 | 1.82 | 1.55 |
| Comparative Example 3 | 1.62 | 1.51 |
| Comparative Example 6 | 1.90 | 2.03 |
| Comparative Example 7 | 2.69 | 2.25 |
| Comparative Example 8 | 2.62 | 1.54 |
| Comparative Example 9 | 2.33 | 1.25 |
| Comparative Example 10 | 2.58 | 1.37 |
| Comparative Example 11 | 1.27 | 1.15 |
| Comparative Example 12 | 1.60 | 1.42 |

TABLE 4

| | Difference in dissolution rate of active ingredient between test solutions (%) | Difference in dissolution rate between tablets different in compression pressure (%) | Ratio between initial and later periods in dissolution speed | | |
|---|---|---|---|---|---|
| | | | Second solution, 120 MPa | Mcilvaine solution, 120 MPa | Second solution, 300 MPa |
| Example 1 | 3.7 | 3.2 | 0.78 | 0.65 | 0.92 |
| Comparative Example 1 | 3.0 | 11.0 | 0.88 | 0.92 | 0.61 |
| Comparative Example 2 | 4.0 | 15.0 | 1.08 | 0.82 | 0.71 |
| Comparative Example 3 | 2.0 | 8.0 | 0.81 | 0.82 | 0.66 |
| Comparative Example 6 | Unmeasurable due to disintegration of tablet | 5.2 | 0.66 | Unmeasurable due to disintegration of tablet | 0.67 |
| Comparative Example 7 | Unmeasurable due to disintegration of tablet | 1.8 | 0.55 | Unmeasurable due to disintegration of tablet | 0.53 |
| Comparative Example 8 | 3.3 | 2.6 | 0.46 | 0.33 | 0.44 |
| Comparative Example 9 | 2.8 | 5.1 | 0.52 | 0.46 | 0.45 |
| Comparative Example 10 | 5.1 | 3.6 | 0.43 | 0.43 | 0.39 |
| Comparative Example 11 | 4.2 | 12.9 | 0.12 | 0.10 | 0.15 |
| Comparative Example 12 | 12.4 | 6.4 | 0.17 | 0.15 | 0.17 |

INDUSTRIAL APPLICABILITY

The solid preparations are used in applications such as medicines, agricultural chemicals, fertilizers, feeds, foods, industries and cosmetics as controlled release solid preparations which are not affected by environments in living organisms such as ionic strength and pH, compressive force in compression molding, and kind and content of active ingredient, less in change of residence time in gastrointestinal tracts, and can be controlled in release of active ingredient to zero-order release, two or more stage release or timing release.

The invention claimed is:

1. A solid preparation which comprises at least one active ingredient and at least one dissolution-controlling base substance and is obtained by compression molding, wherein the dissolution-controlling base substance contains a modified starch such that the solid preparation contains 5.0-99.9% by weight of the modified starch based on the total weight of the solid preparation, the modified starch having a moisture retaining capacity of 400% or more and a gel indentation load of 200 g or more, the modified starch containing a water-soluble ingredient in an amount of 40-95% by weight based on the total weight of the modified starch, the modified starch having particles passing through a 75 μm-mesh sieve in the proportion of 90% by weight or more and particles passing through a 32 μm-mesh sieve in the proportion of 20% by weight or more, having an average particle diameter of not smaller than 20 μm and smaller than 50 μm, the modified starch having an angle of repose of 45° or smaller, a specific volume of 1.4-3.6 cm$^3$/g, and a swelling degree of 6-10 cm$^3$/g, wherein a difference between a dissolution rate obtained from a dissolution test conducted using as a test solution the second solution specified in the Japanese pharmacopeia and a dissolution rate obtained from a dissolution test conducted using as a test solution the Mcilvaine solution is 7% or less, and wherein a difference between a dissolution rate obtained from a dissolution test on a solid preparation molded under a pressure of 120 MPa in compression molding and a dissolution rate obtained from a dissolution test on a solid preparation molded under a pressure of 300 MPa in compression molding is 7% or less.

2. The solid preparation according to claim 1, wherein the modified starch has particles passing through a 75 μm-mesh sieve in the proportion of 98% by weight or more and particles passing through a 32 μm-mesh sieve in the proportion of 40% by weight or more.

3. The solid preparation according to claim 1, wherein the dissolution-controlling base substance further contains a hydrophilic polymer assistant and the weight ratio of the modified starch to the hydrophilic polymer assistant is in the range of 50:50-99.9:0.1.

4. The solid preparation according to claim 3, wherein the hydrophilic polymer assistant is a synthetic or natural polymer having a solubility in water of 0.1-5.0 g/cm$^3$ at 20° C., a melting point of 50° C. or higher, and a molecular weight of 5000 or more.

5. The solid preparation according to claim 3, wherein the hydrophilic polymer assistant is polyethylene glycol.

6. The solid preparation according to claim 1 which further contains a hydrophilic assistant having a solubility in water of 0.1-5.0 g/cm$^3$, and a molecular weight of 1000 or less.

7. The solid preparation according to claim 6, wherein the hydrophilic assistant is at least one member selected from the group consisting of sugar-alcohols, sugars, surface active agents, salts, organic acids, amino acids, and amino sugars.

8. The solid preparation according to claim 6, wherein the hydrophilic assistant is selected from sorbitol and/or sucrose.

9. The solid preparation according to claim 1, wherein a swelling degree in compression direction in compression molding is 1.0-2.0 and a ratio of swelling degree obtained by dividing the swelling degree in the compression direction by a swelling degree in a direction perpendicular to the compression direction is 0.5-1.5.

10. The solid preparation according to claim 1, wherein the at least one active ingredient is a pharmaceutical active ingredient.

11. The solid preparation according to claim 1 which is a layered tablet comprising at least two superposed layers, wherein (a) a first layer contains the active ingredient, (b) a second layer is disposed in contact with the first layer, and (c) one or both of the first and second layers contain the dissolution-controlling base substance.

12. The solid preparation according to claim 11, wherein the second layer further contains the active ingredient.

13. The solid preparation according to claim 11, wherein the first layer of the solid tablet has an upper surface and a bottom surface, and only one of the upper surface and the bottom surface contacts with the second layer.

14. The solid preparation according to claim 11, wherein the first layer and the second layer are disposed concentrically, and the first layer constitutes an inner layer and the second layer constitutes an outer layer.

15. The solid preparation according to claim 1 which further contains coating granules.

16. The solid preparation according to claim 1 which further contains a lubricant comprising a combination of at least one member selected from the group consisting of a sucrose fatty acid ester, talc and light silicic acid anhydride with magnesium metasilicate aluminate.

17. The solid preparation according to claim 1 which has a weight of 0.2 g or more.

18. A solid preparation according to claim 1, wherein the modified starch is produced by a method which comprises steps of heating a starchy raw material at 60° C. or higher and lower than 100° C. in the presence of water to swell starch particles of the starchy raw material, drying the swollen starch particles to obtain a powder mixture containing starch particles and amylose and amylopectin present outside the starch particles, and grinding the resulting dry powder to adjust the particle size.

19. A solid preparation according to claim 1, wherein the modified starch is produced by a method which comprises steps of heat treating a starchy raw material at 100-130° C. under reduced pressure, and further heating the starchy raw material at 60-150° C. in the presence of water to swell starch particles of the starchy raw material, drying the swollen starch particles to obtain a powder mixture containing starch particles and amylose and amylopectin present outside the starch particles, and grinding the resulting dry powder to adjust the particle size.

20. The solid preparation according to claim 18, wherein the starchy raw material is potato starch.

21. The solid preparation according to claim 2, wherein the dissolution-controlling base substance further contains a hydrophilic polymer assistant and the weight ratio of the modified starch to the hydrophilic polymer assistant is in the range of 50:50-99.9:0.1.

22. The solid preparation according to claim 21, wherein the hydrophilic polymer assistant is a synthetic or natural polymer having a solubility in water of 0.1-5.0 g/cm³ at 20° C., a melting point of 50° C. or higher, and a molecular weight of 5000 or more.

23. The solid preparation according to claim 22, wherein the hydrophilic polymer assistant is polyethylene glycol.

24. The solid preparation according to claim 23 which further contains a hydrophilic assistant having a solubility in water of 0.1-5.0 g/cm³, and a molecular weight of 1000 or less.

25. The solid preparation according to claim 24, wherein the hydrophilic assistant is at least one member selected from the group consisting of sugar-alcohols, sugars, surface active agents, salts, organic acids, amino acids, and amino sugars.

26. The solid preparation according to claim 25, wherein the hydrophilic assistant is selected from sorbitol and/or sucrose.

27. The solid preparation according to claim 26, wherein a swelling degree in compression direction in compression molding is 1.0-2.0 and a ratio of swelling degree obtained by dividing the swelling degree in the compression direction by a swelling degree in a direction perpendicular to the compression direction is 0.5-1.5.

28. The solid preparation according to claim 27, wherein the at least one active ingredient is a pharmaceutical active ingredient.

29. The solid preparation according to claim 28 which is a layered tablet comprising at least two superposed layers, wherein (a) a first layer contains the active ingredient, (b) a second layer is disposed in contact with the first layer, and (c) one or both of the first and second layers contain the dissolution-controlling base substance.

30. The solid preparation according to claim 29, wherein the second layer further contains the active ingredient.

31. The solid preparation according to claim 30, wherein the first layer of the solid tablet has an upper surface and a bottom surface, and only one of the upper surface and the bottom surface contacts with the second layer.

32. The solid preparation according to claim 30, wherein the first layer and the second layer are disposed concentrically, and the first layer constitutes an inner layer and the second layer constitutes an outer layer.

33. The solid preparation according to claim 32 which further contains coating granules.

34. The solid preparation according to claim 33 which further contains a lubricant comprising a combination of at least one member selected from the group consisting of a sucrose fatty acid ester, talc and light silicic acid anhydride with magnesium metasilicate aluminate.

35. The solid preparation according to claim 34 which has a weight of 0.2 g or more.

36. A solid preparation according to claim 35, wherein the modified starch is produced by a method which comprises steps of heating a starchy raw material at 60° C. or higher and lower than 100° C. in the presence of water to swell starch particles of the starchy raw material, drying the swollen starch particles to obtain a powder mixture containing starch particles and amylose and amylopectin present outside the starch particles, and grinding the resulting dry powder to adjust the particle size.

37. A solid preparation according to claim 35, wherein the modified starch is produced by a method which comprises steps of heat treating a starchy raw material at 100-130° C. under reduced pressure, and further heating the starchy raw material at 60-150° C. in the presence of water to swell starch particles of the starchy raw material, drying the swollen starch particles to obtain a powder mixture containing starch particles and amylose and amylopectin present outside the starch particles, and grinding the resulting dry powder to adjust the particle size.

38. The solid preparation according to claim 37, wherein the starchy raw material is potato starch.

39. The solid preparation according to claim 7, wherein the hydrophilic assistant is at least one selected from the group consisting of sugar-alcohols and sugars.

40. The solid preparation according to claim 8, wherein the hydrophilic assistant is sorbitol.

41. The solid preparation according to claim 16, wherein the lubricant is a combination of talc with magnesium metasilicate aluminate.

42. A solid preparation which comprises at least one active ingredient and at least one dissolution-controlling base substance and is obtained by compression molding, wherein the dissolution-controlling base substance contains a modified starch such that the solid preparation contains 5.0-99.9% by weight of the modified starch based on the total weight of the solid preparation, the modified starch having a moisture retaining capacity of 400% or more and a gel indentation load of 200 g or more, the modified starch containing a water-soluble ingredient in an amount of 40-95% by weight based on the total weight of the modified starch, the modified starch having particles passing through a 75 μm-mesh sieve in the proportion of 90% by weight or more and particles passing through a 32 μm-mesh sieve in the proportion of 20% by weight or more, and having an average particle diameter of not smaller than 20 μm and smaller than 50 μm,
- wherein the dissolution-controlling base substance further contains a hydrophilic polymer assistant and the weight ratio of the modified starch to the hydrophilic polymer assistant is in the range of 50:50-99.9:0.1,
- wherein the dissolution-controlling base substance further contains a hydrophilic assistant having a solubility in water of 0.1-5.0 g/cm³, and a molecular weight of 1000 or less,
- wherein the modified starch has a swelling degree of 6-10 cm³/g,
- wherein a difference between a dissolution rate obtained from a dissolution test conducted using as a test solution the second solution specified in the Japanese pharmacopeia and a dissolution rate obtained from a dissolution test conducted using as a test solution the Mcilvaine solution is 7% or less, and
- wherein a difference between a dissolution rate obtained from a dissolution test on a solid preparation molded under a pressure of 120 MPa in compression molding and a dissolution rate obtained from a dissolution test on a solid preparation molded under a pressure of 300 MPa in compression molding is 7% or less.

43. The solid preparation according to claim 42, wherein the active ingredient is acetaminophen.

* * * * *